(12) United States Patent
Jane et al.

(10) Patent No.: US 7,408,048 B2
(45) Date of Patent: Aug. 5, 2008

(54) MAMMALIAN GRAINYHEAD TRANSCRIPTION FACTORS

(75) Inventors: Stephen Jane, Canterbury (AU); Tomasz Wilanowski, Parkville (AU); Stephen Ting, Elwood (AU)

(73) Assignee: Melbourne Health, Parkville, Victoria (AU)

( * ) Notice: Subject to any disclaimer, the term of this patent is extended or adjusted under 35 U.S.C. 154(b) by 0 days.

(21) Appl. No.: 10/524,619

(22) PCT Filed: Aug. 8, 2003

(86) PCT No.: PCT/AU03/01006

§ 371 (c)(1), (2), (4) Date: Nov. 10, 2005

(87) PCT Pub. No.: WO2004/015108

PCT Pub. Date: Feb. 19, 2004

(65) Prior Publication Data

US 2006/0162001 A1   Jul. 20, 2006

Related U.S. Application Data

(60) Provisional application No. 60/402,055, filed on Aug. 9, 2002.

(30) Foreign Application Priority Data

Aug. 22, 2002   (AU) .............................. 2002951579

(51) Int. Cl.
*C12N 15/11*   (2006.01)
*C12Q 1/68*    (2006.01)
*C12N 15/63*   (2006.01)

(52) U.S. Cl. .......................... 536/23.1; 435/6
(58) Field of Classification Search .................. None
See application file for complete search history.

(56) References Cited

FOREIGN PATENT DOCUMENTS

| EP | 1 074 617 A2 | 2/2001 |
|----|--------------|--------|
| WO | WO 00/58473 A2 | 10/2000 |
| WO | WO 01/75067 A2 | 10/2001 |
| WO | WO 02/30268 A2 | 4/2002 |
| WO | WO 02/070539 A2 | 9/2002 |
| WO | WO 02/071928 A2 | 9/2002 |
| WO | WO 03/006618 A2 | 1/2003 |

OTHER PUBLICATIONS

GenBank Entry AY231160, pp. 1-2.*
GenBank Entry BM460207, pp. 1-2.*
Wilanowski, T et al. "Four new members of a highly conserved family of transcription factors related to Dorsophila gainyhead," Development Growth and Differentiation (2001) 43: S87 (XP002376497).

Database EMBL cDNA FLJ23806 fis, clone HRC03576 *Homo sapiens* (2002) (XP002376500).
Database EMBL CDNA FLJ23806 fis, clone HRC03576 *Homo sapiens* (2002) (XP002376501).
European Search Report, Application No. EP 03 78 3841.
DGENE Abstract Accession No. AAG67096, CN 1303939 (Shanghai Borong Gene Dev. Co. Ltd.) Jul. 18, 2001.
Tomasz Wilanowski et al., *A Highly Conserved Novel Family Of Mammalian Developmental Transcription Factors Related To Drosophila grainyhead*, Mechanisms of Development 114 (1-2) (2002) 37-50; GenBank Accession No. AF411210, AF411211, AF411212, AF411213, XP_018275 & XP_002272.
Genbank Accession No. AF411210.
Genbank Accession No. AF411211.
Genbank Accession No. AF411212.
Genbank Accession No. AF411213.
Genbank Accession No. XP_018276.
Genbank Accession No. XP_002272.
Stephen B. Ting, et al. *The Identification And Characterization of Human Sister-of- Mammalian grainyhead (SOM) Expands The grainyhead-like Family of Developmental Transcription Factors*, Biochem. J. (2003) 370 (Pt. 3), 953-962 (Printed in Great Britain); GenBank Accession No. AY231160, AY231161.
Genbank Accession No. AY231160.
Genbank Accession No. AY231161.
Ningwu Huang, et al., *Cloning of Factors Related to HIV-inducible LBP Proteins That Regulate Steroidogenic Factor-1-independent Human Placental Transcription of the Cholesterol Side-chain Cleavage Enzyme, P450ssc*, The Journal of Biological Chemistry, vol. 275, No. 4, Jan. 28, 2000, pp. 2852-2858 (Printed in USA); GenBank Accession No. AF198489 & GenPept database Accession No. AAF32276.
Genbank Accession No. AF198489.

(Continued)

*Primary Examiner*—David Guzo
*Assistant Examiner*—Michele K Joike
(74) *Attorney, Agent, or Firm*—Knobbe, Martens, Olson & Bear LLP

(57) ABSTRACT

The present invention provides mammalian homologs of the *Drosophila* Grainyhead (GRH) transcription factor, call MGR and means of identifying such proteins and their genes. Nucleic acid and protein sequences are provided for human and mouse MGR transcription factors. In addition mammalian isoforms of MGR including human MGR p49, human p70, mouse p70, mouse MGR p61, and human and mouse homologs of MGR, brother of mgr (BOM) and sister of mgr (SOM), are disclosed. Antibodies to and methods of using these identified MGR, BOM and SOM transcription factors are also provided. The present invention further provides medical assessment systems including drug evaluation systems comprising genetically modified animals.

6 Claims, 19 Drawing Sheets

OTHER PUBLICATIONS

Genbank Accession No. AAF32276.
PCT International Search Report, Melbourne Health et al., PCT/AU03/01006, dated Sep. 19, 2003.
Strausberg R L et al., (2002) Proc. Natl. Acad. Sci USA 99(26): 16899-16903, *Generation And Initial Analysis of More Than 15,000 Full-length Human And Mouse cDNA Sequences*; GenBank Accession No. BC013080, BC036890, BC037233, BC042575, BC055035.
Genbank Accession No. BC013080.
Genbank Accession No. BC036890.
Genbank Accession No. BC037233.
Genbank Accession No. BC042575.
Genbank Accession No. BC055035.

* cited by examiner

```
p70 MGR:    1    MTQEYDNKRPVLVL---QNEALYPQRRSYTSEDEAWKSFLENPLTAATKAMMSINGDEDS    57
                 M+QE DN + ++ L    ++  +   RR+YTSEDEAWKS+LENPLTAATKAMMSINGDEDS
BOM:        1    MSQESDNNKRLVALVPMPSDPPFNTRRAYTSEDEAWKSYLENPLTAATKAMMSINGDEDS    60

P70 MGR:   58    AAALGLLYDYYKVPRERRSSAVKPEGEHPEPEHSKRNSIPNVTEQPLISAGENRVQVLKN   117
                 AAALGLLYDYYKVPR++R  +V    +     KRN +       Q   +S GENRVQVLK
BOM:       61    AAALGLLYDYYKVPRDKRLLSVSKASDSQE-DQDKRNCLGTSEAQINLSGGENRVQVLKT   119

P70 MGR:  118    VPFNIVLPHSN
                 VP N+ L  +
BOM:      120    VPVNLCLSQDH
```

Figure 1a

AGGCCCGAGCCCCAGCGCCCAGTGCGCGGCAGCCCGCGGCCCGAGCCCTCAGAGCGAGAAAGCGAACCCAACCC
CAGAGTGGCCTACTGGCATGTTTCTAGGGCAGGCATTTAGCTGCTAGTTGATTGATGTAGGAGGGCTCAGCC
CACTGTGGGGTGGTGCCATCCTTAGGCAGGCAGACCTGGG[TATATAAGAAAGT]AGCTGGGTGAGTGGAAGC
  GC BOX                                              TATA BOX
AGGGCCAGTAAG[CAGTGTT]CCTCCCATGGGTTCCTTGAGTTCCTTGACAATGGCTTCCCTTGATGATGAACTGTGT
            CAP SITE
GACCTGTGGGCCTCCTCCCTCCTCCACGCTACTTTTGGTTATCATGTTTATCAGAGCAACAGAGATGCAAGCA
SPLICE SITE

Figure 1c

```
TAGGAGTGAGTGAGCCGGCGAAACCGGTCGCATGGGGCAGGTGACA    Drosophila engrailed
            A  C   AAACCGG       A
ACACCCCACCCACACAAACACAAACCGGCAGTGACAACAACCACCCAT  human engrailed-1
                  CAAACCGGT  TG
                  YNAACYGGTYYTGCGG               Drosophila consensus
```

MAMMALIAN GRAINYHEAD TRANSCRIPTION FACTORS

RELATED APPLICATIONS

This is the United States National Phase under 35 U.S.C. §371 of International Application PCT/AU03/001006, filed Aug. 8, 2003, which claims priority to U.S. Provisional Application 60/402,055, filed Aug. 9, 2002, herein incorporated by reference.

FIELD OF THE INVENTION

The present invention relates generally to diagnostic and therapeutic agents. More particularly, the present invention provides mammalian transcription factors which function in the modulation of expression of genetic sequences. The present invention further provides nucleic acid molecules encoding the transcription factors as well as nucleic acid and/or proteinaceous molecules with which the transcription factors interact. The transcription factors of the present invention or molecules interacting with same may be used inter alia in the generation of a range of diagnostic and therapeutic agents for a range of conditions. Therapeutic agents include gene-expression modulating agents including sense and anti-sense molecules, ribozymes and RNAi-type molecules. The present invention further provides medical assessment systems including drug evaluation systems comprising genetically modified animals.

BACKGROUND OF THE INVENTION

Reference to any prior art in this specification is not, and should not be taken as, an acknowledgment or any form of suggestion that this prior art forms part of the common general knowledge in any country.

Bibliographic details of references provided in the subject specification are listed at the end of the specification.

The increasing sophistication of recombinant DNA techniques has provided significant progress in understanding the mechanisms involved in regulating eukaryotic gene expression. This is greatly facilitating research and development in the plant, agricultural, medical and veterinary industries. Transcription factors are an important component in the control of gene expression. However, despite their importance, mammalian transcription factors have not been well investigated for their diagnostic and therapeutic potential.

RNA polymerases in eukaryotic cells cannot initiate transcription alone; before transcription can begin, they require interaction between transcription factors and the promoter. These factors assemble at the promoter and, via a series of steps, facilitate both the binding of RNA polymerase II to the promoter and its subsequent phosphorylation and release to initiate transcription.

In addition to these general transcription factors, many thousands of transcription activators and/or negative regulators (inhibitors) exist, which control the process of initiation of gene transcription from great distances along the DNA. These factors influence the timing and extent of transcription of a particular gene. Indeed, they control whether and to what extent a particular gene is transcribed in a cell of a particular tissue type. Although most gene regulators identified to date have been found to be proteins, some transcription factors may also be RNA molecules.

In *Drosophila*, the transcription factor known as "Grainyhead" regulates key developmental process in the embryo and is encoded by the gene grainyhead. During development, Grainyhead is initially involved in dorsal/ventral and terminal patterning of the newly fertilized embryo through the formation of multi-protein complexes that repress transcription from the decapentaplegic, tailless and zerknuellt genes (Huang et al., *Genes Dev.* 9: 3177-3189, 1995; Liaw et al., *Genes Dev.* 9: 3163-3176, 1995). Later, grainyhead is predominantly expressed in the embryonic central nervous system in cuticle-producing tissues, where it binds to promoters and influences transcription from other developmentally regulated genes including engrailed, fushi tarazu and Ultrabithroax (Bray et al., *Genes Dev.* 3: 1130-1145, 1989; Dynlacht et al., *Genes Dev.* 3: 1677-1688, 1989; Biggin and Tjian, *Cell* 53: 699-711, 1988; Soeller et al., *Genes Dev.* 2: 68-81, 1988; Dynlacht et al., *Cell* 56: 563-576, 1991; Attardi and Tjian, *Genes Dev.* 7: 1341-1353, 1993; Uv et al., *Mol. Cell Biol.* 14: 4020-4031, 1994).

The importance of grainyhead in *Drosophila* development is emphasised by the embryonic lethal phenotype observed in flies carrying mutations in this gene. The embryos have flimsy cuticles, grainy and discontinuous head skeletons and patchy tracheal tubes (Bray and Kafatos, *Genes Dev.* 5: 1672-1683, 1991). A neuroblast-specific isoform of the protein, arising from alternate splicing, has also been identified. A mutation that abolishes this isoform is pupal- and adult-lethal, and flies demonstrate uncoordinated movements (Uv et al., *Mol. Cell Biol.* 17: 6727-6735, 1997).

Mammalian homologs of grainyhead have previously been proposed, including three genes designated CP2, LBP-1a and LBP-9. Studies have implicated them in a wide variety of cellular and developmental events including T cell proliferation, globin gene expression and steroid biosynthesis (Sueyoshi et al., *Mol. Cell Biol.* 15: 4158-4166, 1995; Jane et al., *EMBO J.* 14-97-105, 1995; Volker et al., *Genes Development* 11: 1435-1446, 1997; Zhou et al., *Mol. Cell Biol.* 20: 7662-7672, 2000). However, in situ analyses of both CP2 and LBP-1a reveal ubiquitous expression of both genes, unlike the highly restricted pattern observed with grainyhead in *Drosophila* (Bray et al., 1989, supra; Dynlacht et al., 1989, supra; Bray and Kafatos, 1991, supra; Ramamurthy et al., *J. Biol. Chem.* 276: 7836-7842, 2001). It is concluded, therefore, that these genes are not close homologs of grainyhead.

Abnormalities in mammalian transcription factor expression are considered to play a role in a number of different genetic disorders and birth defects such as spina bifida and anencephaly. There is therefore a need to identify mammalian transcription factors and in particular close mammalian homologs of Grainyhead and to use these to develop a range of diagnostic and therapeutic agents.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A sequence listing is provided at the end of the specification. A summary of the SEQ ID NOs is provided in Table 1.

Genetic sequences were studied which exhibited homology at the nucleotide and/or amino acid level to a *Drosophila* gene, the product of which, is involved in body patterning where a fine balance between activation and inhibition of gene expression is critical to the correct development of cells and tissues into functional organisms. A large number of different families of transcription factors play a critical role in ensuring that this balance is maintained during embryological development. One such transcription factor, cloned from *Drosophila* and well-characterized, is Grainyhead (hereinafter referred to by its abbreviation, GRH). GRH is encoded by the gene grainyhead (grh). The inventors observed that the identity of previously published putative grh mammalian homologs showed much more ubiquitous expression compared with the highly restricted pattern exhibited by *Drosophila* grh. Furthermore, sequence similarity between the proposed mammalian homologs and the *Drosophila* grh sequence was relatively low. In accordance with the present invention, true grh homologs were identified and derived from mammalian tissue such as human and mouse tissue.

Accordingly, one aspect of the present invention provides an isolated nucleic acid molecule comprising a sequence of nucleotides encoding or complementary to a sequence encoding a mammalian homolog of *Drosophila* GRH. A mammalian homolog of GRH is referred to herein as M-GRH. The corresponding gene is referred to as M-grh. A M-grh is deemed a homolog of *Drosophila* grh (D-grh). If it comprises a nucleotide sequence having 60% or greater similarity to the nucleotide sequence of D-grh after optimal alignment. Likewise, a M-GRH is so defined if it comprises an amino acid sequence having 60% or greater similarity to the amino acid sequence of *Drosophila* GRH (D-GRH). There are four isoforms of *Drosophila* grh designated D-grh P1, D-grh P2, D-grh P3 and D-grh P4. The nucleotide sequence encoding D-grh is set forth in SEQ ID NO:17 and SEQ ID NO:34, SEQ ID NO:36 and SEQ ID NO:38, respectively. Mammalian sequences encompassed by the present invention include those derived from tissues of mouse and human including, for example, mouse embryo, human fetal brain and placenta, and mouse and human kidney. Reference herein to *Drosophila* grp includes any or all of its isoforms P1-P4.

The mammalian sequences identified by the present inventors show higher percentages of similarity to the D-grh sequence than the already identified mammalian sequences designated CP2, LBP-1a and LBP-9. In accordance with the present invention, it is proposed that the M-grh homologs disclosed are "true" grh homologs relative to CP2, LBP-1a and LBP-9. As a result of the analysis herein described, it is shown that the earlier sequences align phylogenetically with another distinct *Drosophila* factor, designated *Drosophila* CP2. A new family of transcription factors, highly conserved from *Drosophila* to human and having distinct tissue-specificity profiles, is now described in accordance with the present invention.

The true M-grh homologs of the present invention include mammalian grainyhead (gene: mgr; expression product: MGR), brother of mgr (gene: bom; expression product: BOM) and sister of mgr (gene som: protein: SOM). MGR has multiple isoforms including MGR p49 and MGR p70 in humans and MGR p61 in mice. A summary of the SEQ ID NOs for the M-grh and M-GRH molecules of the present invention are shown in Table 2. The sequences are provided in the Sequence Listing. The gene som and its product SOM are also referred to herein as grhl3 and GRHL3, respectively.

The present invention provides, therefore, expression products of the M-grh genes, mgr, bom and som as well as derivatives and homologs thereof. This aspect of the present invention does not extend to CP2, LBP-1a or LBP-9.

Accordingly, another aspect of the present invention provides an isolated nucleic acid molecule comprising a sequence of nucleotides encoding a polypeptide comprising a predicted amino acid sequence substantially as set forth in SEQ ID NO:2 (human MGR p49), SEQ ID NO:4 (human MGR p70), SEQ ID NO:6 (human BOM), SEQ ID NO:8 (human SOM), SEQ ID NO:10 (murine MGR p49), SEQ ID NO:12 (murine MGR p70), SEQ ID NO:14 (murine BOM) or SEQ ID NO:16 (murine SOM) or an amino acid sequence having at least about 60% similarity to SEQ ID NO:2, SEQ ID NO:4, SEQ ID NO:6, SEQ ID NO:8, SEQ ID NO:10, SEQ ID NO:12, SEQ ID NO:14, SEQ ID NO:16 after optimal alignment.

The preferred nucleic acid molecules comprise sequences of nucleotides substantially as set forth in SEQ ID NO:1 (human mgr p49), SEQ ID NO:3 (human mgr p70), SEQ ID NO:5 (human bom), SEQ ID NO:7 (human som), SEQ ID NO:9 (murine mgr p61), SEQ ID NO:11 (murine mgr p70), SEQ ID NO:13 (murine bom) or SEQ ID NO:15 (murine som) or complementary forms thereof, or a nucleotide sequence having at least about 60% similarity to SEQ ID NO:1, SEQ ID NO:3, SEQ ID NO:5, SEQ ID NO:7, SEQ ID NO:9, SEQ ID NO:11, SEQ ID NO:13 or SEQ ID NO:15 after optimal alignment or their complementary forms or a nucleotide sequence capable of hybridizing to SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or complementary forms thereof under low stringency conditions. Again, this aspect of the present invention does not extend to nucleic acid molecules encoding CP2, LBP-1 and LBP-9.

The present invention further extends to recombinant forms of the M-GRH molecules. Preferred recombinant M-GRH molecules having amino acid sequences defined in parenthesis include human MGR p49 (SEQ ID NO:2), human MGR p70 (SEQ ID NO:4), human BOM (SEQ ID NO:6), human SOM (SEQ ID NO:8), murine MGR p61 (SEQ ID NO:10), murine MGR p70 (SEQ ID NO:12), murine BOM (SEQ ID NO:14) and murine SOM (SEQ ID NO:16).

Reference to "M-GRH" molecules include derivatives, homologs and analogs thereof.

The mammalian transcription factors of the present invention are proposed to be involved in the regulation of expression of a range of genes such as but not limited to developmentally regulated genes involved in determining patterning. Some of the genes regulated encode critical products, the absence or malfunctioning of which, is proposed to lead to unwanted phenotypes and/or predispositions to certain medical conditions. That is, the presence of a mutation in and/or malfunction of a M-grh including over or under expression of the transcription factors of the present invention are proposed to cause incorrect regulation of one or more of these genes thereby leading to an inappropriate phenotype. The ability to detect mutations in the nucleotide sequences encoding the M-grh homologs permits the detection of a range of abnormalities or a predisposition for development of abnormalities. Furthermore, as many of the genes will be developmentally regulated genes, identification of the transcription factors permits identification of unknown developmentally regulated genes.

Accordingly, another aspect of the present invention contemplates a method for detecting a variation in a polynucleotide sequence encoding a M-GRH transcription factor.

Furthermore, the isolated nucleic acid molecules of the present invention may be able to be used to correct such an abnormality in a subject in need thereof or at risk of developing an abnormality. The nucleic acid molecules of the present invention may be comprised, therefore, within a suitable vector for delivery of all or part of the sequence to a recipient cell or tissue. The nucleic acid molecule or part thereof could also be administered directly for transient expression. The present invention provides, therefore, the potential for both a diagnostic and a therapeutic capability.

Accordingly, a further aspect of the present invention contemplates a genetic construct comprising a nucleotide sequence selected from SEQ ID NO:1, SEQ ID NO:3, SEQ ID NO:5, SEQ ED NO:7, SEQ ID NO:9, SEQ ID NO:11, SEQ ID NO:13, SEQ ID NO:15 or a nucleotide sequence having at least 60% similarity to one or more of SEQ ID NO:1, SEQ ID NO:3, SEQ ID NO:5, SEQ ID NO:7, SEQ ED NO:9, SEQ ID NO:11, SEQ ID NO:13 or SEQ ID NO:15 after optimal alignment or a nucleotide sequence capable of hybridizing to SEQ ED NO:1, SEQ ED NO:3, SEQ ID NO:5, SEQ ID NO:7, SEQ ID NO:9, SEQ ID NO:11, SEQ ID NO:13 or SEQ ID NO:15 or a complementary form thereof under low stringency conditions.

In a related embodiment, the present invention provides a genetic construct comprising a promoter or functional equivalent thereof operably linked to a nucleotide sequence of the invention.

The present invention further provides animal models comprising genetically altered M-grh sequences including insertions, deletions, additions, and substitutions. Such animal models including genetically modified animals are useful in the development of medical assessment systems such as to monitor physiological changes and to evaluate drug targets and drug candidates. The medical assessment system may also be used in drug development.

Examples of drugs or other therapeutic agents include genetic agents such as sense and antisense molecules, ribozymes, DNAzymes, methylakion- or demethylation-inducing agents as well as RNAi-type agents. Peptide mimetics and non-protenaceous chemical entities are also contemplated by the present invention.

Genes are represented herein in lower case italics. Expression products (e.g. proteins or RNA) are represented in upper case, non-itallic letters. A summary of the genes and their expression products is provided in Table 1. The gene "som" or its expression product "SOM", are also referred to as grhl3 and GRHL3, respectively.

TABLE 1

| Abbreviations | |
|---|---|
| GENE | EXPRESSION PRODUCT |
| grainyhead (grh) | Grainyhead (GRH) |
| mammalian grainyhead homologs (M-grh) | mammalian grainyhead homologs (M-GRH) |
| mammalian grainyhead (mgr) | mammalian Grainyhead (MGR) |
| brother of mammalian grainyhead (bom) | brother of mammalian grainyhead (BOM) |
| sister of mammalian grainyhead (som) | sister of mammalian grainyhead (SOM) |

A summary of sequence identifiers used throughout the specification is Table 2.

TABLE 2

Summary of sequence identifiers

| SEQUENCE ID NO: | NAME | DESCRIPTION |
|---|---|---|
| 1 | human mgr p49 | Nucleotide sequence encoding mammalian grainyhead derived from human fetal brain |
| 2 | human MGR p49 | Predicted amino acid sequence corresponding to SEQ ID NO:1 |
| 3 | human mgr p70 | Nucleotide sequence encoding mammalian grainyhead being an isoform of SEQ ID NO:1, derived from human kidney |
| 4 | human MGR p70 | Predicted amino acid sequence corresponding to SEQ ID NO:3 |
| 5 | human bom | Nucleotide sequence encoding mammalian grainyhead derived from human placenta |
| 6 | human BOM | Predicted amino acid sequence corresponding to SEQ ID NO:5 |
| 7 | human som | Nucleotide sequence encoding mammalian grainyhead |
| 8 | human SOM | Predicted amino acid sequence corresponding to SEQ ID NO:7 |
| 9 | murine mgr p61 | Nucleotide sequence encoding mammalian grainyhead derived from 17.5 day murine embryo |
| 10 | murine MGR p61 | Predicted amino acid sequence corresponding to SEQ ID NO:9 |
| 11 | murine mgr p70 | Nucleotide sequence encoding mammalian grainyhead being an isoform of SEQ ID NO:9, derived from murine kindney |
| 12 | murine MGR p70 | Predicted amino acid sequence corresponding to SEQ ID NO:11 |
| 13 | murine bom | Nucleotide sequence encoding mammalian grainyhead derived from a murine embryonic carcinoma cell line (p19) |
| 14 | murine BOM | Predicted amino acid sequence corresponding to SEQ ID NO:13 |
| 15 | murine som | Nucleotide sequence encoding mammalian grainyhead |
| 16 | murine SOM | Predicted amino acid sequence corresponding to SEQ ID NO:15 |
| 17 | grh-P1 | Nucleotide sequence encoding the *Drosophila* transcription factor designated Grainyhead (grh) |

TABLE 2-continued

Summary of sequence identifiers

| SEQUENCE ID NO: | NAME | DESCRIPTION |
|---|---|---|
| 18 | GRH-P1 | Amino acid sequence corresponding to SEQ ID NO:18 |
| 19-20 | human p49 mgr | primers |
| 21-22 | human p70 mgr | primers |
| 23-24 | human bom | primers |
| 25-26 | murine P70 mgr | primers |
| 27-28 | murine p61 mgr | primers |
| 29-30 | murine bom | primers |
| 31-32 | human S14 | primers |
| 33 | *Drosophila* dopa decarboxylase | promoter |
| 34 | *Drosophila* PCNA | promoter |
| 35 | human Engrailed-1 | promoter |
| 36 | grh-P2 | Nucleotide sequence encoding the *Drosophila* transcription factor designated Grainyhead (grh) isoform P2 |
| 37 | GRH-P2 | Amino acid sequence corresponding to SEQ ID NO:36 |
| 38 | grh-P3 | Nucleotide sequence encoding the *Drosophila* transcription factor designated Grainyhead (grh) isoform P3 |
| 39 | GRH-P3 | Amino acid sequence corresponding to SEQ ID NO:38 |
| 40 | GRHL-3 | Primer |
| 41 | GRHL-3 | Primer |
| 42 | GRHL-3 | Primer |
| 43 | HPRT | Primer |
| 44 | Antisense | Primer |
| 45 | Exon 8 and Exon 13 Sense | Primer |
| 46 | Antisense | Primer |

Figure 1B:
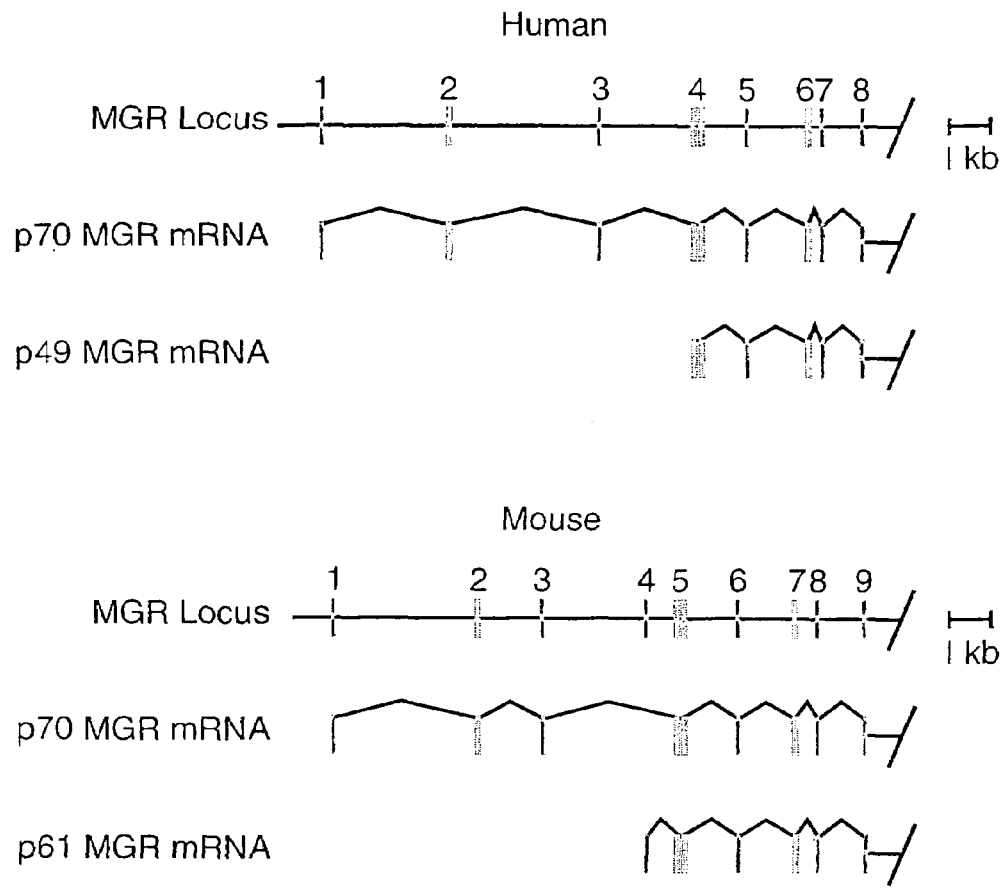
FIG. 1 is a representation showing that mgr genomic locus encodes two distinct isoforms. (A) Alignment of the predicted $NH_2$-terminal amino acid sequence of the p70 isoform of MGR (SEQ ID NO: 12, amino acids 1-128) and BOM (SEQ ID NO: 14, amino acids 1-130). Amino acid identity is denoted by shared upper case letters and similarity by the (+) symbol. Amino acid segments greater than 4 amino acids in length in the consensus sequence are represented by SEQ ID NO: 12, amino acids 26-35 and amino acids 37-72). The first amino acids shared between p61 MGR arid p70 MGR are given in bold. (B) Structure of the human and murine mgr genomic loci. Human genomic sequence was downloaded from the GenBank database (Accession Number AC010969) and aligned with cDNA sequences. Murine genomic clones were obtained 10 from a 129 library and mapped by Southern analysis and PCR. Exons are denoted as E1-8 in human and E1-9 in murine. The two human MGR isoforms are denoted as p70 and p49MGR and the two murine isoforms as p70 and p61 MGR. The scale of 1 kb is shown. (C) Identification of the murine p61 MGR promoter (SEQ ID NO:47). Sequence was obtained from intron three from the MGR genomic locus and analyzed using the weight matrices of Bucher, *J, Mol. Biol.* 212: 563-578, 1990. The CAP site, TATA box and GC box are indicated. The cDNA start site is shown in arrows, the first ATG is given in bold and the splice site at the end of the first exon of p61 MGR is indicated.

and the TK promoter linked to the Renilla luciferase reporter gene (hatched columns) in the presence and absence of a p70 MGR expression vector (PCI-p70 MGR) as indicated. Transfection with the empty vector (pCI) served as the control. Luciferase levels were corrected for protein concentration and values were derived from two independent experiments performed in triplicate.

FIG. 4 is a photographic representation showing expression of GRHL-3 from E8.5 to E15.5. Sections of murine embryos were analysed by in situ hybridisation with a GRHL-3-specific $^{33}$P-labelled antisense riboprobe. (A) Transverse section of an E8 embryo showing two discrete areas of intense expression in non-neuronal ectoderm (arrowed) adjacent to the folding neural plate (bottom panel). The section counter-stained with hematoxylin is shown (top panel). da, dorsal aorta; hd, hind-gut diverticula; ne, neural epithelium; se, surface ectoderm. (B) Transverse section of E8 embryo probed with the control sense riboprobe (bottom panel) and the hematoxylin counter-stain (top panel). (C,D) Saggital sections of E12.5 (C) and E15.5 (D) embryos showing increasingly intense hybridisation to surface ectoderm (C and D). Hybridisation is also noted to other tissues lined by squamous epithelium including oral cavity, urogenital sinus and anal canal (D). ac, anal canal; dea, descending aorta; dv, ductus venosus; gt, genital tubercle; he, heart; li, liver; nc, nasal cavity; np, nasal process; o, oral cavity; se, surface ectoderm; ta, tail; to, tongue; us, urogenital sinus. Signal from the descending aorta and ductus venosus is nonspecific due to reflection from retained erythrocytes.

FIG. 5 is a representation showing the generation of a null allele of GRHL-3. (A) Gene-targeting strategy applied to the mouse GRHL-3 locus. The homologous recombination event deleted 2.2 kb of genomic DNA, including the region encoding the entire transcriptional activation domain of the protein. This was replaced with a promoter-less lacZ.polyA cassette fused to the second codon of exon 2 and a Neo$^R$ gene linked to a PGK promoter and flanked by loxP sites. The thymidine kinase gene driven off the MC1-promoter completed the targeting vector. The location of the 5' and 3' probes used for Southern blot analysis of the targeted allele and the size of the expected hybridization fragments prior to excision of the Neo$^R$ cassette are shown. The Neo$^R$ cassette was excised by crossing mice heterozygous for the targeted allele with a kansgenic line expressing the Cre recombinase gene driven off a CMV-promoter. LacZ.polyA, the lacZ gene linked to the rabbit β-globin polyadenylation signal; B, BamHI; S. Spel. (B) Southern blot analysis of two targeted ES cell clones (C7 and B12) and the parental ES cells (G7) with the 5' flanking probe demonstrating site-specific integration by homologous recombination. The size of DNA standards (in kb) is indicated. (C) Germ-line transmission of the targeted allele from cell line C7. Southern blotting was performed with the 3' flanking probe on tail DNA isolated from weaned progeny of GRHL-3+/− intercrosses. The size of DNA standards (in kb) is indicated. (D) PCR genotyping of embryos. Two allele, three primer PCR was performed on genomic DNA from E18.5 embryos isolated from GRHL-3+/− intererosses. The size of DNA standards (in bp) is indicated target, PCR product diagnostic of targeted 25 GRHL-3 allele; wt. PCR product diagnostic of wild type GRHL-3 allele.

FIG. 6 is a photographic representation of the phenotype of the GRHL-3-deficient mice. (A) E18.5 littermate embryos, wild type (+/+) and deficient (−/−). The range of NTDs in the GRHL-3$^{−/−}$ embryos are illustrated; exencephaly (arrow) and thoraco-lumbo-sacral spina bifida (arrowhead). Curled tails and growth retardation are also apparent in these embryos. A magnified view of the curly tail (ct) and the spina bifida from a caudal longitudinal view (clv) are inset. (B,C) Alizarin red/Alcian blue stained full-body skeletal preparations of E18.5 littermates illustrating the kyphosis (k) and tail flexion deformity (ct) in (B), and the abnormal vertebral pedicles in the thoraco-lumbo-sacral regions of the GRHL-3$^{−/−}$ embryo in (B and C). np, normal pedicles; sp, splayed pedicles. (D) transverse sections through +/+ and −/− E8.5 to E14.5 embryos in the region of the caudal neural tube stained with hematoxylin and eosin. The open neural plate is arrowed.

FIG. 7 is a representation showing GRHL-3 and ct are the same gene. (A) Organization 20 of the ct candidate region. Genetic map of the 13 Mb supercontig (Accession number NW_000213) that shows the positions of relevant markers (D4Mit69 and D4Mit 157) and previously excluded ct candidate genes (Synd3, Fgr, Hspg2, Pax7). The position of the GRHL-3 locus is also indicated. The size of the interval between the GRHL-3 locus and the D4Mit69 marker is shown. (B) Morphological appearance and genotype of embryos derived from ct/ct mice crossed with GRHL-3$^{+/−}$ mice. Embryo 1 is unremarkable; embryos 2 and 3 display curly tails (arrowheads); embryos 4 and 5 display curly tails and lumbo-sacral spine bifida (arrows). ct. curly tail; SB, spine bifida. Scale bar=10 mm. (C) Total RNA from E14.5 embryos from curly tail (ct/ct), wild type (+/+) and GRHL-3 heterozygotes (+/−) were analysed for GRHL-3 expression by Northern blotting with a cDNA probe derived from the unique coding portion of the mRNA described in FIG. 1A (upper panel). RNA loading was monitored by probing with 28S (lower panel). Signal intensity was quantified by Phosphorimager densitometry and the individual embryo GRHL-3 signals corrected for 28S loading. The corrected signal intensities relative to wild type embryo 7 are shown. Positions of GRHL-3, 28S and the RNA size standards are indicated. (D) Quantitative real-time RT-PCR was performed on total RNA from E14.5 5 curly tail (ct/ct), wild type (+/+) and GRHL-3 heterozygous (+/−) embryos. A standard curve was generated for HPRT and GRHL-3 and the relative quantity of both transcripts was calculated for individual embryos. Each reaction was performed in duplicate. The ratios of GRHL-3/HPRT in GRHL-3$^{+/−}$ and ct/ct embryos were normalised to the values obtained with GRHL-3$^{+/+}$ embryos. (E) Northern blot analysis of GRHL-3 mRNA expression in wild type embryos and embryos heterozygous or homozygous for the targeted GRHL-3 allele (upper panel). RNA integrity was confirmed with a GAPDH probe (lower panel). The size of RNA standards is indicated, as is the migration of the GRHL-3 and GAPDH transcripts. (F) RT-PCR of E9.5 GRHL-3$^{−/−}$ and GRtIL-3$^{+/−}$ embryos was performed with primers specific for HPRT. Based on the HPRT quantitation, comparable amounts of cDNA from each embryo were PCR amplified for 30, 32 and 35 cycles (GRHL-3$^{+/−}$) or 35, 38 and 40 cycles (GRHL-3$^{−/−}$) with primers specific for GRHL-3. The 5' primer anneals to exon 8 and the 3' primer anneals to exon 13. Both primer pairs gave predicted size bands of 503 bp for GRHL-3 and 229 bp for HPRT. The identities of the amplified bands were confirmed by Southern blotting using gene-specific internal oligonucleotides.

DETAILED DESCRIPTION OF THE PREFERRED EMBODIMENTS

The present invention is predicated in part on the identification of mammalian homologs of the *Drosophila* transcription factor known as Grainyhead (GRH). GRH is encoded by the gene, grainyhead (grh) In *Drosophila*, mutations in this gene are associated with embryonic lethal phenotypes, indicating the importance of the gene for normal development and function. The mammalian homologs are proposed to be involved in the regulation of developmental and/or non-developmental genes. Identification and isolation of the mammalian homologs of grh (M-grh) enable the development of a range of diagnostic and therapeutic agents useful in the detection and treatment of genetic disorders.

The present invention provides, therefore, a family of mammalian-derived transcription factors, highly related from *Drosophila* to mammals. These transcription factors are more highly conserved than CP2, LBP-1a and LBP-9. The present invention does not extend to CP2, LBP-1 and LBP-9. Reference to a mammal in this context includes a human, livestock animal (e.g. sheep, cow, horse, pig, donkey, goat), laboratory test animal (e.g. mouse, rat, rabbit, guinea pig), companion animal (e.g. dog, cat) or captive wild animal. Most preferably, the animal is a human or murine species. Sources of the isolated nucleic acid molecules include a range of tissues, such as mouse embryo, human fetal brain and placenta, and mouse and human kidney. In view of the highly conserved nature of this family of M-grh nucleotide sequences, however, corresponding homologs from other tissues and from other mammalian species are intended to be included within the scope of the present invention. The term "homolog" as used herein, therefore, extends to encompass transcription factors from mammalian species encoded by nucleotide sequences which have substantial similarity to *Drosophila* grh or a conserved region thereof. At the protein level, a homolog includes an amino acid sequence and/or tertiary structure having similarity to *Drosophila* GRH. In cases where the expression product of the M-grh is RNA, a homolog is defined by reference to the similar ribonucleotide sequence to that encoded by *Drosophila* grh.

M-ghd or 1-GRH, i.e. a mammalian homolog of *Drosophila* grh or GRH is defined as such by having a nucleotide or amino acid sequence which has 60% or greater similarity after optimal alignment to *Drosophila* grh or GRH.

Accordingly, one aspect of the present invention provides an isolated nucleic acid molecule comprising a sequence of nucleotides encoding or complementary to a sequence encoding a mammalian homolog of *Drosophila* grh.

Reference to a mammalian homolog of *Drosophila* GRH (i.e. a M-GRH) preferably includes the mammalian homolog of grainyhead (MGR), brother of MGR (BOM) and sister of MGR (SOM). These transcription factors are encoded by mgr, bom and som, respectively. Reference to "MGR", "BOM" and "SOM" or mgr, bom and som includes all mutants, derivatives, homologs and analogs thereof. The present invention further extends, however, to all novel mammalian homologs of *Drosophila* grh but does not encompass CP2, LBP-1a or LBP-9. The nucleotide sequences for *Drosophila* grh are set forth in SEQ ID NO:17, SEQ ID NO:34, SEQ ID NO:36 and SEQ ID NO:38, respectively. Consequently, a mammalian homolog is defined herein as comprising a nucleotide sequence having at least about 60% sequence similarity to SEQ ID NO:17 or SEQ ID NO:34 or SEQ ID NO:36 or SEQ ID NO:38 after optimal alignment and/or being capable of hybridizing to SEQ ID NO:17 or SEQ ID NO:34 or SEQ ID NO:36 or SEQ ID NO:38 or its complementary form under low stringency conditions.

Accordingly, another aspect of the present invention provides an isolated nucleic acid molecule encoding a mammalian transcription factor or a functional part thereof comprising a sequence of nucleotides having at least 60% similarity to SEQ ID NO:17 or SEQ ID NO:34 or SEQ ID NO:36 or SEQ ID NO:38 after optimal alignment and/or being capable of hybridizing to SEQ ID NO:17 or its complementary form under low stringency conditions.

In a preferred embodiment, the isolated nucleic acid molecule encodes a proteinaceous form of a transcription factor. Examples of such mammalian protein transcription factors include human MGR p49 (SEQ ID NO:2), human MGR p70 (SEQ ID NO:4), human BOM (SEQ ID NO:6), human SOM (SEQ ID NO:7), murine MGR p61 (SEQ ID NO:10), murine MGR p70 (SEQ ID NO:12), murine BOM (SEQ ID NO:14) and murine SOM (SEQ ID NO:16).

Accordingly, another aspect of the present invention is directed to an isolated nucleic acid molecule comprising a sequence of nucleotides encoding a polypeptide having transcription factor activity and comprising an amino acid sequence substantially as set forth in SEQ ID NO:2, SEQ ID NO:4, SEQ ID NO:6, SEQ ID NO:8, SEQ ID NO:10, SEQ ID NO:12, SEQ ID NO:14 or SEQ ID NO:16 or an amino acid sequence having at least about 60% similarity to SEQ ID NO:2, SEQ ID NO:4, SEQ ID NO:6, SEQ ID NO:8, SEQ ID NO:10, SEQ ID NO:12, SEQ ID NO:14 or SEQ ID NO:16 after optimal alignment wherein said polypeptide is a mammalian homolog of *Drosophila* GRH.

Such a polypeptide is referred to herein as a M-GRH.

Preferred percentage amino acid similarity levels include at least about 61% or at least about 62% or at least about 63% or at least about 64% or at least about 65% or at least about 66% or at least about 67% or at least about 68% or at least about 69% or at least about 70% or at least about 71% or at least about 72% or at least about 73% or at least about 74% or at least about 75% or at least about 76% or at least about 77% or at least about 78% or at least about 79% or at least about 80% or at least about 81% or at least about 82% or at least about 83% or at least about 84% or at least about 85% or at least about 86% or at least about 87% or at least about 88% or at least about 89% or at least about 90% or at least about 91% or at least about 92% or at least about 93% or at least about 94% or at least about 95% or at least about 96% or at least about 97% or at least about 98% or at least about 99% similarity.

This aspect of the present invention includes derivatives of M-GRH molecules. Such derivatives include non-active fragments which encompass inter alia the binding domain as well as active isoforms.

A "derivative" of a polypeptide of the present invention also encompasses a portion or a part of a full-length parent polypeptide, which retains the transcription factor activity of the parent polypeptide. Such "biologically-active fragments" include deletion mutants and small peptides, for example, of at least 10, preferably at least 20 and more preferably at least 30 contiguous amino acids, which exhibit the requisite activity. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "*Peptide Syizthesis*" by Atherton and Shephard which is included in a publication entitled "*Synthetic Vaccines*" edited by Nicholson and published by Blackwell Scientific Publications. Alternatively, peptides can be produced by digestion of an amino acid sequence of the invention with proteinases such as endoLys-C, endoArg-C, endoGlu-C and staphylococcus V8-protease. The digested fragments can be purified by, for example, high performance liquid chromatographic (HPLC) techniques. Any such fragment, irrespective of its means of generation, is to be understood as being encompassed by the term "derivative" as used herein.

In another embodiment, the present invention provides an isolated nucleic acid molecule encoding a mammalian transcription factor homolog of *Drosophila* grh (i.e. a M-GRH) and comprising a nucleotide sequence selected from SEQ ID NO:1, SEQ ID NO:3, SEQ ID NO:5, SEQ ID NO:7, SEQ ID NO:9, SEQ ID NO:11, SEQ ID NO:13 and SEQ ID NO:15 or a nucleotide sequence having at least about 60% similarity to any one of SEQ ID NO:1, SEQ ID NO:3, SEQ ID NO:5, SEQ ID NO:7, SEQ ID NO:9, SEQ ID NO:11, SEQ ID NO:13 or SEQ ID NO:15 after optimal alignment or a nucleotide sequence capable of hybridizing to SEQ ID NO:1, SEQ ID NO:3, SEQ ID NO:5, SEQ ID NO:7, SEQ ID NO:9, SEQ ID NO:111, SEQ ID NO:13 or SEQ ID NO:15 or a complementary form thereof under low stringency conditions.

Preferably, percentage nucleotide similarity levels include at least about 61% 61% or at least about 62% or at least about 63% or at least about 64% or at least about 65% or at least about 66% or at least about 67% or at least about 68% or at least about 69% or at least about 70% or at least about 71% or at least about 72% or at least about 73% or at least about 74% or at least about 75% or at least about 76% or at least about 77% or at least about 78% or at least about 79% or at least about 80% or at least about 81% or at least about 82% or at least about 83% or at least about 84% or at least about 85% or at least about 86% or at least about 87% or at least about 88% or at least about 89% or at least about 90% or at least about 91% or at least about 92% or at least about 93% or at least about 94% or at least about 95% or at least about 96% or at least about 97% or at least about 98% or at least about 99% similarity.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (*Nucl. Acids. Res.* 25: 3389, 1997). A detailed discussion of sequence analysis can be found in Unit 19.3 of Ausubel et al. (In: Current Protocols in Molecular Biology, John Wiley & Sons Inc. 1994-1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

The present invention provides, therefore, an isolated nucleic acid molecule comprising a sequence of nucleotides selected from SEQ ID NO:1, SEQ ID NO:3, SEQ ID NO:5, SEQ ID NO:7, SEQ ID NO:9, SEQ ID NO:11, SEQ ID NO:13 and SEQ ID NO:15 or a complementary form thereof. Such nucleic acid molecules encode mammalian homologs of *Drosophila* grh. These mammalian homologs are proposed herein to be transcription factors.

The present invention extends to variants of the nucleic acid molecules. A variant is a molecule having less than 100% sequence identity to a M-grh. Generally, a variant will still hybridize to a M-grh sequence under low stringency conditions.

The term "variant" refers, therefore, to nucleotide sequences displaying substantial sequence identity with a reference nucleotide sequences or polynucleotides that hybridize with a reference sequence under stringency conditions that are defined hereinafter. The terms "nucleotide sequence", "polynucleotide" and "nucleic acid molecule" may be used herein interchangeably and encompass polynucleotides in which one or more nucleotides have been added or deleted, or replaced with different nucleotides. In this regard, it is well understood in the art that certain alterations inclusive of mutations, additions, deletions and substitutions can be made to a reference nucleotide sequence whereby the altered polynucleotide retains the biological function or activity of the reference polynucleotide. The term "variant" also includes naturally-occurring allelic variants.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m$=69.3+0.41 (G+C)% (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 0.1% w/v SDS at 25°-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The present invention extends to recombinant forms of the M-grh molecules as well as derivatives and homologs thereof.

Accordingly, another aspect of the present invention provides an isolated polypeptide having transcription factor activity, said polypeptide comprising a sequence of amino acids encoded by a nucleotide sequence selected from SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or a nucleotide sequence having at least about 60% similarity to any one of SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or a nucleotide sequence capable of hybridizing to any one of SEQ TD NO:1, SEQ ID NO:3, SEQ ID NO:5, SEQ ID NO:7, SEQ ID NO:9, SEQ ID NO:11, SEQ ID NO:13 or SEQ ID NO:15 or a complementary form thereof under low stringency conditions.

In a preferred embodiment, the present invention provides a recombinant M-grh comprising an amino acid sequence selected from SEQ ID NO:2, SEQ ID NO:4, SEQ ID NO:6, SEQ ID NO:8, SEQ ID NO:10, SEQ ID NO:12, SEQ ID NO:14 or SEQ ID NO:16 or an amino acid sequence having at least about 60% similarity to SEQ ID NO:2, SEQ ID NO:4, SEQ ID NO:6, SEQ ID NO:8, SEQ ID NO:10, SEQ ID NO:12, SEQ ID NO:14 or SEQ ID NO:16.

This aspect of the present invention extends to derivatives, homologs and analogs of M-GRH molecules.

A "derivative" includes a mutant, fragment, part, portion or hybrid molecule. A derivative generally but not exclusively carries a single or multiple amino acid substitution, addition and/or deletion.

A "homolog" includes an analogous polypeptide having at least about 60% similar amino acid sequence from another animal species or from a different locus within the same species.

An "analog" is generally a chemical analog. Chemical analogs of the subject polypeptide contemplated herein include, but are not limited to, modification to side chains, incorporation of unnatural amino acids and/or their derivatives during peptide, polypeptide or protein synthesis and the use of crosslinkers and other methods which impose conformational constraints on the proteinaceous molecule or their analogs.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic andydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 3.

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |

TABLE 3-continued

| Non-conventional amino acid | Code | Non-conventional amino acid | Code |
|---|---|---|---|
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |

TABLE 3-continued

| Non-conventional amino acid | Code | Non-conventional amino acid | Code |
|---|---|---|---|
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates chemical analogs of the subject polypeptide capable of acting as antagonists or agonists of M-GRH or which can act as functional analogs of M-GRH. Chemical analogs may not necessarily be derived from the instant M-GRH molecules but may share certain conformational similarities. Alternatively, chemical analogs may be specifically designed to mimic certain physiochemical properties of the subject M-GRH molecules. Chemical analogs may be chemically synthesized or may be detected following, for example, natural product screening. The latter refers to molecules identified from various environmental sources such a river beds, coral, plants, microorganisms and insects.

These types of modifications may be important to stabilize the subject M-GRH molecules if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

The designing of mimetics to a pharmaceutically active compound is a known approach to the development of pharmaceuticals based on a "lead" compound. This might be desirable where the active compound is difficult or expensive to synthesize or where it is unsuitable for a particular method of administration, e.g. peptides are unsuitable active agents for oral compositions as they tend to he quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g. by substituting each residue in turn. Alanine scans of peptides are commonly used to refine such peptide motifs. These parts or residues constituting the active region of the compound are known as its "pharmacophore".

Once the pharmacophore has been found, its structure is modeled according to its physical properties, e.g. stereochemistry, bonding, size and/or charge, using data from a range of sources, e.g. spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic. Modeling can be used to generate inhibitors which interact with the linear sequence or a three-dimensional configuration.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

The goal of rational drug design is to produce structural analogs of biologically active polypeptides of interest or of small molecules with which they interact (e.g. agonists, antagonists, inhibitors or enhancers) in order to fashion drugs which are, for example, more active or stable forms of the polypeptide, or which, e.g. enhance or interfere with the function of a polypeptide in vivo. See, e.g. Hodgson (*Bio-Technology* 9: 19-21, 1991). In one approach, one first determines the three-dimensional structure of a protein of interest by x-ray crystallography, by computer modeling or most typically, by a combination of approaches. Useful information regarding the structure of a polypeptide may also be gained by modeling based on the structure of homologous proteins. An example of rational drug design is the development of HIV protease inhibitors (Erickson et al., *Science* 249: 527-533, 1990). In addition, target molecules may be analyzed by an alanine scan (Wells, *Methods Enzymol.* 202: 2699-2705, 1991). In this technique, an amino acid residue is replaced by Ala and its effect on the peptide's activity is determined. Each of the amino acid residues of the peptide is analyzed in this manner to determine the important regions of the peptide.

It is also possible to isolate a target-specific antibody, selected by a functional assay and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Two-hybrid screening is also useful in identifying other members of a biochemical or genetic pathway associated with a target. Two-hybrid screening conveniently uses *Saccharomyces cerevisiae* and *Saccharomyces pombe*. Target interactions and screens for inhibitors can be carried out using the yeast two-hybrid system, which takes advantage of transcriptional factors that are composed of two physically separable, functional domains. The most commonly used is the yeast GAL4 transcriptional activator consisting of a DNA binding domain and a transcriptional activation domain. Two different cloning vectors are used to generate separate fusions of the GAL4 domains to genes encoding potential binding proteins. The fusion proteins are co-expressed, targeted to the nucleus and if interactions occur, activation of a reporter gene (e.g. lacZ) produces a detectable phenotype. In the present case, for example, *S. cerevisiae* is co-transformed with a library or vector expressing a cDNA GAL4 activation domain fusion and a vector expressing a holocyclotxin-GAL4 binding domain fusion. If lacZ is used as the reporter gene, co-expression of the fusion proteins will produce a blue color. Small molecules or other candidate compounds which interact with a target will result in loss of colour of the cells. Reference may be made to the yeast two-hybrid systems as disclosed by Munder et al. (*Appl. Microbiol. Biotechnol.* 52: 311-320, 1999) and Young et al (*Nat. Biotechnol.* 16: 946-950, 1998). Molecules thus identified by this system are then re-tested in animal cells.

The present invention further contemplates methods of screening for drugs comprising, for example, contacting a candidate drug with a transcription factor. These molecules are referred to herein as "targets", "a target" or "target molecule". The screening procedure includes assaying for the presence of a complex between the drug and the target. One form of assay involves competitive binding assays. In such competitive binding assays, the target is typically labeled. Free target is separated from any putative complex and the amount of free (i.e. uncomplexed) label is a measure of the binding of the agent being tested to target molecule. One may also measure the amount of bound, rather than free, target. It is also possible to label the compound rather than the target and to measure the amount of compound binding to target in the presence and in the absence of the drug being tested.

Another technique for drug screening provides high throughput screening for compounds having suitable binding affinity to a target and is described in detail in Geysen (International Patent Publication No. WO 84/03564). Briefly stated, large numbers of different small peptide test compounds are synthesized on a solid substrate, such as plastic pins or some other surface. The peptide test compounds are reacted with a target and washed. Bound target molecule is then detected by methods well known in the art. This method may be adapted for screening for non-peptide, chemical entities. This aspect, therefore, extends to combinatorial approaches to screening for target antagonists or agonists.

Purified target can be coated directly onto plates for use in the aforementioned drug screening techniques. However, non-neutralizing antibodies to the target may also be used to immobilize the target on the solid phase.

The present invention also contemplates the use of competitive drug screening assays in which neutralizing antibodies capable of specifically binding the target compete with a test compound for binding to the target or fragments thereof. In this manner, the antibodies can be used to detect the presence of any peptide which shares one or more antigenic determinants of the target.

The present invention also provides a method for identifying a M-GRH, said method comprising screening a nucleotide database and identifying a nucleotide sequence having at least 60% similarity to SEQ ID NO:17 or SEQ ID NO:34 or SEQ ID NO:36 or SEQ ID NO:38 after optimal alignment.

Reference to a "nucleotide database" includes screening an existing genomic or cDNA or mRNA database or screening for a target nucleic acid molecule in a mammalian cell such as using oligonucleotide probes or primers, sequencing the target molecule and comparing the sequence to SEQ ID NO:17 or SEQ ID NO:34 or SEQ ID NO:36 or SEQ ID NO:38.

In an alternative method, a database of mammalian protein sequences is screened for an amino acid sequence having at least 60% similarity to the amino acid sequence encoded by SEQ ID NO:17 or SEQ ID NO:34 or SEQ ID NO:36 or SEQ ID NO:38. Again, a "database" includes a de novo protein sequence isolated and identified on a transcription factor isolated form a mammalian cell.

In yet another alternative, a M-grh or its protein product is deemed one which has at least about 60% similarity at the nucleotide level to SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or at the amino acid level to SEQ ID NO:2, SEQ ID NO:4, SEQ ID NO:6, SEQ ID NO:8, SEQ ID NO:10, SEQ ID NO:12, SEQ ID NO:14 or SEQ ID NO:15.

Still yet another aspect of the present invention provides a means of identifying a nucleotide sequence likely to encode an M-GRH transcription factor, said method comprising interrogating a mammalian genome database conceptually translated into different reading frames with an amino acid sequence defining *Drosophila* GRH or any one of SEQ ID NO:2, SEQ ID NO:4, SEQ ID NO:6, SEQ ID NO:8, SEQ ID NO:10, SEQ ID NO:12, SEQ ID NO:14 and SEQ ID NO:16 and identifying a nucleotide sequence corresponding to an amino acid sequence having at least about 60% similarity to *Drosophila* GRH or to any one of SEQ ID NO:2, SEQ ID NO:4, SEQ ID NO:6, SEQ ID NO:8, SEQ ID NO:10, SEQ ID NO:12, SEQ ID NO:14 and SEQ ID NO:16.

Preferably, the genome is conceptually translated into from about 3 to about 6 reading frames and more preferably six reading frames.

It is proposed in accordance with the present invention that the M-GRH transcription factors are involved in the modulation of expression of a number of genes including developmentally regulated genes. Accordingly, aberrations in the M-GRH or M-grh molecules are proposed to cause over or under expression of particular genes leading to a potentially unwanted phenotype. The phenotype may manifest itself pre- or post-natally. A pre-natal manifestation includes at the embryo or fetus stage. Conditions contemplated include developmentally-determined disease conditions such as poor brain development, poor muscle or bone development, aberrations in facial or cranial structures, malformed spinal structures, predispositions to a range of cancers including melanomas and immunological disorders.

Accordingly, another aspect of the present invention contemplates a method for detecting an aberrant phenotype or a propensity for an aberrant phenotype to develop, said method comprising screening for a variation in a nucleotide sequence encoding a mammalian MGR, BOM and/or SOM or their homologs.

Reference herein to "MGR", "BOM" and "SOM" includes murine and human forms of these molecules such as human MGR p49 (SEQ ID NO:2), human MGR p70 (SEQ ID NO:4), human BOM (SEQ ID NO:6), human SOM (SEQ ID NO:8), murine MGR p61 (SEQ ID NO:10), murine MGR p70 (SEQ ID NO:12), murine BOM (SEQ ID NO:14) and murine SOM (SEQ ID NO:16).

A homolog of MGR, BOM and SOM is as herein defined including a molecule having at least about 60% amino acid sequence similarity to MGR, BOM or SOM or at least about 60% nucleic acid similarity to mgr, bom or som or a nucleic acid molecule capable of hybridizing to the coding strands of mgr, born or som or complementary forms thereof under low stringency conditions.

Aberrations may also be detectable at the amino acid level when the mammalian homologs of *Drosophila* grh encode protein transcription factors.

Accordingly, another aspect of the present invention contemplates a method for detecting an aberrant phenotype or a propensity for an aberrant phenotype to develop, said method comprising screening for a variation in an amino acid sequence encoding MGR, BOM and/or SOM or their homologs.

As above, reference to MGR, BOM and SOM include amino acid sequences defining human MGR p49 (SEQ ID NO:2), human MGR p70 (SEQ ID NO:4), human BOM SEQ ID NO:6), human SOM (SEQ ID NO:8), murine MGR p61 (SEQ ID NO:10), murine MGR p70 (SEQ ID NO:12), murine BOM (SEQ ID NO:14) and murine SOM (SEQ ID NO:16).

As stated above, the mammalian transcription factors and their genetic sequences have a range of diagnostic and therapeutic utilities. The detection of an aberrant transcription factor or a nucleotide sequence encoding an aberrant transcription factor is indicative of a disease condition including a degenerative or developmental disease condition.

Any number of methods may be employed to detect aberrant transcription factors or their genetic sequences. Immunological testing is one particular method. Accordingly, the present invention extends to antibodies and other immunological agents directed to or preferably specific for the mammalian transcription factors or a fragment thereof. The antibodies may be monoclonal or polyclonal or may comprise Fab fragments or synthetic forms.

Specific antibodies can be used to screen for the subject mammalian transcription factors and/or their fragments. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies referred to above. Both the first and second antibodies may be used in detection assays or a first antibody may be used with a commercially available anti-immunoglobulin antibody. An antibody as contemplated herein includes any antibody specific to any region of the mammalian transcription factors.

Both polyclonal and monoclonal antibodies are obtainable by immunization with mammalian transcription factors or antigenic fragments thereof and either type is utilizable for immunoassays. The methods of obtaining both types of sera are well known in the art. Polyclonal sera are less preferred but are relatively easily prepared by injection of a suitable laboratory animal with an effective amount of subject polypeptide, or antigenic parts thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates, therefore, a method for detecting a mammalian transcription factor or fragment thereof in a biological sample from a subject, said method comprising contacting said biological sample with an antibody specific for said mammalian transcription factor or fragment thereof or its derivatives or homologs for a time and under conditions sufficient for an antibody-polypeptide complex to form, and then detecting said complex.

A biological sample includes a cell extract.

Reference to a "mammalian transcription factor" is considered to be a reference to a homolog of *Drosophila* grh, i.e. M-GRH.

The presence of the instant mammalian transcription factors or their fragments may be detected in a number of ways such as by Western blotting and ELISA procedures. A wide range of immunoassay techniques are available as can be seen by reference to U.S. Pat. Nos. 4,016,043, 4,424,279 and 4,018,653.

Sandwich assays are among the most useful and commonly used assays and are favoured for use in the present invention. A number of variations of the sandwich assay technique exist, and all are intended to be encompassed by the present invention. Briefly, in a typical forward assay, an unlabeled antibody is immobilized on a solid substrate and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labeled antibody are added simultaneously to the bound antibody. These techniques are well known to those skilled in the art, including any minor variations as will be readily apparent. In accordance with the present invention the sample is one which might contain a subject transcription factor including by tissue biopsy, blood, synovial fluid and/or lymph. The sample is, therefore, generally a biological sample comprising biological fluid. The transcription factor is likely to be in blood or other fluid in the case where cell apoptosis is occurring.

In the typical forward sandwich assay, a first antibody having specificity for the instant polypeptide or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or where more convenient, overnight) and under suitable conditions (e.g. for about 20° C. to about 40° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labeled with a reporter molecule. Depending on the amount of target and the strength of the reporter molecule signal, a bound target may be detectable by direct labelling with the antibody. Alternatively, a second labeled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent labeled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect RNA expression products of a genetic sequence encoding a mammalian transcription factor. The genetic assays may also be able to detect nucleotide polymorphisms or other substitutions, additions and/or deletions in the nucleotide sequence of a mammalian transcription factor. Changes in levels of mammalian transcription factor expression such as following mutations in the promoter or regulatory regions or loss of mammalian transcription factor activity following mutations in mammalian transcription factor nucleotides is proposed to be indicative of a disease condition or a propensity for a disease condition to develop. For example, a cell biopsy could be obtained and DNA or RNA extracted. Alternative methods which may be used alone or in conjunction with other methods include direct nucleotide sequencing or mutation scanning such as single stranded conformation polymorphms analysis (SSCP) as well as specific oligonucleotide hybridization, denaturing high performance liquid chromatography, first nucleotide change (FNC) amongst others.

The present invention extends to polymorphisms which in the M-grh genes leads to healthy or abnormal phenotypes.

The present invention further contemplates kits to facilitate the rapid detection of mammalian transcription factors or their fragments in a subject's biological fluid.

Again, a biological fluid includes a cell extract such as a DNA/RNA extract.

Still yet another aspect of the present invention contemplates genomic sequences including gene sequences encoding a mammalian transcription factor as well as regulatory regions such as promoters, terminators and transcription/translation enhancer regions associated with the gene encoding a mammalian transcription factor.

The term "gene" is used in its broadest sense and includes cDNA corresponding to the exons of a gene. Accordingly, reference herein to a "gene" is to be taken to include:-

(i) a classical genomic gene consisting of transcriptional and/or translational regulatory sequences and/or a coding region and/or non-translated sequences (i.e. introns, 5'- and 3'-untranslated sequences); or (ii) mRNA or cDNA corresponding to the coding regions (i.e. exons) and 5'- and 3'-untranslated sequences of the gene.

The term "gene" is also used to describe synthetic or fusion molecules encoding all or part of an expression product. In particular embodiments, the term "nucleic acid molecule" and "gene" may be used interchangeably.

In a particularly useful embodiment, the present invention provides a promoter for the mammalian transcription factor gene. The identification of the promoter permits developmentally-regulated expression of particular genetic sequences. The latter would include a range of therapeutic molecules such as cytokines, growth factors, antibiotics or other molecules to assist in the treatment of particular disease conditions.

Accordingly, another aspect of the present invention provides a M-grh specific promoter or functional derivative or homolog thereof, said promoter in situ operably linked to a nucleotide sequence comprising any one of SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or their complementary forms or a nucleotide sequence having at least about 60% similarity to SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or their complementary forms or a nucleotide sequence capable of hybridizing to SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or their complementary forms tinder low stringency conditions.

The promoter is conveniently resident in a vector which comprises unique restriction sites to facilitate the introduction of genetic sequences operably linked to the promoter.

All such constructs are useful in order to produce recombinant M-GRH molecules and/or in gene therapy protocols.

The present invention further contemplates a genetically modified animal.

More particularly, the present invention provides an animal model useful for screening for agents capable of ameliorating the effects of an aberrant M-GRH or M-grh gene. In one embodiment, the animal model produces low amounts of M-grh. Such an animal would have a predisposition for a range of diseases including developmentally regulated diseases. The animal model is useful for screening for agents which ameliorate such conditions.

Accordingly, another aspect of the present invention provides a genetically modified animal wherein said animal produces low amounts of M-grh relative to a non-genetically modified animal of the same species. Reference to "low amounts" includes zero amounts or up to about 10% lower than normalized amounts.

Preferably, the genetically modified animal is a mouse, rat, guinea pig, rabbit, pig, sheep or goat. More preferably, the genetically modified animal is a mouse or rat. Most preferably, the genetically modified animal is a mouse.

Accordingly, a preferred aspect of the present invention provides a genetically modified mouse wherein said mouse produces low amounts of M-grh relative to a non-genetically modified mouse of the same strain.

The animal model contemplated by the present invention comprises, therefore, an animal which is substantially incapable of producing a M-grh. Generally, but not exclusively, such an animal is referred to as a homozygous or heterozygous M-grh-knockout animal.

The animal models of the present invention may be in the form of the animals or may be, for example, in the form of embryos for transplantation. The embryos are preferably maintained in a frozen state and may optionally be sold with instructions for use.

The genetically modified animals may also produce larger amounts of M-GRH For example, over expression of normal M-grh or mutant M-grh may produce dominant negative effects and may become useful disease models.

Accordingly, another aspect of the present invention is directed to a genetically modified animal over-expressing genetic sequences encoding M-grh.

A genetically modified animal includes a transgenic animal, or a "knock-out" or "knock-in" animal.

Yet another aspect of the present invention provides a targeting vector useful for inactivating a gene encoding M-GRH, said targeting vector comprising two segments of genetic material encoding said M-GRH flanking a positive selectable marker wherein when said targeting vector is transfected into embryonic stem (ES) cells and the marker selected, an ES cell is generated in which the gene encoding said M-GDH is inactivated by homologous recombination.

Preferably, the ES cells, are from mice, rats, guinea pigs, pigs, sheep or goats. Most preferably, the ES cells are from mice.

Still yet another aspect of the present invention is directed to the use of a targeting vector as defined above in the manufacture of a genetically modified animal substantially incapable of producing M-GRH.

Even still another aspect of the present invention is directed to the use of a targeting vector as defined above in the manufacture of a genetically modified mouse substantially incapable of producing M-GRH.

Preferably, the vector is DNA. A selectable marker in the targeting vector allows for selection of targeted cells that have stably incorporated the targeting DNA. This is especially useful when employing relatively low efficiency transformation techniques such as electroporation, calcium phosphate precipitation and liposome fusion where typically fewer than 1 in 1000 cells will have stably incorporated the exogenous DNA. Using high efficiency methods, such as microinjection into nuclei, typically from 5-25% of the cells will have incorporated the targeting DNA; and it is, therefore, feasible to screen the targeted cells directly without the necessity of first selecting for stable integration of a selectable marker. Either isogenic or non-isogenic DNA may be employed.

Examples of selectable markers include genes conferring resistance to compounds such as antibiotics, genes conferring the ability to grow on selected substrates, genes encoding proteins that produce detectable signals such as luminescence. A wide variety of such markers are known and available, including, for example, antibiotic resistance genes such as the neomycin resistance gene (neo) and the hygromycin resistance gene (hyg). Selectable markers also include genes conferring the ability to grow on certain media substrates such as the tk gene (thymidine kinase) or the hprt gene (hypoxanthine phosphoribosyltransferase) which confer the ability to grow on HAT medium (hypoxanthine, aminopterin and thymidine); and the bacterial gpt gene (guanine/xanthine phosphoribosyltransferase) which allows growth on MAX medium (mycophenolic acid, adenine and xanthine). Other selectable markers for use in mammalian cells and plasmids carrying a variety of selectable markers are described in Sambrook et al. *Molecular Cloning—A Laboratory Manual*, Cold Spring Harbour, N.Y., USA, 1990.

The preferred location of the marker gene in the targeting construct will depend on the aim of the gene targeting. For example, if the aim is to disrupt target gene expression, then the selectable marker can be cloned into targeting DNA corresponding to coding sequence in the target DNA. Alternatively, if the aim is to express an altered product from the target gene, such as a protein with an amino acid substitution, then the coding sequence can be modified to code for the substitution, and the selectable marker can be placed outside of the coding region, for example, in a nearby intron.

The selectable marker may depend on its own promoter for expression and the marker gene may be derived from a very different organism than the organism being targeted (e.g. prokaryotic marker genes used in targeting mammalian cells). However, it is preferable to replace the original promoter with transcriptional machinery known to function in the recipient cells. A large number of transcriptional initiation regions are available for such purposes including, for example, metallothionein promoters, thymidine kinase promoters, β-actin promoters, immunoglobulin promoters, SV40 promoters and human cytomegalovirus promoters. A widely used example is the pSV2-neo plasmid which has the bacterial neomycin phosphotransferase gene under control of the SV40 early promoter and confers in mammalian cells resistance to G418 (an antibiotic related to neomycin). A number of other variations may be employed to enhance expression of the selectable markers in animal cells, such as the addition of a poly(A) sequence and the addition of synthetic translation initiation sequences. Both constitutive and inducible promoters may be used.

The DNA is preferably modified by homologous recombination. The target DNA can be in any organelle of the animal cell including the nucleus and mitochondria and can be an intact gene, an exon or intron, a regulatory sequence or any region between genes.

Homologous DNA is a DNA sequence that is at least 70% identical with a reference DNA sequence. An indication that two sequences are homologous is that they will hybridize with each other under stringent conditions (Sambrook et al., 1990, sup) a).

The genetically modified animals contemplated herein include "knock out" or "knock in" animals or genetic sequencing carrying one or more nucleotide additions, deletions, substitutions and/or insertions. They are useful in a range of applications including the development of medical assessment systems such as to monitor particle physiological conditions including genetic defects such as but not limited to spinabifida in humans. The medical assessment systems are also useful as a model for wound healing and clsoure and for agents which modulate same.

The present invention further contemplates conditional genetically modified animals, such as those produced using recombination methods that are standard in the art. Bacteriophage P1 Cre recombinase and flp recombinase from yeast plasmids are two non-limiting examples of site-specific DNA recombinase enzymes that leave DNA at specific target sites (box P sites for Cre recombinase and fit sites for flp recombinase).

The present invention further contemplates co-suppression (i.e. sense suppression) and antisense suppression to down-regulate expression of M-grh This would generally occur in a target test animal such as to generate a disease model.

In addition to providing a diagnostic capability as described above, the isolated nucleic acid molecules of the present invention may also provide a therapeutic capability by being used to correct or complement an abnormality detected in a subject. To deliver the appropriate sequence to a recipient cell or tissue of a subject, an isolated nucleic acid molecule of the present invention may be cloned into a suitable genetic construct such as a suitable vector.

Accordingly, a further aspect of the present invention contemplates a genetic construct comprising a nucleotide sequence encoding an M-grh selected from SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or a variant thereof or a nucleotide sequence having at least 60% similarity to one or more of SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or a variant thereof or a nucleotide sequence capable of hybridizing to SEQ ID NO:1, SEQ ID. NO:3, SEQ ID NO:5, SEQ ID NO:7, SEQ ID NO:9, SEQ ID NO:11, SEQ ID NO:13 or SEQ ID NO:15 under low stringency conditions or a variant thereof or a complementary form thereof.

A "vector" is a polynucleotide molecule, preferably a DNA molecule derived, for example, from a plasmid, bacteriophage, or plant virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e. a vector that exists as an extra-chromosomal entity, the replication of which is independent of chromosomal replication. Examples include a linear or closed circular plasmid, an extra-chromosomal element, a mini-chromosome, or an artificial chromosome. The vector may also contain a means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon.

Vectors suitable for gene therapy applications are well known in the art. The choice of the vector will typically depend on the compatibility of the vector with the host cell into which it is to be introduced. The vector may also include an additional genetic construct comprising a selection marker such as an antibiotic resistance gene that can be used for selection of suitable transformants. Examples of such resistance genes are known to those skilled in the art and include the nptII gene that confers resistance to the antibiotics kanamycin, and G418 (Geneticin®) and the hph gene which confer resistance to the antibiotic hygromycin B.

Accordingly, in a related embodiment, the present invention provides a genetic construct comprising a promoter or functional equivalent thereof operably linked to a nucleotide sequence of the invention.

Reference herein to a "promoter" is to be taken in its broadest context and includes the transcriptional regulatory sequences of a classical genomic gene, which is required for accurate transcription initiation, with or without a CCAAT box sequence and additional regulatory elements (i.e. upstream activating sequences, enhancers and silencers), which alter gene expression in response to developmental and/or external stimuli, or in a tissue-specific manner. A promoter is usually, but not necessarily, positioned upstream (5') of a gene region, the expression of which it regulates. Furthermore, the regulatory elements comprising a promoter are usually positioned within 2 kb of the start site of transcription of the gene. As is known in the art, some variation in this distance can be accommodated without loss of promoter function.

The selection of an appropriate promoter sequence to regulate expression of a transcription factor encoded by an isolated nucleic acid molecule of the present invention is an important consideration. Examples of suitable promoters include viral, fungal, bacterial, animal and plant derived promoters capable of functioning in eukaryotic animal cells and, especially, human cells. The promoter may regulate the expression of the nucleic acid molecule differentially with respect to the cell, tissue or organ in which expression occurs, or with respect to the developmental stage at which expression occurs.

Preferably, the promoter is capable of regulating expression of a nucleic acid molecule in a eukaryotic cell, tissue or organ, at least during the period of time over which the regulated gene is expressed therein, and more preferably also immediately preceding the commencement of detectable expression of the regulated gene in said cell, tissue or organ.

Particularly preferred promoters for use with the nucleic acid molecules of the present invention include the bacteriophage T7 promoter, bacteriophage T3 promoter, SP6 promoter, lac operator-promoter, tac promoter, SV40 late promoter, SV40 early promoter, RSV-LTR promoter, CMV IE promoter, CaMV 35S promoter. SCSV promoter, SCBV promoter and the like. Those skilled in the art will readily be aware of additional promoter sequences other than those specifically described.

In the present context, the terms "in operable connection with" or "operably linked" or similar shall be taken to indicate that expression of the nucleic acid molecule is under the control of the promoter sequence, with which it is spatially connected, in a cell, tissue, organ or whole organism.

The genetic construct of the present invention may also comprise a 3' non-translated sequence. A 3' non-translated sequence refers to that portion of a gene comprising a DNA segment that contains a polyadenylation signal and any other regulatory signals capable of effecting in RNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon.

Accordingly, a genetic construct comprising a nucleic acid molecule of the present invention, operably linked to a promoter, may be cloned into a suitable vector for delivery to a cell or tissue in which regulation is faulty, malfunctioning or non-existent, in order to rectify and/or provide the appropriate regulation. Vectors comprising appropriate genetic constructs may be delivered into target eukaryotic cells by a number of different means well known to those skilled in the art of molecular biology.

The present invention further contemplates the use of an M-GRH or M-grh in the manufacture of a medicament for the treatment of a disease condition in a mammal such as a human.

The present invention is further directed to promoters and 3'- and 5'-regulatory regions associated with genomic forms of M-grh genes. These regions can be readily identified by, for example, chromosome walking using M-grh nucleic acid molecules or probes or primers therefrom.

A further aspect of the present invention relates to the use of the invention in relation to the treatment and/or prophylaxis of disease conditions. Without limiting the present invention to any one theory or mode of action, the broad range of cellular functional activities which are regulated by transcription factors renders the regulation of transcription factor function an integral component of every aspect of both healthy and disease state physiological processes. Accordingly, the method of the present invention provides a valuable tool for modulating aberrant or otherwise unwanted cellular functional activity which is regulated via transcription factors.

Accordingly, another aspect of the present invention is directed to a method for the treatment and/or prophylaxis of a condition in a subject, which condition is characterised by aberrant, unwanted or otherwise inappropriate cellular activity, said method comprising administering to said mammal an effective amount of an agent for a time and under conditions sufficient to modulate transcription factor function.

The terms "agent", "compound", "active agent", "pharmacologically active agent", "medicament", "active" and "drug" are used interchangeably herein to refer to a chemical compound that induces a desired pharmacological and/or physiological effect. The terms also encompass pharmaceutically acceptable and pharmacologically active ingredients of those active agents specifically mentioned herein including but not limited to salts, esters, amides, prodrugs, active metabolites, analogs and the like. When the terms "agent", "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc. The term "compound" is not to be construed as a chemical compound only but extends to peptides, polypeptides and proteins as well as genetic molecules such as RNA, DNA and chemical analogs thereof as well as RNAi- or siRNA-type molecules or complexes comprising same. In accordance with the previous aspects of the present invention, the agent preferably comprises a transcription factor or genetic molecules encoding same or derivative, analogue, chemical equivalent or mimetic thereof.

"Subject" as used herein refers to an animal, preferably a mammal and more preferably human who can benefit from the pharmaceutical formulations and methods of the present invention. There is no limitation on the type of animal that could benefit from the presently described pharmaceutical formulations and methods. A patient regardless of whether a human or non-human animal may be referred to as an individual, subject, animal, host or recipient.

The preferred animals are humans or other primates, livestock animals, laboratory test animals, companion animals or captive wild animals.

Examples of laboratory test animals include mice, rats, rabbits, guinea pigs and hamsters. Rabbits and rodent animals, such as rats and mice, provide a convenient test system or animal model. Livestock animals include sheep, cows, pigs, goats, horses and donkeys. Non-mammalian animals such as zebrafish and amphibians (including cane toads) are also contemplated An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

The present invention further contemplates a combination of therapies, such as the administration of the agent together with subjection of the mammal to other agents, drugs or treatments which may be useful in relation to the treatment of the subject condition such as spina bifida and anencephaly.

Administration of the modulatory agent, in the form of a pharmaceutical composition, may be performed by any convenient means. The modulatory agent of the pharmaceutical composition is contemplated to exhibit therapeutic activity when administered in an amount which depends on the particular case. The variation depends, for example, on the human or animal and the modulatory agent chosen. A broad range of doses may be applicable. Considering a patient, for example, from about 0.1 mg, 0.2 mg, 0.3 mg, 0.4 mg, 0.5 mg, 0.6 mg, 0.7 mg, 0.5 mg. 0.9 mg to about 1 mg of modulatory agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The modulatory agent may be administered in a convenient manner such as by the oral, intravenous (where water soluble), intraperitoneal, intramuscular, subcutaneous, intradermal or suppository routes or implanting (e.g. using slow release molecules). The modulatory agent may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

Routes of administration include, but are not limited to, respiratorally, intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip patch and implant.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. For example, the subject agent may be administered together with an agonistic agent in order to enhance its effects. By "sequential" administration is meant a time difference of from seconds, minutes, hours or days between the administration of the two types of molecules. These molecules may be administered in any order.

Another aspect of the present invention contemplates the use of an agent, as hereinbefore defined, in the manufacture of medicament for the treatment of a condition in a subject, which condition is characterised by aberrant, unwanted or otherwise inappropriate cellular activity, wherein said agent modulates transcription factor function.

In yet another further aspect, the present invention contemplates a pharmaceutical composition comprising the modulatory agent as hereinbefore defined together with one or more pharmaceutically acceptable carriers and/or diluents. These agents are referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Antisense polynucleotide sequences are another useful example of a therapeutic agent which can prevent or diminish the expression of the transcription factor genetic sequences, as will be appreciated by those skilled in the art. Polynucleotide vectors, for example, containing all or a portion of the M-grh sequences or other sequences from an M-grh region (particularly those flanking an M-grh gene locus) may be placed under the control of a promoter in an antisense orientation and introduced into a cell. Expression of such an antisense construct within a cell will interfere with gene transcription and/or translation. Furthermore, co-suppression and mechanisms to induce RNAi (i.e. siRNA) may also be employed. Such techniques may be sueful to inhibit genes which positively promote M-grh gene expression. Alternatively, antisense or sense molecules may be directly administered. In this latter embodiment, the antisense or sense molecules may be formulated in a composition and then administered by any number of means to target cells.

A variation on antisense and sense molecules involves the use of morpholinos, which are oligonucleotides composed of morpholine nucleotide derivatives and phosphorodiamidate linkages (for example, Summerton and Weller, linkages (for example, Summerton and Weller, *Antisense and Nucleic Acid Drug Development* 7: 187-195, 1997). Such compounds are injected into embryos and the effect of interference with mRNA is observed.

In one embodiment, the present invention employs compounds such as oligonucleotides and similar species for use in modulating the function or effect of nucleic acid molecules encoding an M-GRH transcription factor, i.e. the oligonucleotides induce transcriptional or post-transcriptional gene silencing. This is accomplished by providing oligonucleotides which specifically hybridize with one or more nucleic acid molecules encoding the transcription factor. As used herein, the terms "target nucleic acid" and "nucleic acid molecule encoding a transcription factor" have been used for convenience to encompass DNA encoding M-GRH, RNA (including pre-mRNA and mRNA or portions thereof) transcribed from such DNA, and also cDNA derived from such RNA. The hybridization of a compound of the subject invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of a M-grh gene. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e. under physiological conditions in the case of in vivo assays or therapeutic treatment, and under conditions in which assays are performed in the case of in vitro assays.

"Complementary" as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other.

Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals.

In the context of the subject invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Many of the preferred features described above are appropriate for sense nucleic acid molecules.

Another aspect of the present invention contemplates a method for the treatment or prophylaxis of an animal, said method comprising exposing stem cells in said animal to one or more agents comprising a transcription factor, or a genetic molecule encoding a transcription factor or derivative, analogue, chemical equivalent or mimetic thereof which facilitates the proliferation and/or differentiation and/or self-renewal of stem cells to facilitate repair, replacement or augmentation of particular tissue.

In a related embodiment, the present invention provides a method for the treatment or prophylaxis of an animal, said method comprising exposing stem cells and mature cells or cells developmentally in between in said animal to one or more agents which facilitate the proliferation and/or differentiation and/or self-renewal of stem cells and mature cells or of cells developmentally in between to facilitate repair, replacement or augmentation of particular tissue.

As indicated above, the term "animal" includes a human amongst a range of other animals including avian species. The agent may comprise a single molecule or a combination of two or more molecules in a synergistic combination, admixture or cocktail. When in combination, the agents may be administered or used simultaneously or used sequentially such as seconds, minutes, hours, days or weeks apart. As indicated further below, the agent including therapeutic agent of this aspect of the present invention may also be a multi-part pharmaceutical pack or composition with instructions for use.

Reference to "exposing" to stem cells includes the situation where an agent is introduced into the body of the animal or the agent is contacted to an internal or external surface of, for example, skin or an organ or is otherwise administered to a surface or sub-surface or internal region. Alternatively, stem cells are removed from the animal's body and exposed to the agent ex vivo to facilitate differentiation and/or proliferation and/or self-renewal (either ex vivo or in vivo) and then the cells are returned to the same or different individual. According to this aspect of the present invention, although it is preferred to administer a therapeutic agent to an animal subject (e.g. a human), part of the therapeutic protocol may occur ex vivo. For example, proliferation may occur in vivo and differentiation may occur in vivo. Alternatively, part proliferation and part differentiation may occur ex vivo and further facilitated in vivo by the administration of a therapeutic agent. Yet in a further alternative, proliferation occurs ex vivo and partial differentiation occurs in vitro but complete differentiation occurs in vivo. The terms "ex vitro" and "in vitro" are used interchangedly in this specification. In some circumstances, stem cells maintained in vitro may be used. Alternatively, ex vivo cells may first be genetically modified prior to re-introduction into a subject's body or a compatible counterpart.

Reference to "in vitro" or "ex vivo" means in tissue culture or in any situation outside the animal body. The term "in vitro" also means in situ and means treatment inside an animal body.

A mature cell in this context also includes a committed cell. This aspect of the present invention also extends to fetal cells such as ES cells or EG cells.

The entire repertoire of stem cells may be targeted by the therapeutic agent or one or more sub-populations may be induced to proliferate and/or differentiate. This is the difference between a generic agent or a specific agent. Cell sub-populations contemplated by the present invention include cells from the brain (e.g. adult neural stem cells, neurons, astrocytes), epidermis (e.g. keratinocyte stem cells, keratinocyte transient amplifying cells, keratinocyte post-mitotic differentiating cells, melanocyte stem cells, melanocytes), embryos (e.g. ES or EG cells), skin (e.g. foreskin fibroblasts), pancreas (e.g. pancreatic islet cells, pancreatic β cells), kidney (e.g. adult renal stem cells, embryonic renal epithelial stem cells, kidney epithelial cells), liver (e.g. hepatocytes, bile duct epithelial cells, embryonic endodermal stem cells, adult hepatocyte stem cells), breast (e.g. mammary epithelial stem cells), lung (e.g. bone marrow-derived stem cells, lung fibroblasts, bronchial epithelial cells, alveolar type II pneumocytes), muscle (e.g. skeletal muscle stem cells [satellite cells]), heart (e.g. cardiomyoctes, bone marrow mesenchymal stem cells), eye (e.g. limbal stem cells, corneal epithelial cells), bone (e.g. mesenchymal stem cells, osteoblasts [precursor of mesenchymal stem cells], peripheral blood mononuclear progenitor cells [hematopoietic stem cells], osteoclasts), spleen (e.g. splenocytes) and cells from the immune system (e.g. CD34$^+$ stem cells. CD11c$^+$ cells, CD11c$^-$ cells, CD4$^+$ T-cells, CD8$^+$ T-cells, NK cells, monocytes, macrophages, dendritic cells and β-cells.

Whilst some of the above-listed cells are "mature" cells, they nevertheless may participate in a repair, regeneration or augmentation process by being selectively proliferated or used to "hone" in on particular tissue in need of treatment. Accordingly, the present invention is not to be interpreted as excluding the participation of mature cell types in the repair, regeneration and/or augmentation process as well as any other cell at a developmental stage between an ES cell and a mature cell.

Accordingly, another aspect of the present invention contemplates a method for tissue repair, regeneration and/or augmentation in an animal, said method comprising administering to said animal an agent or a combination of two or more agents, which agents promote or otherwise facilitate the proliferation and/or differentiation and/or self-renewal of a cell type selected from the listing comprising adult neural stem cells, neurons, astrocytes, keratinocyte stem cells, keratinocyte transient amplifying cells, keratinocyte post-mitotic differentiating cells, melanocyte stem cells, melanocytes, embryonic stem cells, embryonic germ cells, foreskin fibroblasts, pancreatic islet cells, pancreatic β-cells, adult renal stem cells, embryonic renal epithelial stem cells, kidney epithelial cells, hepatocytes, bile duct epithelial cells, embryonic endodermal stem cells, adult hepatocyte stem cells, mammary epithelial stem cells, bone marrow-derived stem cells, lung fibroblasts, bronchial epithelial cells, alveolar type II pneumocytes, skeletal muscle stem cells [satellite cells], cardiomyoctes, bone marrow mesenchymal stem cells, limbal stem cells, corneal epithelial cells, mesenchymal stem cells, osteoblasts [precursor of mesenchymal stem cells], peripheral blood mononuclear progenitor cells [hematopoietic stem cells], osteoclasts or splenocytes, said agents being administered for a time and under conditions sufficient to promote tissue repair, augmentation and/or regeneration.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features. It is also to be understood that unless stated otherwise, the subject invention is not limited to specific formulation components, manufacturing methods, dosage regimes, or the like, as such may vary.

The present invention is further described by the following non-limiting Examples.

EXAMPLE 1

Polymerase Chain Reaction

For RT-PCR, first strand cDNA was prepared from 2 μg of mRNA from primary tissues using random hexamers. Each cDNA sample was appropriately diluted to give similar amplification of S14 RNA under the same PCR conditions. The primer sequences are detailed below. The PCR conditions were 94° C. for 2 min followed by 35 cycles of 94° C. for 30 sec, 60° C. for 30 sec and 72° C. for 45 sec with a final extension at 72° C. for 5 min. All PCR products were electrophoresed on 1.5% w/v agarose gels, transferred to nitrocellulose and analyzed by Southern blot using $^{32}$P-radiolabeled internal oligonucleotides as probes. Membranes were then autoradiographed for 2 hr at −70° C.

The following primers were used to amplify probes for cDNA library screening and for RT-PCR:—

```
human p49 mgr
5'-GAAGTCTTTGATGCCCTGATG-3'      [SEQ ID NO:19]

5'-AACCCATTCCCTCGACATAGA-3'      [SEQ ID NO:20]

human p70 mgr
5-AGCGCGATGACACAGGAGTA-3'        [SEQ ID NO:21]

5'-CGTTGCTATGGAGACAGTGA-3'       [SEQ ID NO:22]

human bom
5'-CCGTTTAACAAGGACACTGC-3'       [SEQ ID NO:23]

5'-CTGGAAGCCACCAAATCTCT-3'       [SEQ ID NO:24]

murine p70 mgr
5'-AGCGCGATGACACAGGAGTA-3'       [SEQ ID NO:25]

5'-AGTGCCAGAGCTGAACTGAT-3'       [SEQ ID NO:26]

murine p61 mgr
5'-TCCATGGGTTCCTTGAGTTC-3'       [SEQ ID NO:27]

5'-AGTGCCAGAGCTGAACTGAT'-3'      [SEQ ID NO:28]

murine bom
5'-AAAGGGGAGCGAGTTCATTG-3'       [SEQ ID NO:29]

5'-AGAGCTCTCGGTGATGGATA-3'       [SEQ ID NO:30]
```

EXAMPLE 2

Cloning of Human and Murine mgr and bom

Human p49 mgr was cloned from a fetal brain cDNA phage library in the λZAP II vector (Stratagene). The cDNA encoding the longer human MGR isoform was amplified by RT-PCR from human kidney mRNA. The cDNA encoding the smaller murine isoform of MGR was cloned from a 17.5-day embryo phage library in the Lambda TripelEx vector (Clontech). The murine p70 cDNA was amplified from murine kidney mRNA by RT-PCR. The human bom cDNA was isolated form a placental phage library in the Lambda ZAP II vector (Stratagene) and the murine cDNA from an embryonic carcinoma cell line (P19) phage library in the Uni-ZAP XR vector (Stratagene). The murine MGR genomic locus was obtained from a 129SVJ phage library in the Lambda FIX II vector (Stratagene).

From similarity searches of GenBank databases, using the GRH protein sequence as a query, two murine expressed sequence tag (EST) entries were found from adult brain and ovary and one human EST entry from fetal brain that were not identical to any previously reported genes, yet shared high degrees of homology with each other and grh. These sequences were used to design murine and human primers and amplified probes from murine adult brain and ovary and human adult brain cDNA. The murine probe from adult brain cDNA was used in a screen of a day 17.5 mouse embryo cDNA library to obtain a full length clone of a gene referred to as mammalian grainyhead (mgr) due to its sequence and functional homology and similar expression pattern to that of the fly gene. The human probe derived from adult brain cDNA was used to obtain a full length cDNA clone from a human fetal brain library. Amino acid sequence comparison reveals this to be the human homolog of MGR with 94% identity at the amino acid level.

The murine probe derived from ovary cDNA was used in a screen of a murine teratocarcinoma cell line (P19) cDNA library to obtain a full length clone of a novel gene distinct from but highly related to mgr named brother-of-mgr (bom). The homology between mgr and bom suggests that mgr and bom arose through gene duplication.

The human homolog of bom was obtained using primers derived from a high throughput genome sequencing (HTGS) database entry with homology to murine bom. These were used to amplify a probe from a human placental cDNA library that was then screened to yield a full length human cDNA clone. Amino acid sequence comparison between murine and human BOM revealed 94% identity.

The sequence alignments between grh, mgr, bom, CP2 and LBP-1a revealed that mgr and bom are more closely related to grh than the previously identified homologs CP2 and LBP-1a (Table 4). This homology is particularly evident in the DNA binding and dimerization domains emphasizing the importance of protein/protein and protein/DNA interactions for the function of these factors.

TABLE 4

Amino acid sequence comparison of GRH-like genes and *Drosophila* grh

| Amino acid identity/ similarity to Grainyhead (%) | Overall | DNA-binding domain | Dimerization domain |
| --- | --- | --- | --- |
| MGR | 37/52 | 48/64 | 39/61 |
| BOM | 35/52 | 46/63 | 37/61 |
| SOM | 33/48 | 42/60 | 38/57 |
| CP2 | 26/42 | 32/52 | 29/47 |
| LBP-1a | 23/39 | 31/51 | 28/43 |

EXAMPLE 3

Identification of a Second Isoform of MGR

A striking feature of the alignment between MGR and BOM was the absence of an MGR domain corresponding to the first 93 amino acids of BOM. In view of the absence of tissue-specific isoforms of GRH, the EST database was searched for similar sequences using the 5' end of born as a query. A highly similar but non-identical sequence in an EST from murine kidney was located. The most 3' 30 nucleotides of this EST was identical to 30 nucleotides close to the 5' end of the mgr. Based on this, primers were designed from the kidney EST and mgr cDNA sequences and amplified a product of the predicted size from murine kidney cDNA. A similar product was also amplified from human kidney cDNA. Amino acid sequence analysis of the murine product revealed that it was highly homologous to the 5' end of the BOM protein and contiguous with the mgr open reading frame. However, it lacked the first 11 amino acids of a previously isolated mgr clone suggesting the presence of alternate splicing. To examine this, the murine mgr genomic locus was isolated and mapped. As shown in FIG. 1B, the first three coding exons in the locus are exclusive to the p70 isoform of mgr. In contrast, the shorter isoform of mgr's (p61) first coding exon is absent in the p70 isoform. Significantly, the 5' end of this exon lacks a splice acceptor site explaining its absence from the longer isoform. Instead, promoter sequences with a clear TATA box and CAP site are evident in close proximity to the translation initiation site (FIG. 1C). Subsequent mapping of the human genomic locus revealed that murine exon four was conserved in the human p70 protein but was absent in the 49 kDa isoform of MGR.

EXAMPLE 4

The First Three Exons of the mgr Genomic Locus Encode Transcriptional Activation Domain Although significant sequence homology exists between grh and the shorter mgr isoforms and p70 mgr, the isoleucine rich transcriptional activation domain identified in the fly protein is not conserved. Examination of the MGR-coding sequences failed to reveal a region homologous to other known transactivation domains. In view of the high degree of conservation of the first three coding exons of p70 mgr and bom, it was postulated that this could be the functional domain responsible for activation. To address this, the cDNA fragment encoding the first 93 amino acids of human p70 MGR (encoded by the first three exons) was subcloned in frame with the GAL4 DNA binding domain in a mammalian expression vector. The comparable region of BOM and the full length p49 MGR cDNA in frame into this vector was also cloned. These plasmids were co-transfected into the human 293T cell line with a reporter plasmid containing five concatamerized GAL4 DNA binding sites upstream of the chloramphenicol acetyltransferase (CAT) gene. The vector containing only the GAL4 DNA-BD or containing the VP16 activation domain fused to the GAL DNA-BD served as the negative and positive controls, respectively. As shown in FIG. 3, transcriptional activation of the CAT gene was observed with VP16, p70 MGR and the bom containing plasmids. No activation was observed with p49 mgr or the empty vector.

These findings confirm the presence of a highly conserved activation domain in the p70 mgr and bom that is lacking in p49 mgr.

EXAMPLE 5

MGR Binds to Known GRH Binding Sites

To determine the extent of the functional homology between GRH and MGR, it was initially examined whether the mammalian protein could bind to the well-characterized binding sites for the *Drosophila* factor in the Dopa decarboxylase and PCNA gene regulatory regions (Uv et al., *Mol. Cell. Biol.* 17: 6727-6735, 1997; Hayashi et al., *J. Biol. Chem.* 274: 35080-35088, 1999). Oligonucleotide probes encompassing these sites were incubated with nuclear extract from the human placental cell line JEG-3, which expresses both isoforms of MGR at RNA and protein level and analyzed in an electrophoretic mobility shift assay (EMSA).

EMSA were performed as previously described (Jane et al., *EMBO J.* 14: 97-105, 1995) with the following oligonucleotide probes (sense strand only given): *Drosophila* dopa decarboxylase promoter (Uv et al., 1997, supra)—GGTGGT-GCTCTAATAACCGGTTTCCAAGATGCGC (SEQ ID NO:31]; *Drosophila* PCNA promoter (Hayashi et al., 1999, supra)—GGGTAAAAAGTGTGAACAATCAAAC-CAGTTGGCA (SEQ ID NO:32]; human Engrailed-1 promoter (Logan et al., *Dev. Genet.* 13: 345-358, 1992)—GGA-CACACACCCAAACCCACACCCACCCACAAACACACAAACCGGCAGTTGATCG AACAACCACCCATCCTTCAATAACAGCAACCA [SEQ ID NO:33]. In some assays, anti-MGR polyclonal antiserum was included in the reaction mix. Two antisera were used for this purpose: antisera 611—raised against peptides common to the p70 and p49 MGR proteins in the dimerization domain; and antisera 67 raised against unique peptides in the $NH_2$-terminal domain of p70 MGR. Nuclear extract for these assays was obtained from the human placental cell line, JEG-3.

Figure 2A:
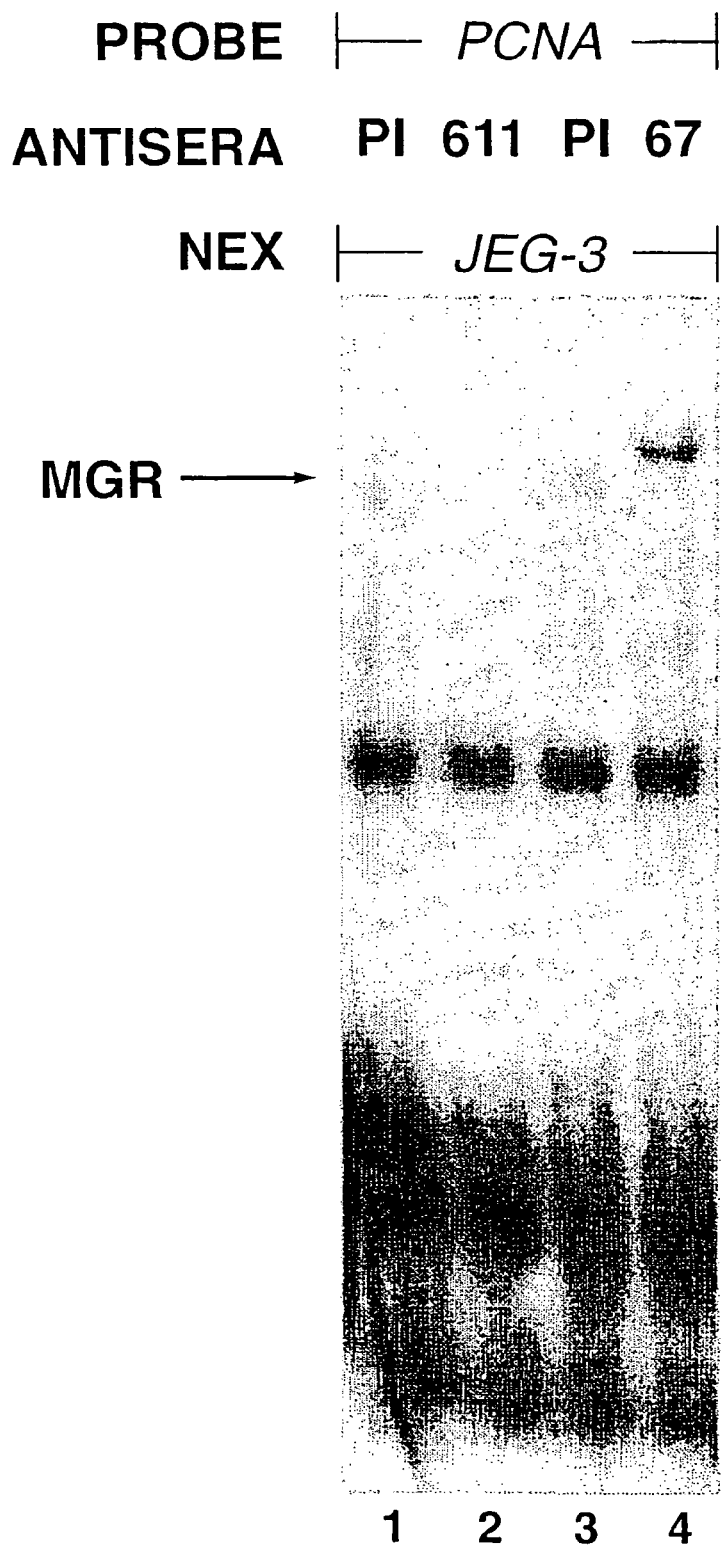
FIG. 2 is a photographic representation showing that p70 MGR binds to *Drosophila* gene regulatory sequences which bind grh. (A) p70 MGR binds to the *Drosophila* PCNA promoter. Nuclear extract from the JEG-3 cell line was studied in an EMSA with a PCNA promoter probe in the presence and absence of anti-MGR specific antisera. Antisera 611 was raised against peptides common to the p70 and p49 MGR proteins in the dimerization domain and antisera 67 was raised against unique peptides in the $NH_2$-terminal domain of p70 MGR. The migration of the MGR complex is shown in arrows. (B) p70 MGR binds to the *Drosophila* dopo decarboxylase promoter. Experimental conditions were as described for (A).
Figure 2B:
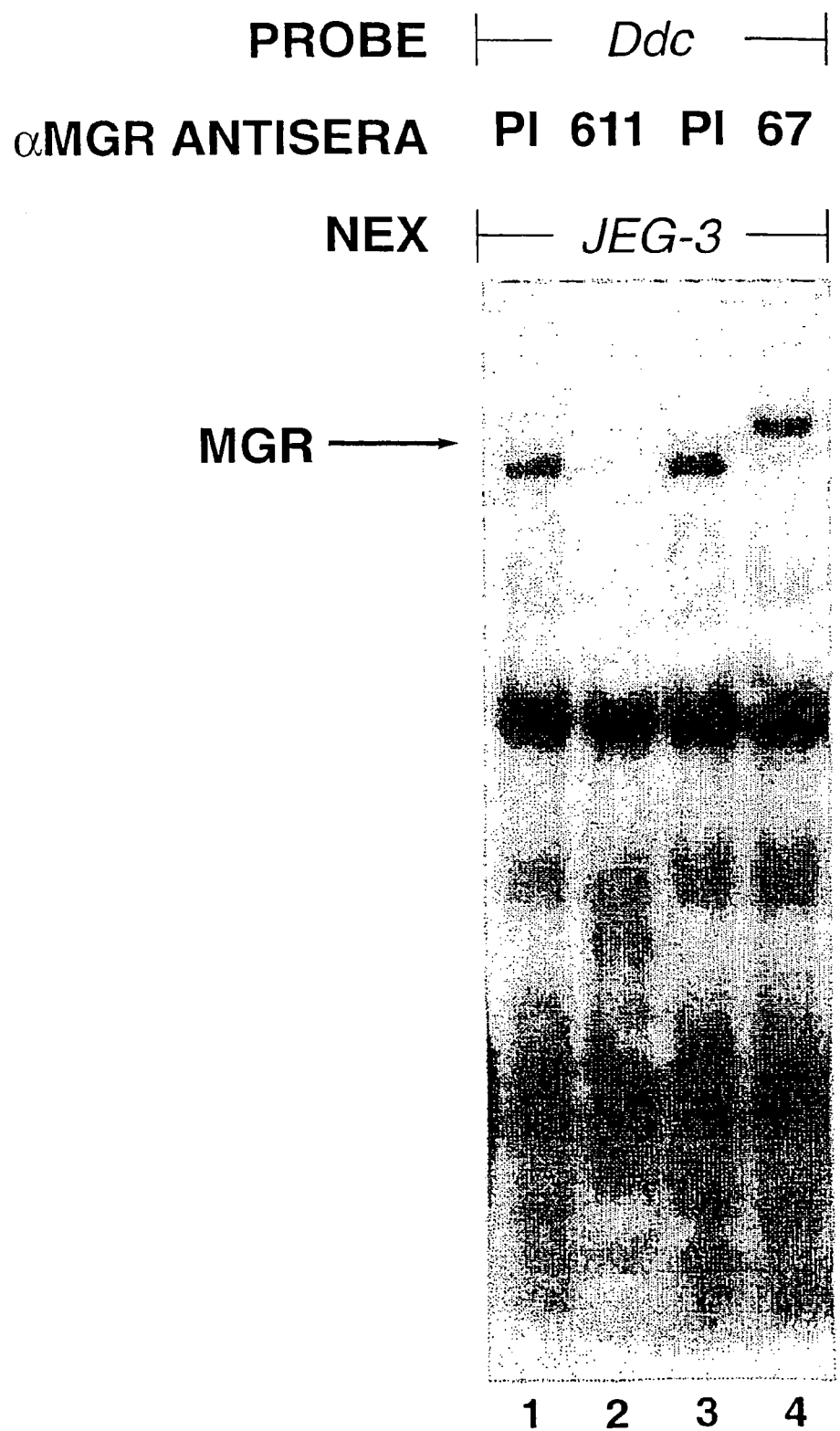

As shown in FIG. 2A, a specific protein/DNA complex was observed with the PCNA probe in the presence of pre-immune sera (lanes 1 and 3). This complex was supershifted with the addition of anti-p70 specific antisera raised against peptides in the amino terminal region of the protein (lane 4) and ablated with the addition of anti-MGR antisera raised against peptides common to p49 and p70 MGR in the dimerization domain of the protein (lane 2). Neither antisera cross-reacted with BOM. Similar results were obtained with the Dopa decarboxylase promoter probe (FIG. 2B).

EXAMPLE 6

MGR Binds to the Human Engrailed-1 Promoter

Many *Drosophila* genes regulated by GRH have known mammalian homologs. In terms of functional homology, Engrailed-1 (En-1) is one of the bests characterized. The En-1 promoter was, therefore, examined for the grainyhead consensus DNA binding sequence derived from a comparison of the *Drosophila* Ultrabithorax, Dopa decarboxylase and fushi tarazu promoters (Dynlacht et al., *Genies Dev.* 3: 1677-1688, 1989). As shown in FIG. 3A, a highly conserved region was identified in the proximal En-1 promoter.

Figure 3B:
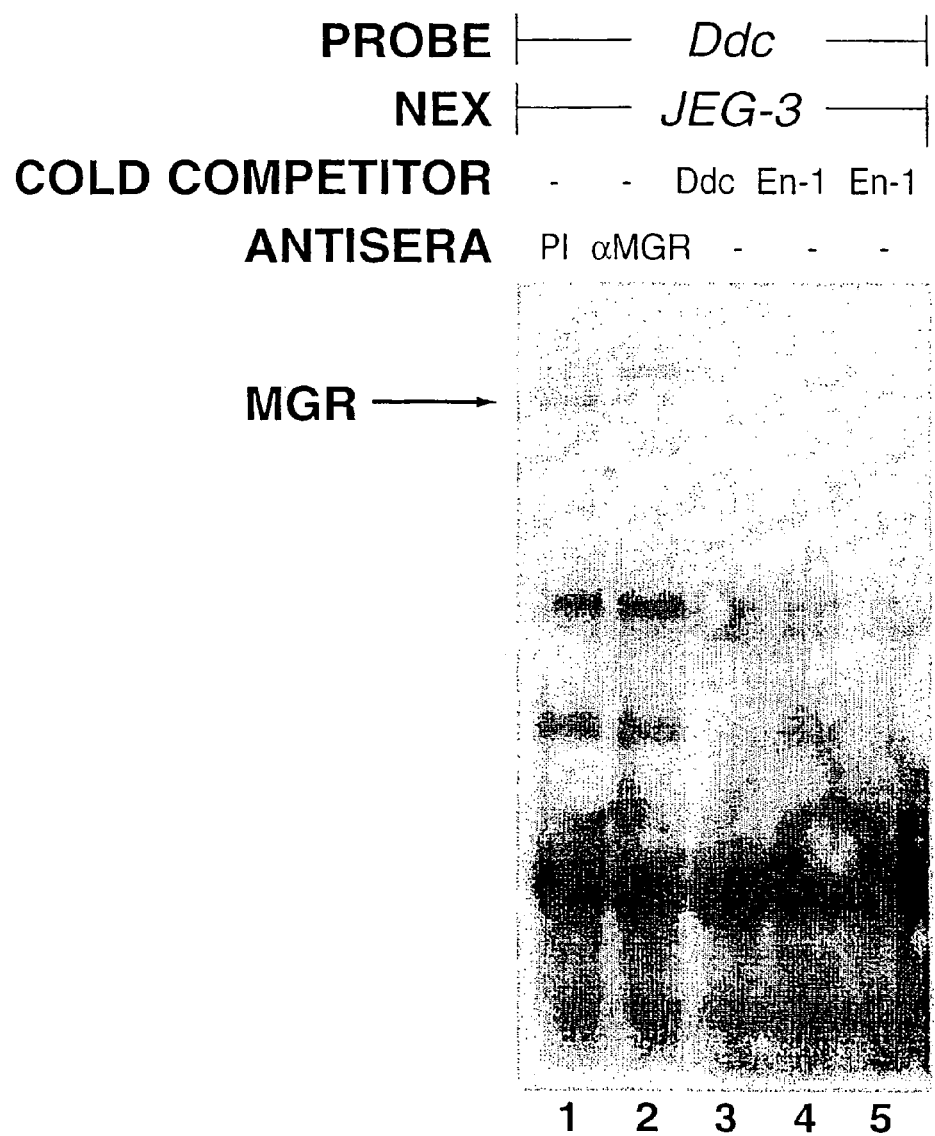
FIG. 3 are representations showing that p70 MGR binds to and transactivates the human En-1 promoter. (A) Identifcation of a grh consensus DNA binding site in the human En-1 promoter. The consensus sequence for grh DNA binding (SEQ ID NO: 50) compiled from an alignment of the *Drosophila Ultrabithorax*, Dopa decarboxylase and fushi tarazu promoters was compared with the sequence of the proximal human En-1 promoter (SEQ ID NO: 49) and the *Drosophila* engrailed promoter (SEQ ID NO: 48). The closed bracket indicates the extend of the grainyhead binding site in the engrailed promoter as defined by DNAseI footprinting. (B) Human p70 MGR binds 5 to the human En-1 promoter. Nuclear extract from the JEG-3 cell line was studied in an EMSA with a Ddc promoter probe in the presence of preimmune sera (lane 1), anti-MGR specific antisera (detailed in legend to FIG. 2) (lane 2) or cold competitor DNA (lanes 3-5). A 50-fold excess of the Ddc probe was used in lane 3 and a 10- and 20-fold excess of a human En-1 promoter probe in lanes 4 and 5, respectively. The migration of the MGR/DNA complex is shown by arrows. (C) Human p70 MGR transactivates the En-1 promoter. COS cells were transiently transfected with the proximal En-1 promoter containing the MGR binding site linked to a minimal 65-globin promoter and a firefly luciferase reporter gene (solid columns), the minimal γ-globin promoter/luciferase reporter gene (open columns)

Moreover, this sequence was also largely conserved in the DNAseI footprint attributed to grh in the *Drosophila* engrailed promoter (Soeller et al., *Genes Dev.* 2: 68-81, 1988). The ability of this region of the human En-1 promoter to compete off MGR binding to the Ddc probe (FIG. 3B) in an EMSA with nuclear extract from JEG-3 cells was examined. As shown in FIG. 3B, the specific MGR/DNA complex observed with the Ddc probe (lane 1) was supershifted with the addition of MGR antisera 67 (lane 2) and ablated with the addition of a 50-fold excess of unlabeled Ddc probe as competitor (lane 3). Addition of a 10-(lane 4) or 20-fold (lane 5) excess of unlabeled En-1 probe also markedly reduced the binding of MGR to the Ddc probe.

EXAMPLE 7

MGR Activates Transcription

Figure 3C:
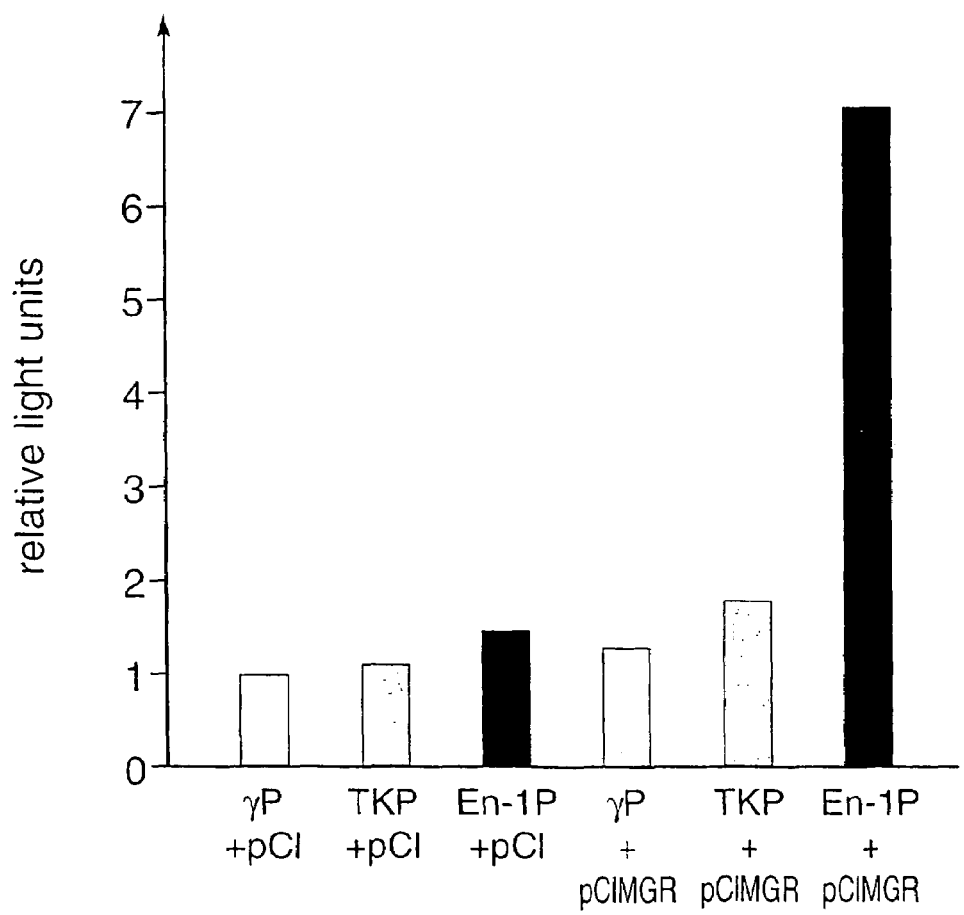

To determine the functional significance of this binding, this region of the En-1 promoter was linked to a minimal globin gene promoter/luciferase reporter gene construct and transfected it into the MGR null cell line COS, in the presence of p70 MGR mammalian expression vector or the empty vector. Transfection of the minimal promoter/reporter or the TK promoter linked to a Renilla luciferase gene with either vector served as the controls. As shown in FIG. 3C, expression of p70 MGR dramatically enhanced the transcriptional activity of the En-1 promoter (solid bars) but not the control minimal promoter (open bars) or the TK promoter (hatched bars).

EXAMPLE 8

Cloning of Full-Length Human SOM

Human SOM was cloned using primers derived from a high through-put genomic sequence (HTGS) and a human expression sequence tag (EST) obtained from GenBank databases which, respectively, aligned with the dimerization domain and the activation domain of other MGR members. Using nested RT-PCR and human tonsil cDNA, another contig spanning 1300 nucleotides was obtained.

Utilizing 5' RACE, further oligoprimers and human testis cDNA, a 210 nucleotide sequence incorporating the initiating ATG was obtained. A contig of these overlapping sequences revealed the full length human SOM which upon alignment with other existing MGR family members showed >60% similarity at the protein level with conservation at the 5' activation, DNA-binding and dimerization domains.

EXAMPLE 9

Cloning of Full-Length Murine SOM

A murine EST (GenBank) from optic cup tissue was identified, which when aligned with other murine homologs of the MGR family showed 70% similarity at the amino acid level, in the region of the DNA binding domain. Using semi-nested RT-PCR with murine testis cDNA, a 286 nucleotide sequence was amplified, cloned and sequenced for use as a probe.

Subsequently, a murine brain cDNA library (Stratagene) was screened. One clone was taken through to quaternary stage. This clone was excised from λZAP II vector into pBluescript and sequenced in both directions. A 1200 nucleotide length sequence was obtained, which lacked the 5' end.

This was subsequently identified using 5' RACE from murine testis cDNA. A contig of these two sequences revealed the full length murine SOM.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

EXAMPLE 10

Generation of Mice Heterozygous at the GRHL-3 Locus

The murine GRHL-3 locus was isolated by screening a 129/SV/J genomic library with a cDNA fragment derived from the 5' end of the gene. Polymerase chain reaction (PCR) was then used to generate a 5.8 kb NotI-BamHI fragment that when cloned into the plasmid pβgalpAloxneo, fused the second codon of GRHL-3 exon 2 to the ATG of β-galactosidase. The 3' flanking region was a SalI-KpnI fragment extending 2.6 kb from the beginning of intron 3. The thymidine kinase gene driven off the MC1-promoter was inserted into the targeting construct distal to the 3' arm as a SacII-NotI fragment and the vector was linearized with NotI and electroporated into W9.5 embryonic stem cells. Transfected cells were selected in G418 and resistant clones picked and expanded. Clones were identified in which the targeting vector had recombined with the endogenous GRHL-3 gene by hybridising SpeI digested genomic DNA with a 0.5 kb SpeI-SalI fragment situated in the 5' GRHL-3 genomic sequence just outside the targeting vector. This probe distinguished between the endogenous (8.4 kb) and targeted (11.5 kb) GRHL-3 alleles. Two correctly targeted embryonic stem cell clones were injected into C57BL/6 blastocysts to generate chimeric mice. Male chimeras were mated with C57BL/6 females to yield GRHL-3 heterozygotes which were identified by hybridising BamHI-digested genomic DNA from a tail biopsy with a 0.85 kb NcoI fragment situated in the 3' GRHL-3 genomic sequence just outside the targeting vector. This probe distinguished between the endogenous (5.2 kb) and targeted (10.7 kb) alleles. Heterozygous mice were bred with Cre deleter transgenic mice to excise the Neo$^R$ cassette. GRHL-3 heterozygotes in which the Neo$^R$ cassette had been deleted were interbred to produce wild type (GRHL-3$^{+/+}$), heterozygous (GRHL-3$^{+/-}$) and mutant (GRHL-3$^{-/-}$) mice. The inability of the targeted allele to produce GRHL-3 messenger RNA was confirmed in nucleic acid blots.

C57BL/6J inbred mice were obtained from the Walter and Eliza Hall Institute animal facility, and the ct/ct mouse stock from the Jackson Laboratory. All experiments were approved by the Melbourne Health Animal Ethics Committee.

EXAMPLE 11

Genotyping GRHL-3 Mutant Mice

Mice were genotyped by PCR using genomic DNA template prepared from tail biopsies or embryonic tissues. Products of 812 bp were generated from the wild type GRHL-3 allele and/or a product of 579 bp was generated from the targeted GRHL-3 allele. Primers used were specific for intron 1, common to the wild type and targeted GRHL-3 alleles (sense, 5'-GGATCAGAAGACCATGCC-3') (SEQ ID NO:40); intron 2, deleted from the targeted GRHL-3 allele (antisense, 5'-AGGCTGTTAGAGTTGGTG-3') (SEQ ID NO:41); and the lacZ cassette, present only in the targeted GRHL-3 allele (antisense, 5'-CTGTAGCCAGCTTTCATC-3') (SEQ ID NO:42). PCR conditions were 94° C. for 2 minutes followed by 35 cycles of 94° C. for 30 seconds, 55° C. for 30 seconds and 72° C. for 1 minute with a final 5 minutes extension at 72° C.

EXAMPLE 12

Inositol and Folate Administration During Pregnancy

GRHL-3$^{+/-}$ mice were inter-crossed and folate, inositol or PBS placebo was administered to pregnant females as previously described. Embryos were harvested on E14.5 and genotyped and examined morphologically. Mean litter size and frequency of resorptions did not differ significantly for folate-, inositol- or placebo-treated litters. The results were analysed statistically by the one-sided binomial probability test.

EXAMPLE 13

GRHL-3 Northern Hybridization and RT-PCR

A unique GRHL-3 cDNA probe from nucleotides 404 to 889 was hybridized to a blot containing 35 μg of total RNA from E14.5 ct/ct embryos. RT-PCR was performed on cDNA from DNaseI-treated total RNA (2 fig) isolated from whole E9.5 embryos (Rneasy, Qiagen) using a First Strand Synthesis for RT-PCR kit (Amersham). One-tenth of the total cDNA was used as the template in PCR reactions containing primers specific for HPRT (sense, 5'-GCTGGTGAAAAGGAC-CTCT-3' (SEQ ID NO:43); antisense, 5'-CACAGGACTA-GAACACCTGC-3') (SEQ ID NO:44). The cDNA sample was then diluted to give similar amplification of HPRT under the same PCR conditions prior to use in PCR reactions containing GRHL-3-specific primers. E9.5 GRHL-3$^{+/-}$ and GRHL-3$^{-/-}$ embryo cDNA was amplified with specific primers annealing to exon 8 and exon 13 (sense; 5'-CACAT-TGAAGAGGTGGC-3' (SEQ ID NO:45); antisense, 5'-AAGGGTGAGCAGGTTCGCTT-3') (SEQ ID NO:46). PCR conditions were 94° C. for 2 minutes followed by various cycles of 94° C. for 30 seconds, 60° C. for 30 seconds and 72° C. for 1 minute. All PCR products were electrophoresed on 1.5% agarose gels, transferred to nitrocellulose membranes and analyzed by Southern blotting using P-labelled internal oligonucleotides as probes.

Quantitative Real-Time RT-PCR was performed in a Rotorgene 2000 (Corbett Research, Australia) in a final volume of 20 μl. Reaction mixtures comprised 1× reaction buffer plus 2.5 mM (HPRT) or 3 mM (GRHL-3) MgCl$_2$, 0.05 mM dNTPs (Roche), 0.1 μM gene-specific primers, 1U Taq (Fisher Biotech, Australia), a 1/10000 dilution of SYBR Green I (Molecular Probes, USA), and 2 μl of sample or standard. Cycling conditions were 94° C. for 15 seconds, 55° C. (GRHL-3) or 52° C. (HPRT) for 30 seconds and 72° C. for 30 seconds. For each reaction, standard curves were generated and relative quantities of each transcript were calculated from this. The ratio of GRHL-3/HPRT normalised to wild type E14.5 is shown. Error bars show the sum of the standard deviations for each sample as a proportion of the normalised signal. The identity of the PCR products was confirmed by melt curve analysis and agarose gel electrophoresis on a 1.5% agarose gel.

EXAMPLE 14

Histology, In Situ Hybridization and Whole Mount Skeletal Staining of GRHL-3 Mutant Mice Embryos from timed pregnant C57BL/6J females and GRHL-3$^{+/-}$ intercrosses were immersion fixed in 4% paraformaldehyde in phosphate buffered saline, pH 7.3. The embryos were then embedded in paraffin wax before 8 μm sections were cut on a microtome and placed on gelatine-coated slides. For histological analysis, sections were stained with hematoxylin and eosin. In situ hybridisation was performed as described previously. A radio-labelled GRHL-3 antisense RNA probe was transcribed from a pBluescript II SK plasmid (Stratagene) carrying a 485 bp fragment of the GRHL-3 coding region (nt 404 to 889) using T7 RNA polymerase. All sections for in situ analysis were counter-stained with hematoxylin. In situ hybridisation was also performed using a full-length GRHL-3 probe and the same expression pattern was observed (data not shown). Hybridisation signal was similar to background levels in embryos homozygous for the GRHL-3 mutation. Whole mount skeletal staining on E17.5 embryos was performed as described previously.

EXAMPLE 15

Expression of GRHL-3 During Mouse Development

Figure 4A:
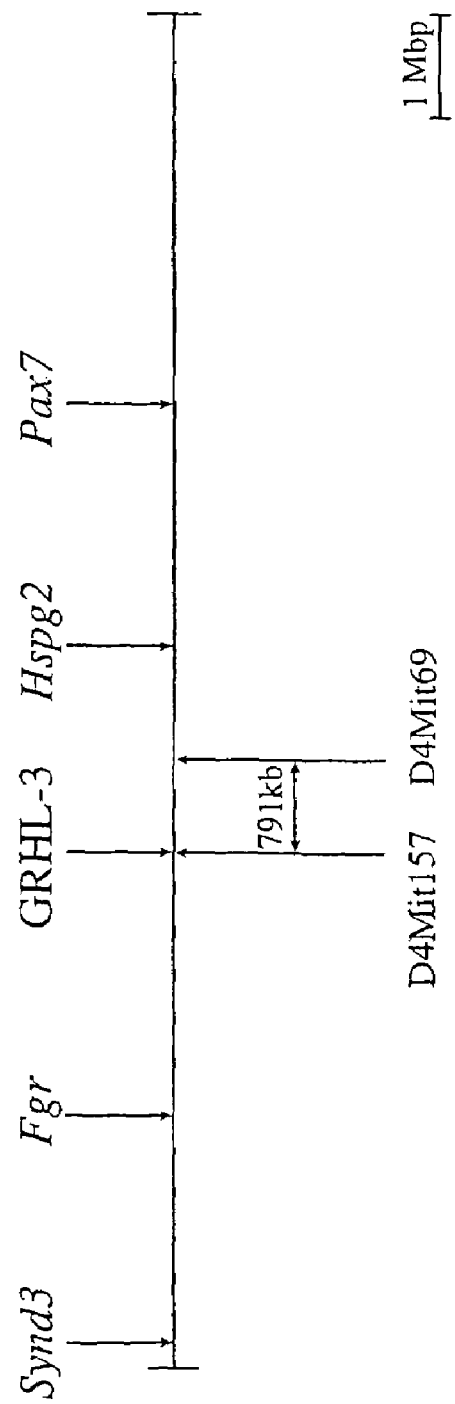
Figure 4B:
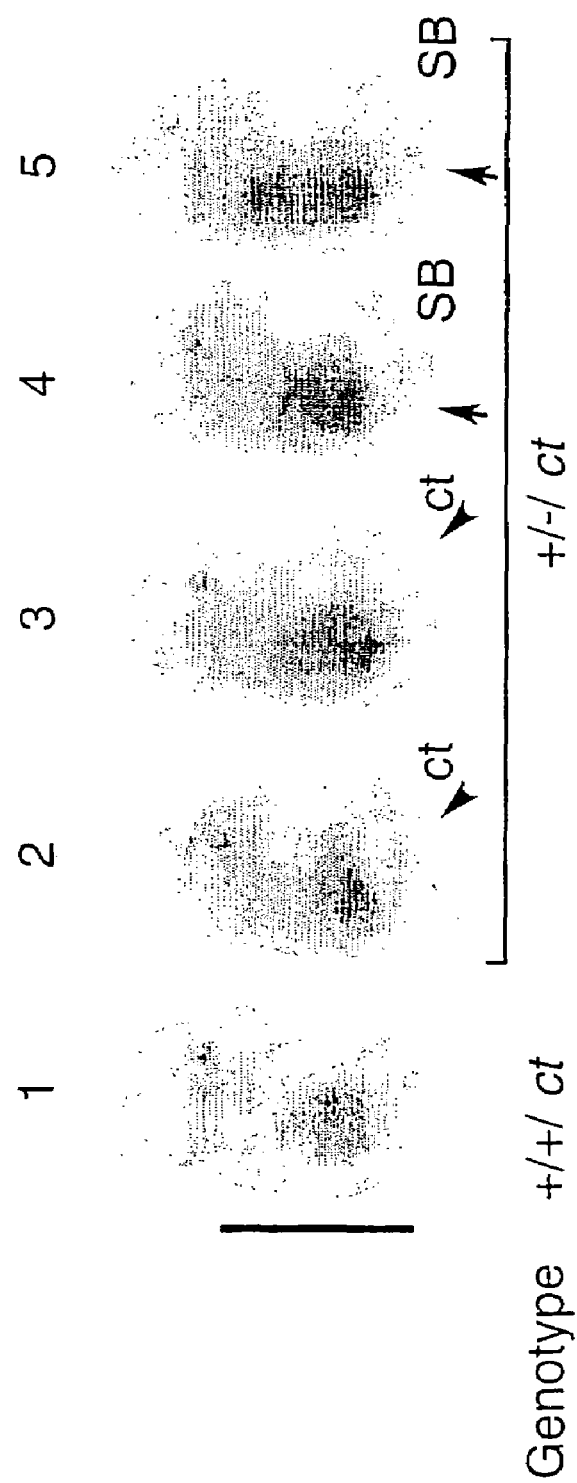
Figure 4C:
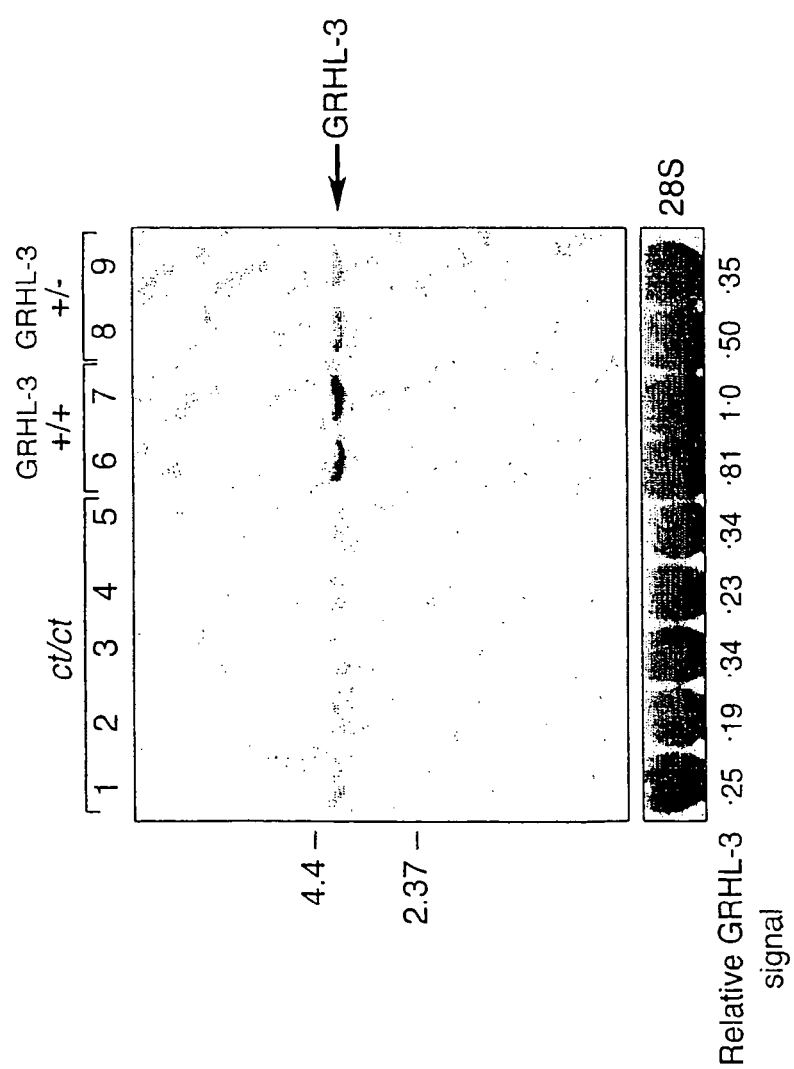
Figure 4D:
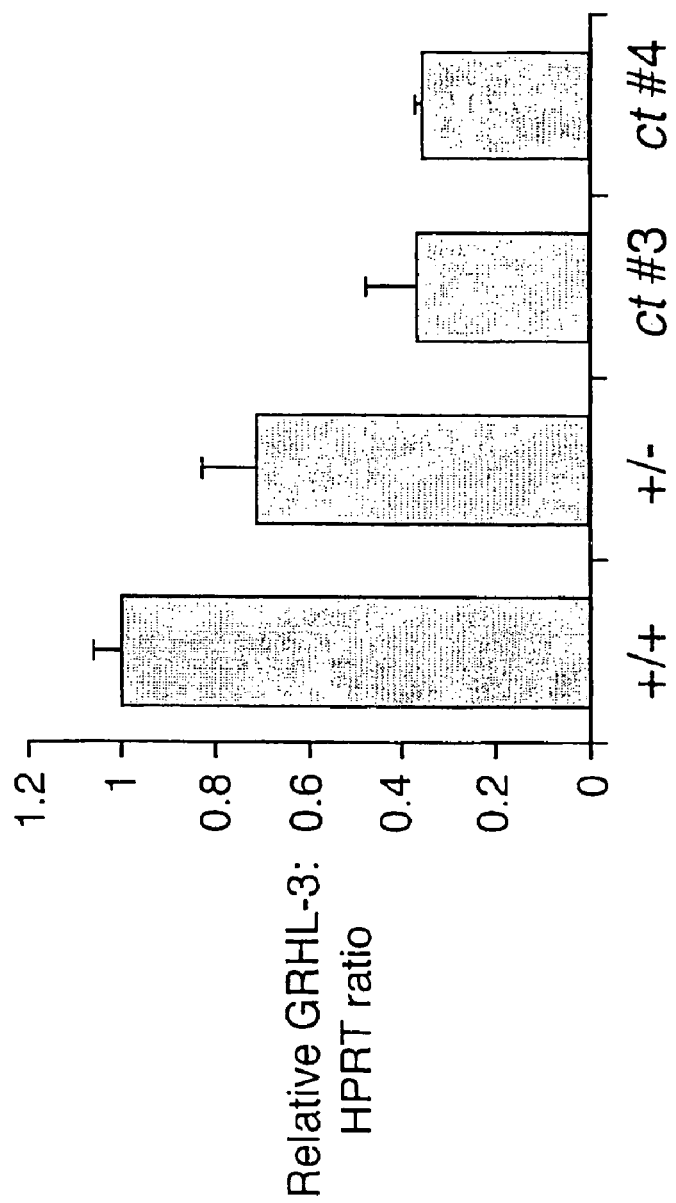
Figure 5A:
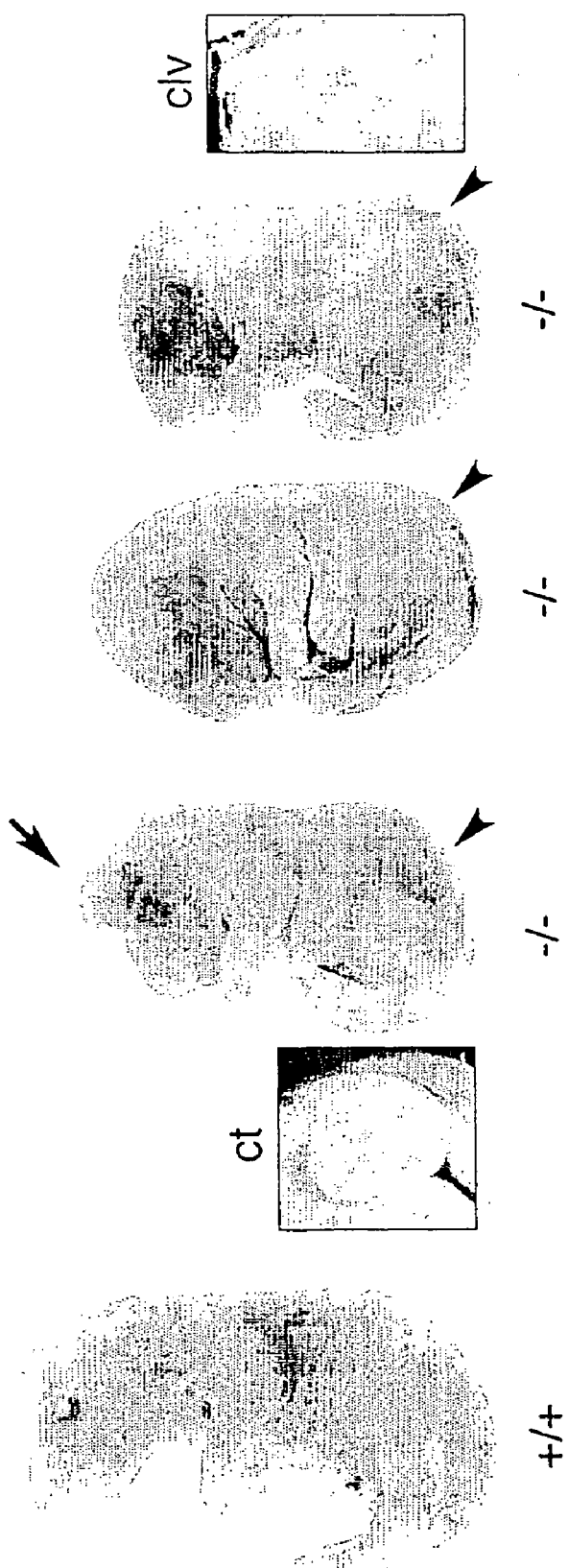
Figure 5B:
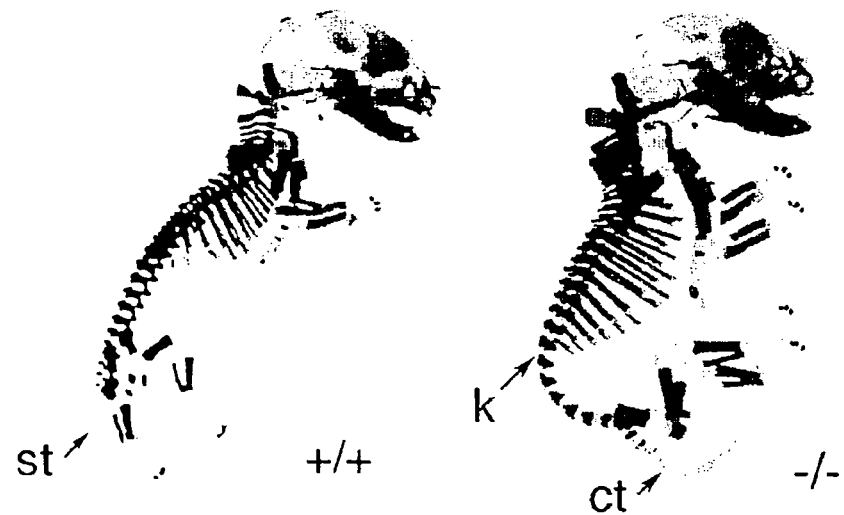
Figure 5C:
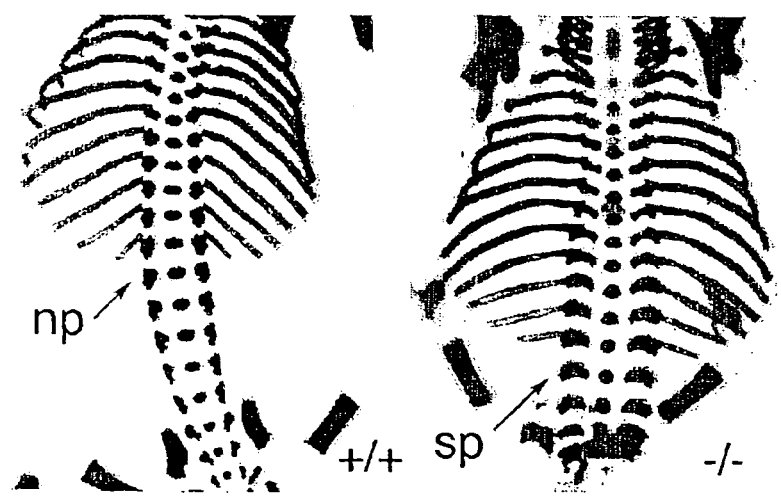
Figure 5D:
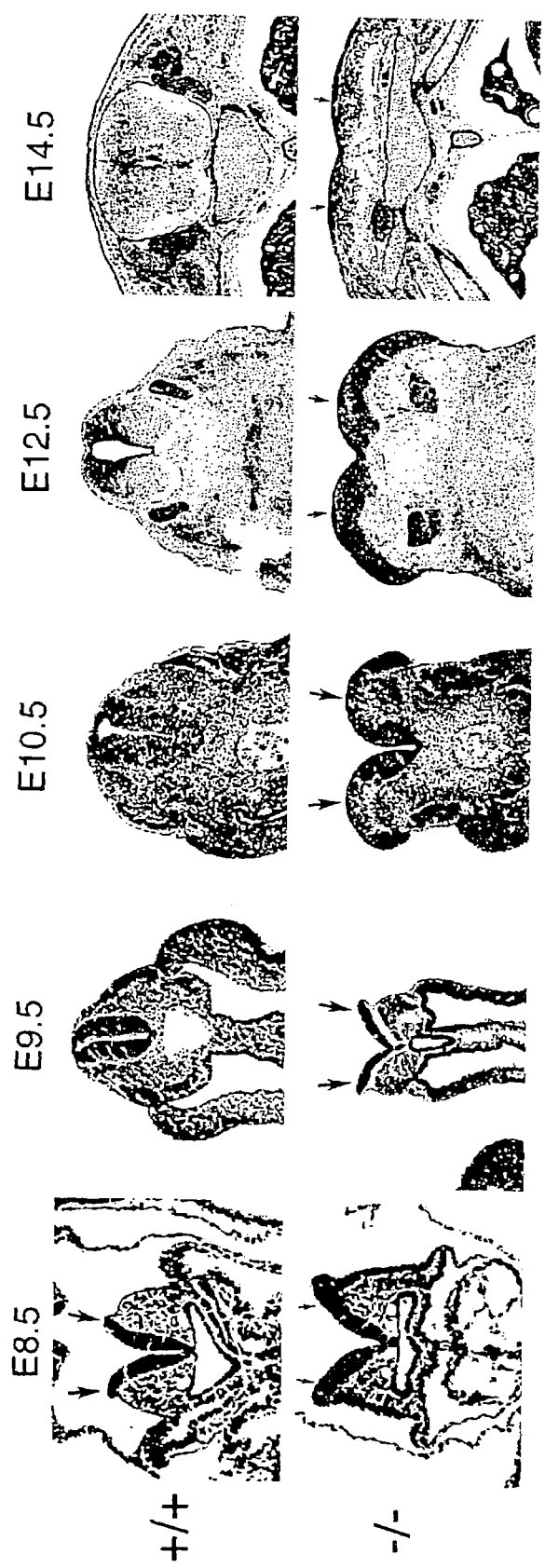

One criterion for defining specific neurulation genes is that they are expressed in the region of the folding neural plate at the appropriate developmental time point. To determine the pattern of expression of GRHL-3 during murine development, in situ hybridisation studies were performed using a probe specific for GRHL-3 (FIG. 4). In embryos at E8, it was observed that expression was confined to the non-neuronal ectoderm immediately adjacent to the neural plate that was undergoing folding to form the neural tube (FIG. 4A,B). At later time-points, more widespread expression was observed in the surface ectoderm with a progressive increase from E12.5 to E15.5 (FIG. 4C,D). The pattern of expression at later time points is similar to the expression profiles of murine GRHL-1 and -2 (Ref. 8).

EXAMPLE 16

NTDs in GRHL-3 Mutant Mice

Figure 7A:
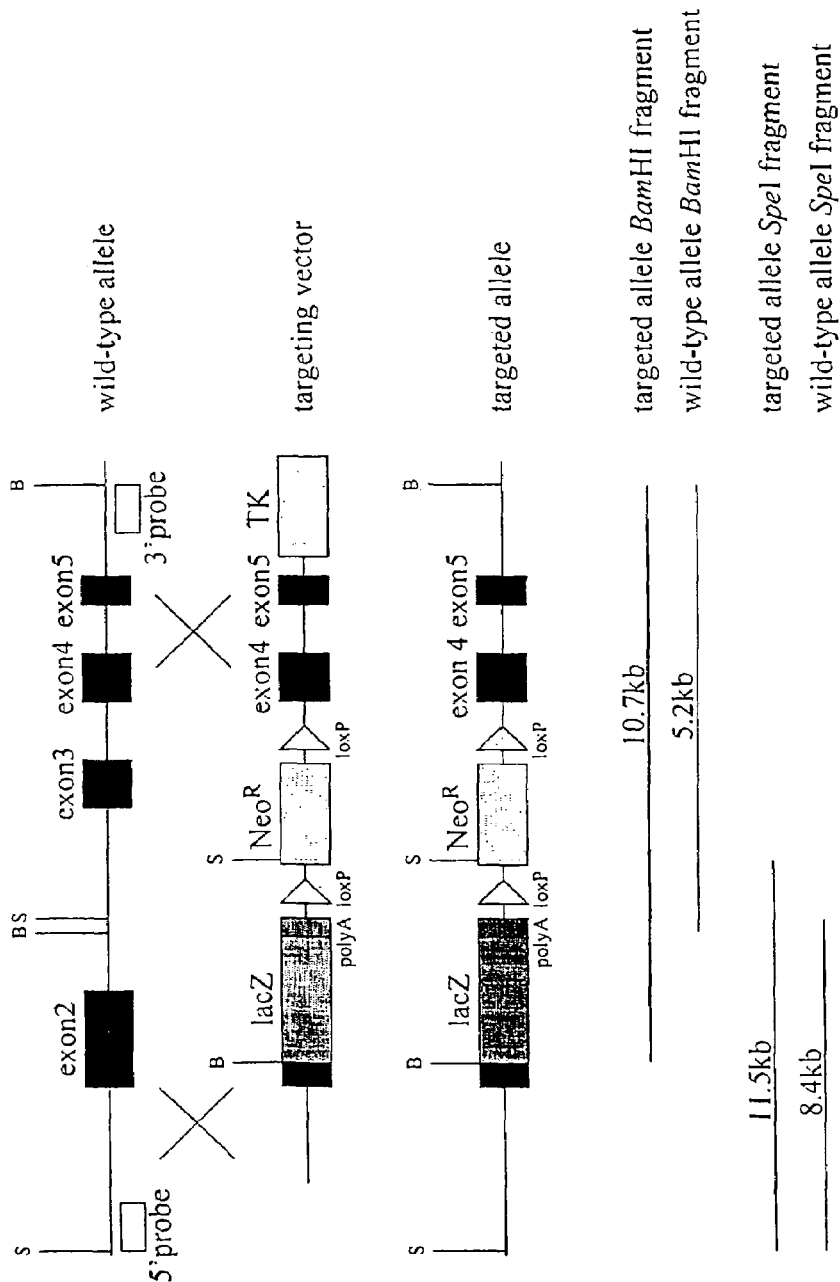
Figures 7B, 7C, 7D:
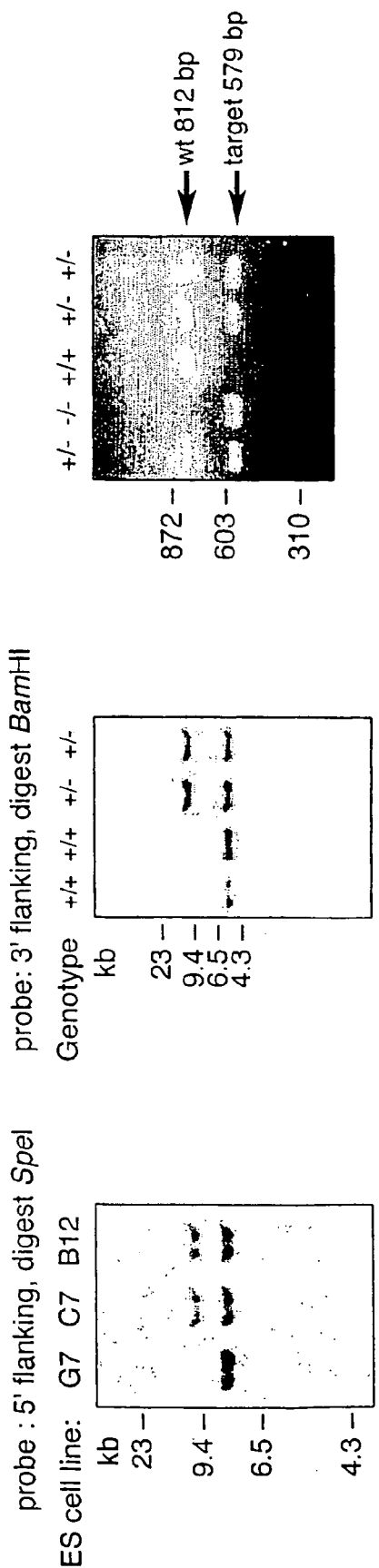
Figures 7E, 7F:
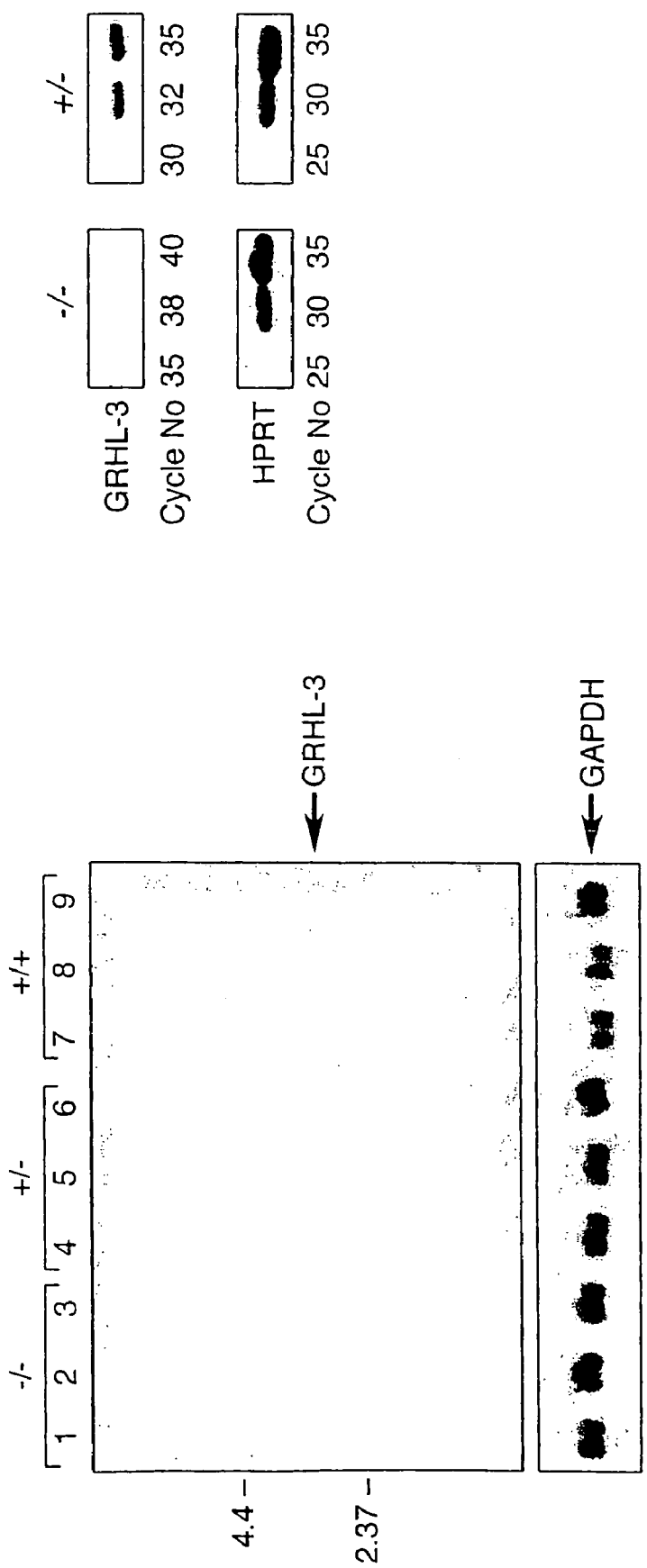

To determine the functional role of GRHL-3 during mouse development, a 2.2 kb deletion in GRHL-3 was generated by gene targeting (FIG. 5A-D). Northern blot and RT-PCR analysis indicated that the targeted GRHL-3 allele represented a null mutation (FIGS. 7E and F). Genotyping of offspring from GRHL-3$^{+/-}$ intercrosses from mid and late gestation, showed that GRHL-3$^{-/-}$ mice were represented in Mendelian proportions up to E18.5. Of 874 embryos examined on, or before this time, 191 (22%) were genotyped as GRHL-3$^{-/-}$. No GRHL-3$^{-/-}$ embryos survived to weaning.

Figure 6A:
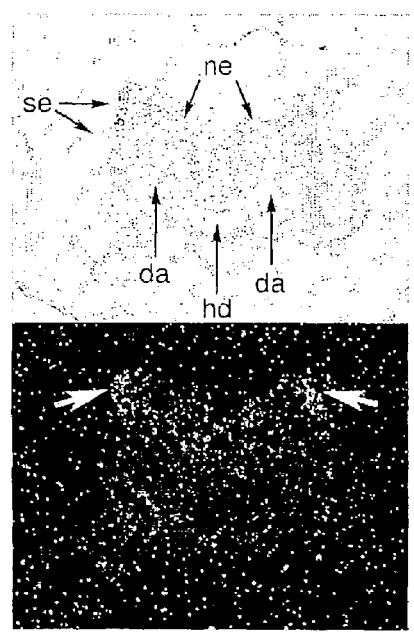
Figure 6B:
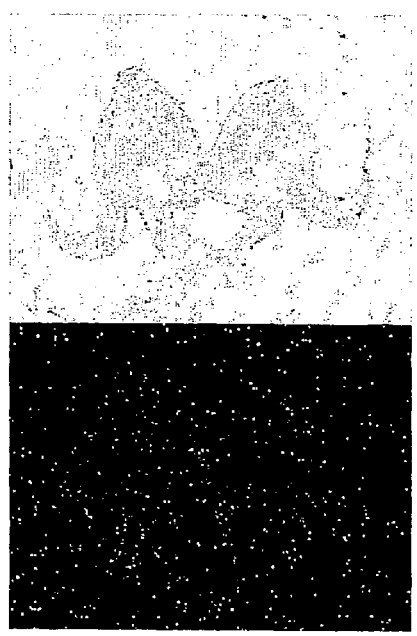
Figure 6C:
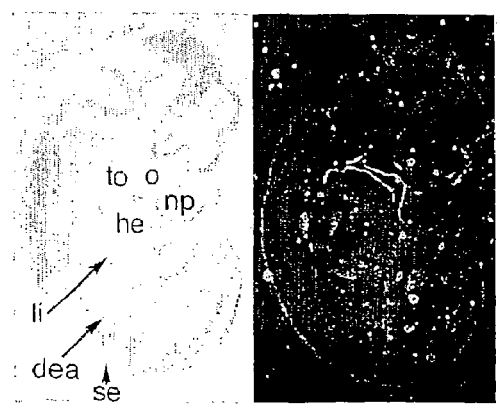
Figure 6D:
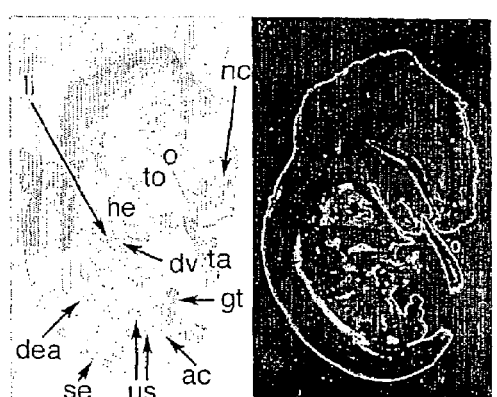

All GRHL-3$^{-/-}$ pups, without exception, displayed neural tube defects (NTDs). GRHL-3$^{+/-}$ mice were indistinguishable from their wild-type littermates. As most of the newborn GRHL-3$^{-/-}$ pups were cannibalised by their mothers, we examined the phenotype in more detail in developing embryos (FIG. 6A). All GRHL-3$^{-/-}$ embryos exhibited thoraco-lumbo-sacral spina bifida and curled tail and 3% had co-incident exencephaly. GRHL-3$^{-/-}$ embryos were also smaller than their littermate controls. Full body skeletal preparations demonstrated abnormalities in the vertebral column with kyphosis, splayed spinal processes and lack of vertebral arch formation (FIG. 6B,C). Transverse sections through the thoracic, lumbar and sacral regions at different developmental time points showed that spina bifida in GRHL-3$^{-/-}$ embryos was due to a primary failure of neural tube closure. The neural plate appeared to furrow normally with the formation of the median hinge point, but neural fold elevation did not occur and the neuro-epithelium remained convex throughout gestation (FIG. 6D).

EXAMPLE 17

The GRHL-3 Gene is Allelic with the ct Gene

Analysis of GRHL-3 mutant mice revealed phenotypic similarities between the GRHL-3$^{-/-}$ embryos and those reported in the cully tail mouse mutant[4]. The curly tail gene is incompletely penetrant, with homozygotes developing lumbo-sacral spina bifida aperta (12%), curled tail (50%) and exencephaly (3%). The ct locus had been mapped to murine chromosome 4, at position 63.4, close to the D4Mit69 marker. The NCBI STS database to ascertain the chromosomal localisation of GRHL-3 in mice. The mGRHL-3 gene is also located on chromosome 4, approximately 3 kb from D4Mit157 at position 63.4. This marker, which lies within 800 kb of D4Mit69, had not been included in the original curly tail mapping studies. Both markers were subsequently identified in a recently deposited 13 Mb contiguous sequence from chromosome 4 (FIG. 7A). Also contained in this sequence were several genes that have previously been studied (and excluded) as ct candidate genes. GRHL-3 was positioned closer to the D4Mit69 marker than all of these excluded candidates. Genetic complementation studies were therefore performed using mice heterozygous for the null GRHL-3 allele and ct/ct mice. Embryos from these matings were harvested between E 11.5 and E18.5 days and genotyped and examined morphologically. Among the 101 embryos obtained, NTDs were the only gross abnormalities observed (FIG. 7B). These were confined, without exception, to embryos with a GRHL-3$^{+/-}$/ct genotype (Table 5). The incidence of spina bifida in mice carrying both mutant alleles was higher than reported for curly tail homozygotes (31% versus 12%), but the extent of the defect more closely resembled that of the ct/ct mice (lumbo-sacral spina bifida) than the GRHL-3$^{-/-}$ mice (thoraco-lumbo-sacral spina bifida). Tail flexion defects alone were identified in an additional 23% of embryos, all of which were genotyped as GRHL-3$^{+/-}$/ct. Ten embryos carrying both mutant alleles appeared morphologically normal and the remaining 37% of embryos were unremarkable and genotyped as GRHL-3$^{+/+}$/ct.

The expression of GRHL-3 in curly tail homozygous embryos was compared with wild type and GRHL-3$^{+/-}$ controls by Northern blotting (FIG. 7C). Densitometry of the GRHL-3 signal normalised to the 28S signal obtained by Phosphorimager analysis revealed a significant reduction in the level of GRHL-3 mRNA in ct/ct embryos (19-34%) compared with wild type or GRHL-3 heterozygous controls. Real-time quantitative RT-PCR was performed on mRNA from these embryos and confirmed that the level of GRHL-3 expression in ct/ct embryos was reduced approximately 3-fold compared to wild type controls (FIG. 7D).

TABLE 5

Phenotypes of embryos from GRHL-3$^{+/-}$ X ct/ct crosses

| Phenotype | Number | Genotype |
|---|---|---|
| Spina bifida + curly tail | 31 | GRHL-3$^{+/-}$/ct-31 |
| Curled tail | 23 | GRHL-3$^{+/-}$/ct-23 |
| Normal | 47 | GRHL-3$^{+/-}$/ct-10 |
|  |  | GRHL-3$^{+/+}$/ct-37 |
| Total | 101 | 101 |

Embryos were harvested between E11.5 and E18.5.

EXAMPLE 18

NTDs in GRHL-3$^{-/-}$ Embryos are Folate- and Inositol-Resistant

NTDs in the curly tail mice are resistant to folate administered in early gestation. However, inositol therapy in pregnancy results in a marked reduction in the incidence of spina bifida. The effects of folate and inositol administration on pregnant GRHL-3$^{+/-}$ mice previously mated with GRHL-3$^{+/-}$ males was examined (Table 6). As expected, no rescue of spina bifida in GRHL-3$^{-/-}$ embryos with placebo or folate treatment was observed. In contrast to the ct/ct mice, neither the incidence, nor severity of the spina bifida in the GRHL-3$^{-/-}$ embryos was alleviated by inositol treatment. Although the numbers of embryos examined was small, the result was highly significant (p<0.001) given the 70% reduction in the incidence of spina bifida in inositol-treated ct/ct embryos. These findings indicate that GRHL-3 expression is essential for inositol-mediated rescue of folate-resistant NTDs.

TABLE 6

Effects of folate and inositol administration on NTDs in GRHL-3$^{-/-}$ mice

| Genotype GRHL-3$^{-/-}$ | Placebo n = 5 | Folate n = 4 | Inositol n = 8 |
|---|---|---|---|
| Predicted NTDs | 100% | 100% | 30% |
| Observed NTDs | 100% | 100% | 100%* |

*p < 0.001

---

What is claimed is:

1. An isolated nucleic acid molecule comprising a sequence of nucleotides encoding a mammalian transcription factor comprising the amino acid sequence set forth in SEQ ID NO: 8 or an amino acid sequence having at least 95% identity thereto.

2. The isolated nucleic acid molecule of claim 1 wherein the molecule has a nucleotide sequence selected from the group consisting of: SEQ ID NO: 7, SEQ ID NO: 15, and a nucleotide sequence which hybridizes to the full-length, complementary sequences of SEQ ID NO: 7 or SEQ ID NO:15 under conditions of 0.1×SSC, 0.1% w/v SDS at 65° C.

3. The isolated nucleic acid molecule of claim 1 encoding a polypeptide comprising an amino acid sequence selected from the group consisting of SEQ ID NO: 8 and SEQ ID NO: 16.

4. The isolated nucleic acid molecule of claim 1 comprising a nucleotide sequence selected from the group consisting of SEQ ID NO: 7 and SEQ ID NO: 15.

5. The isolated nucleic acid molecule of claim 1 comprising the nucleotide sequence set forth in SEQ ID NO: 7.

6. The isolated nucleic acid molecule of claim 1 comprising the nucleotide sequence set forth in SEQ ID NO: 15.

* * * * *

SEQUENCE LISTING

<160> NUMBER OF SEQ ID NOS: 46

<210> SEQ ID NO 1
<211> LENGTH: 1881
<212> TYPE: DNA
<213> ORGANISM: human
<220> FEATURE:
<221> NAME/KEY: CDS
<222> LOCATION: (94)..(1323)

<400> SEQUENCE: 1

```
ataagagagg ccatctgaca gctccagata cgacagtcac tgtctccata gcaacgatgc      60
ctacccactc catcaagaca gaaacccagc cac atg gct tcg ctg tgg gaa tcc     114
                                   Met Ala Ser Leu Trp Glu Ser
                                     1               5 ccc cag cag tgt atc atc ctg agc cca ctg agc ggg tgg tgg ttt tcg      162
Pro Gln Gln Cys Ile Ile Leu Ser Pro Leu Ser Gly Trp Trp Phe Ser
         10                  15                  20 atc gga atc tca ata ctg acc agt tca gct ctg gtg ctc aag ccc caa      210
Ile Gly Ile Ser Ile Leu Thr Ser Ser Ala Leu Val Leu Lys Pro Gln
 25                  30                  35 atg ctc aaa ggc gaa ctc cag act cga cct tct cag aga cct tca agg      258
Met Leu Lys Gly Glu Leu Gln Thr Arg Pro Ser Gln Arg Pro Ser Arg
 40                  45                  50                  55 aag gcg ttc agg agg aac aac ttt gaa tat acc cta gaa gct tca aaa      306
Lys Ala Phe Arg Arg Asn Asn Phe Glu Tyr Thr Leu Glu Ala Ser Lys
                 60                  65                  70 tca ctt cga cag aag cca gga gac agt acc atg acg tac ctg aac aaa      354
Ser Leu Arg Gln Lys Pro Gly Asp Ser Thr Met Thr Tyr Leu Asn Lys
             75                  80                  85 ggc cag ttc tat ccc atc acc ttg aag gag gtg agc agc agt gaa gga      402
Gly Gln Phe Tyr Pro Ile Thr Leu Lys Glu Val Ser Ser Ser Glu Gly
         90                  95                 100 atc cat cat ccc atc agc aaa gtt cga agt gtg atc atg gtg gtt ttt      450
Ile His His Pro Ile Ser Lys Val Arg Ser Val Ile Met Val Val Phe
    105                 110                 115 gct gaa gac aaa agc aga gaa gat cag tta agg cat tgg aag tac tgg      498
```

```
                Ala Glu Asp Lys Ser Arg Glu Asp Gln Leu Arg His Trp Lys Tyr Trp
                120                 125                 130                 135 cac tcc cgg cag cac acc gct aaa caa aga tgc att gac ata gct gac              546
His Ser Arg Gln His Thr Ala Lys Gln Arg Cys Ile Asp Ile Ala Asp
                140                 145                 150 tat aaa gaa agc ttc aac act atc agt aac atc gag gag att gcg tat              594
Tyr Lys Glu Ser Phe Asn Thr Ile Ser Asn Ile Glu Glu Ile Ala Tyr
                155                 160                 165 aac gcc att tcc ttc aca tgg gac atc aac gat gaa gca aag gtt ttc              642
Asn Ala Ile Ser Phe Thr Trp Asp Ile Asn Asp Glu Ala Lys Val Phe
                170                 175                 180 atc tct gtg aac tgc tta agc aca gat ttc tct tcc cag aag gga gtg              690
Ile Ser Val Asn Cys Leu Ser Thr Asp Phe Ser Ser Gln Lys Gly Val
                185                 190                 195 aag ggg ttg cct ctt aac att caa gtt gat acc tat agt tac aac aac              738
Lys Gly Leu Pro Leu Asn Ile Gln Val Asp Thr Tyr Ser Tyr Asn Asn
200                 205                 210                 215 cgc agc aac aag cct gtg cac cgg gcc tac tgc cag atc aag gtc ttc              786
Arg Ser Asn Lys Pro Val His Arg Ala Tyr Cys Gln Ile Lys Val Phe
                220                 225                 230 tgt gac aag gga gct gag cgg aaa atc agg gat gaa gaa cga aag caa              834
Cys Asp Lys Gly Ala Glu Arg Lys Ile Arg Asp Glu Glu Arg Lys Gln
                235                 240                 245 agc aaa aga aaa gtt tct gat gtt aaa gtg cca ctg ctt ccc tct cac              882
Ser Lys Arg Lys Val Ser Asp Val Lys Val Pro Leu Leu Pro Ser His
                250                 255                 260 aag cga atg gat atc aca gtt ttc aaa ccc ttc att gat ctc gat act              930
Lys Arg Met Asp Ile Thr Val Phe Lys Pro Phe Ile Asp Leu Asp Thr
265                 270                 275 cag cct gtc ctc ttc att cct gac gtg cac ttt gcc aac ttg cag cgg              978
Gln Pro Val Leu Phe Ile Pro Asp Val His Phe Ala Asn Leu Gln Arg
280                 285                 290                 295 ggc act cat gtc ctt ccc att gcc tct gaa gaa ttg gag ggt gaa ggc             1026
Gly Thr His Val Leu Pro Ile Ala Ser Glu Glu Leu Glu Gly Glu Gly
                300                 305                 310 tct gtc ttg aaa agg ggg ccg tac ggc aca gaa gat gac ttt gct gtc             1074
Ser Val Leu Lys Arg Gly Pro Tyr Gly Thr Glu Asp Asp Phe Ala Val
                315                 320                 325 cct cct tct acc aag ctg gcc cgg ata gaa gaa cca aag aga gtg ctg             1122
Pro Pro Ser Thr Lys Leu Ala Arg Ile Glu Glu Pro Lys Arg Val Leu
                330                 335                 340 ctc tac gtt cga aag gag tca gaa gaa gtc ttt gat gcc ctg atg ctc             1170
Leu Tyr Val Arg Lys Glu Ser Glu Glu Val Phe Asp Ala Leu Met Leu
345                 350                 355 aaa acc cca tct ttg aag ggc ttg atg gaa gct atc tca gac aaa tac             1218
Lys Thr Pro Ser Leu Lys Gly Leu Met Glu Ala Ile Ser Asp Lys Tyr
360                 365                 370                 375 gat gtt ccc cat gac aag att ggg aaa ata ttc aag aag tgt aaa aag             1266
Asp Val Pro His Asp Lys Ile Gly Lys Ile Phe Lys Lys Cys Lys Lys
                380                 385                 390 ggg atc ctg gtg aac atg gac gac aac att gtg aag cat tac tcc aat             1314
Gly Ile Leu Val Asn Met Asp Asp Asn Ile Val Lys His Tyr Ser Asn
                395                 400                 405 gag gac acc ttccagctgc agattgaaga agccgggggg tcttacaagc                     1363
Glu Asp Thr
        410 tcaccctgac ggagatctaa aggcctgcgg gccacagctc cccaggagtt cagtgcaggt           1423 gtttctagat cttacggttt ggcaactgca ggtaacccca gtcagccatg tcgccagcac           1483
```

-continued

```
aggtctatgt cgagggaatg ggttccttgc aggttggagg cggggctgca tctggcttgg    1543
tggtagcatt taatctattg cattggtgtt tttcagatga aagagaaatc catataccat    1603
tatgtttgaa tttcctgata tacaggat ttaaagtgaa aactttattc caagagttaa     1663
cagagtctct gggaagcttt aggacatctg ctacgttatt tatcaaaata ttgggatctc    1723
tgccttgtgc ctacagtgtc gtgggcctgc tcgctagcag aagtcagaaa aggcgatagg    1783
cttggcttta aggatttcgt gcccttgcct gaattcagta caactccact gcctcacgtt    1843
agcgggagcg cacctgaaga gtacgggggg agccctct                           1881
```

<210> SEQ ID NO 2
<211> LENGTH: 410
<212> TYPE: PRT
<213> ORGANISM: human

<400> SEQUENCE: 2

```
Met Ala Ser Leu Trp Glu Ser Pro Gln Gln Cys Ile Ile Leu Ser Pro
1               5                   10                  15

Leu Ser Gly Trp Trp Phe Ser Ile Gly Ile Ser Ile Leu Thr Ser Ser
            20                  25                  30

Ala Leu Val Leu Lys Pro Gln Met Leu Lys Gly Glu Leu Gln Thr Arg
        35                  40                  45

Pro Ser Gln Arg Pro Ser Arg Lys Ala Phe Arg Arg Asn Asn Phe Glu
    50                  55                  60

Tyr Thr Leu Glu Ala Ser Lys Ser Leu Arg Gln Lys Pro Gly Asp Ser
65                  70                  75                  80

Thr Met Thr Tyr Leu Asn Lys Gly Gln Phe Tyr Pro Ile Thr Leu Lys
                85                  90                  95

Glu Val Ser Ser Glu Gly Ile His His Pro Ile Ser Lys Val Arg
            100                 105                 110

Ser Val Ile Met Val Val Phe Ala Glu Asp Lys Ser Arg Glu Asp Gln
        115                 120                 125

Leu Arg His Trp Lys Tyr Trp His Ser Arg Gln His Thr Ala Lys Gln
    130                 135                 140

Arg Cys Ile Asp Ile Ala Asp Tyr Lys Glu Ser Phe Asn Thr Ile Ser
145                 150                 155                 160

Asn Ile Glu Glu Ile Ala Tyr Asn Ala Ile Ser Phe Thr Trp Asp Ile
                165                 170                 175

Asn Asp Glu Ala Lys Val Phe Ile Ser Val Asn Cys Leu Ser Thr Asp
            180                 185                 190

Phe Ser Ser Gln Lys Gly Val Lys Gly Leu Pro Leu Asn Ile Gln Val
        195                 200                 205

Asp Thr Tyr Ser Tyr Asn Asn Arg Ser Asn Lys Pro Val His Arg Ala
    210                 215                 220

Tyr Cys Gln Ile Lys Val Phe Cys Asp Lys Gly Ala Glu Arg Lys Ile
225                 230                 235                 240

Arg Asp Glu Glu Arg Lys Gln Ser Lys Arg Lys Val Ser Asp Val Lys
                245                 250                 255

Val Pro Leu Leu Pro Ser His Lys Arg Met Asp Ile Thr Val Phe Lys
            260                 265                 270

Pro Phe Ile Asp Leu Asp Thr Gln Pro Val Leu Phe Ile Pro Asp Val
        275                 280                 285

His Phe Ala Asn Leu Gln Arg Gly Thr His Val Leu Pro Ile Ala Ser
    290                 295                 300
```

-continued

```
Glu Glu Leu Glu Gly Glu Gly Ser Val Leu Lys Arg Gly Pro Tyr Gly
305                 310                 315                 320

Thr Glu Asp Asp Phe Ala Val Pro Pro Ser Thr Lys Leu Ala Arg Ile
            325                 330                 335

Glu Glu Pro Lys Arg Val Leu Leu Tyr Val Arg Lys Glu Ser Glu Glu
        340                 345                 350

Val Phe Asp Ala Leu Met Leu Lys Thr Pro Ser Leu Lys Gly Leu Met
    355                 360                 365

Glu Ala Ile Ser Asp Lys Tyr Asp Val Pro His Asp Lys Ile Gly Lys
370                 375                 380

Ile Phe Lys Lys Cys Lys Lys Gly Ile Leu Val Asn Met Asp Asp Asn
385                 390                 395                 400

Ile Val Lys His Tyr Ser Asn Glu Asp Thr
                405                 410

<210> SEQ ID NO 3
<211> LENGTH: 2361
<212> TYPE: DNA
<213> ORGANISM: human
<220> FEATURE:
<221> NAME/KEY: CDS
<222> LOCATION: (7)..(1860)
<220> FEATURE:
<221> NAME/KEY: VARIANT
<222> LOCATION: 342
<223> OTHER INFORMATION: Xaa = Lys, Ile

<400> SEQUENCE: 3 agcgcg atg aca cag gag tac gac aac aaa cgg cca gtg ttg gtt ctt         48
       Met Thr Gln Glu Tyr Asp Asn Lys Arg Pro Val Leu Val Leu
       1               5                   10 cag aat gaa gca ctt tat cca cag cgg cgg tcc tac act agt gag gat        96
Gln Asn Glu Ala Leu Tyr Pro Gln Arg Arg Ser Tyr Thr Ser Glu Asp
15                  20                  25                  30 gag gcc tgg aaa tcc ttc ctg gaa aac cct ctc act gca gcg acc aaa       144
Glu Ala Trp Lys Ser Phe Leu Glu Asn Pro Leu Thr Ala Ala Thr Lys
                35                  40                  45 gcg atg atg agc atc aat gga gat gaa gac agc gcc gct gcg ctg ggc       192
Ala Met Met Ser Ile Asn Gly Asp Glu Asp Ser Ala Ala Ala Leu Gly
            50                  55                  60 ctc ctc tat gac tac tac aag gtt cca aga gag aga agg tca tca aca       240
Leu Leu Tyr Asp Tyr Tyr Lys Val Pro Arg Glu Arg Arg Ser Ser Thr
        65                  70                  75 gca aag cca gag gtg gag cac cct gag cca gat cac agc aaa aga aac       288
Ala Lys Pro Glu Val Glu His Pro Glu Pro Asp His Ser Lys Arg Asn
80                  85                  90 agc ata cca att gtg aca gag cag ccc ctc atc tct gct gga gaa aac       336
Ser Ile Pro Ile Val Thr Glu Gln Pro Leu Ile Ser Ala Gly Glu Asn
95                  100                 105                 110 aga gtg caa gta ctg aaa aat gtg cca ttt aac att gtc ctt ccc cat       384
Arg Val Gln Val Leu Lys Asn Val Pro Phe Asn Ile Val Leu Pro His
                115                 120                 125 ggc aac cag ctg ggc att gat aag aga ggc cat ctg aca gct tca gat       432
Gly Asn Gln Leu Gly Ile Asp Lys Arg Gly His Leu Thr Ala Ser Asp
            130                 135                 140 acg aca gtc act gtc tcc ata gca acg atg cct acc cac tcc atc aag       480
Thr Thr Val Thr Val Ser Ile Ala Thr Met Pro Thr His Ser Ile Lys
        145                 150                 155 aca gaa acc cag cca cat ggc ttc gct gtg gga atc ccc cca gca gtg       528
Thr Glu Thr Gln Pro His Gly Phe Ala Val Gly Ile Pro Pro Ala Val
160                 165                 170
```

-continued

```
tat cat cct gag ccc act gag cgg gtg gtg gtt ttc gat cgg aay ctc      576
Tyr His Pro Glu Pro Thr Glu Arg Val Val Val Phe Asp Arg Asn Leu
175             180                 185                 190 aat act gac cag ttc agc tct ggt gct caa gcc cca aat gct caa agg      624
Asn Thr Asp Gln Phe Ser Ser Gly Ala Gln Ala Pro Asn Ala Gln Arg
            195                 200                 205 cga act cca gac tcg acc ttc tca gag acc ttc aag gaa ggc gtt cag      672
Arg Thr Pro Asp Ser Thr Phe Ser Glu Thr Phe Lys Glu Gly Val Gln
        210                 215                 220 gag gtt ttc ttc ccc tcg gat ctc agt ctg cgg atg cct ggc atg aat      720
Glu Val Phe Phe Pro Ser Asp Leu Ser Leu Arg Met Pro Gly Met Asn
    225                 230                 235 tca gag gac tat gtt ttt gac agt gtt tct ggg aac aac ttt gaa tat      768
Ser Glu Asp Tyr Val Phe Asp Ser Val Ser Gly Asn Asn Phe Glu Tyr
240                 245                 250 acc cta gaa gct tca aaa tca ctt cga cag aag cca gga gac agt acc      816
Thr Leu Glu Ala Ser Lys Ser Leu Arg Gln Lys Pro Gly Asp Ser Thr
255                 260                 265                 270 atg acg tac ctg aac aaa ggc cag ttc tat ccc atc acc ttg aag gag      864
Met Thr Tyr Leu Asn Lys Gly Gln Phe Tyr Pro Ile Thr Leu Lys Glu
            275                 280                 285 gtg agc agc agt gaa gga atc cat cat ccc atc agc aaa gtt cga agt      912
Val Ser Ser Ser Glu Gly Ile His His Pro Ile Ser Lys Val Arg Ser
        290                 295                 300 gtg atc atg gtg gtt ttt gct gaa gac aaa agc aga gaa gat cag tta      960
Val Ile Met Val Val Phe Ala Glu Asp Lys Ser Arg Glu Asp Gln Leu
    305                 310                 315 agg cat tgg aag tac tgg cac tcc cgg cag cac acc gct aaa caa aga     1008
Arg His Trp Lys Tyr Trp His Ser Arg Gln His Thr Ala Lys Gln Arg
320                 325                 330 tgc att gac ata gct gac tat awa gaa agc ttc aac act atc agt aac     1056
Cys Ile Asp Ile Ala Asp Tyr Xaa Glu Ser Phe Asn Thr Ile Ser Asn
335                 340                 345                 350 atc gag gag att gcg tat aac gcc att tcc ttc aca tgg gac atc aac     1104
Ile Glu Glu Ile Ala Tyr Asn Ala Ile Ser Phe Thr Trp Asp Ile Asn
            355                 360                 365 gat gaa gca aag gtt ttc atc tct gtg aac tgc tta agc aca gat ttc     1152
Asp Glu Ala Lys Val Phe Ile Ser Val Asn Cys Leu Ser Thr Asp Phe
        370                 375                 380 tct tcc cag aag gga gtg aag ggg ttg cct ctt aac att caa gtt gat     1200
Ser Ser Gln Lys Gly Val Lys Gly Leu Pro Leu Asn Ile Gln Val Asp
    385                 390                 395 acc tat agt tac aac aac cgc agc aac aag cct gtg cac cgg gcc tac     1248
Thr Tyr Ser Tyr Asn Asn Arg Ser Asn Lys Pro Val His Arg Ala Tyr
400                 405                 410 tgc cag atc aag gtc ttc tgt gac aag gga gct gag cgg aaa atc agg     1296
Cys Gln Ile Lys Val Phe Cys Asp Lys Gly Ala Glu Arg Lys Ile Arg
415                 420                 425                 430 gat gaa gaa cga aag caa agc aaa aga aaa gtt tct gat gtt aaa gtg     1344
Asp Glu Glu Arg Lys Gln Ser Lys Arg Lys Val Ser Asp Val Lys Val
            435                 440                 445 cca ctg ctt ccc tct cac aag cga atg gat atc aca gtt ttc aaa ccc     1392
Pro Leu Leu Pro Ser His Lys Arg Met Asp Ile Thr Val Phe Lys Pro
        450                 455                 460 ttc att gat ctc gat act cag cct gtc ctc ttc att cct gac gtg cac     1440
Phe Ile Asp Leu Asp Thr Gln Pro Val Leu Phe Ile Pro Asp Val His
    465                 470                 475 ttt gcc aac ttg cag cgg ggc act cat gtc ctt ccc att gcc tct gaa     1488
Phe Ala Asn Leu Gln Arg Gly Thr His Val Leu Pro Ile Ala Ser Glu
```

-continued

```
                480                 485                 490
gaa ttg gag ggt gaa ggc tct gtc ttg aaa agg ggg ccg tac ggc aca      1536
Glu Leu Glu Gly Glu Gly Ser Val Leu Lys Arg Gly Pro Tyr Gly Thr
495                 500                 505                 510 gaa gat gac ttt gct gtc cct cct tct acc aag ctg gcc cgg ata gaa      1584
Glu Asp Asp Phe Ala Val Pro Pro Ser Thr Lys Leu Ala Arg Ile Glu
                515                 520                 525 gaa cca aag aga gtg ctg ctc tac gtt cga aag gag tca gaa gaa gtc      1632
Glu Pro Lys Arg Val Leu Leu Tyr Val Arg Lys Glu Ser Glu Glu Val
            530                 535                 540 ttt gat gcc ctg atg ctc aaa acc cca tct ttg aag ggc ttg atg gaa      1680
Phe Asp Ala Leu Met Leu Lys Thr Pro Ser Leu Lys Gly Leu Met Glu
        545                 550                 555 gct atc tca gac aaa tac gat gtt ccc cat gac aag att ggg aaa ata      1728
Ala Ile Ser Asp Lys Tyr Asp Val Pro His Asp Lys Ile Gly Lys Ile
    560                 565                 570 ttc aag aag tgt aaa aag ggg atc ctg gtg aac atg gac gac aac att      1776
Phe Lys Lys Cys Lys Lys Gly Ile Leu Val Asn Met Asp Asp Asn Ile
575                 580                 585                 590 gtg aag cat tac tcc aat gag gac acc ttc cag ctg cag att gaa gaa      1824
Val Lys His Tyr Ser Asn Glu Asp Thr Phe Gln Leu Gln Ile Glu Glu
                595                 600                 605 gcc ggg ggg tct tac aag ctc acc ctg acg gag atc taaaggcctg           1870
Ala Gly Gly Ser Tyr Lys Leu Thr Leu Thr Glu Ile
            610                 615 cgggccacag ctccccagga gttcagtgca ggtgtttcta gatcttacgg tttggcaact    1930
gcaggtaacc ccagtcagcc atgtcgccag cacaggtcta tgtcgaggga atgggttcct    1990
tgcaggttgg aggcggggct gcatctggct tggtggtagc atttaatcta ttgcattggt    2050 gttttttcaga tgaaagagaa atccatatac cattatgttt gaatttcctg atatatacag   2110
gatttaaagt gaaaacttta ttccaagagt taacagagtc tctgggaagc tttaggacat    2170
ctgctacgtt atttatcaaa atattgggat ctctgccttg tgcctacagt gtcgtgggcc    2230
tgctcgctag cagaagtcag aaaaggcgat aggcttggct ttaaggattt cgtgcccttg    2290
cctgaattca gtacaactcc actgcctcac gttagcggga gcgcacctga agagtacggg    2350
gggagccctc t                                                         2361
```

<210> SEQ ID NO 4
<211> LENGTH: 618
<212> TYPE: PRT
<213> ORGANISM: human
<220> FEATURE:
<221> NAME/KEY: misc_feature
<222> LOCATION: (342)..(342)
<223> OTHER INFORMATION: The 'Xaa' at location 342 stands for Lys, or
      Ile.

<400> SEQUENCE: 4

```
Met Thr Gln Glu Tyr Asp Asn Lys Arg Pro Val Leu Val Leu Gln Asn
1               5                   10                  15

Glu Ala Leu Tyr Pro Gln Arg Arg Ser Tyr Thr Ser Glu Asp Glu Ala
                20                  25                  30

Trp Lys Ser Phe Leu Glu Asn Pro Leu Thr Ala Ala Thr Lys Ala Met
            35                  40                  45

Met Ser Ile Asn Gly Asp Glu Asp Ser Ala Ala Ala Leu Gly Leu Leu
        50                  55                  60

Tyr Asp Tyr Tyr Lys Val Pro Arg Glu Arg Arg Ser Ser Thr Ala Lys
65                  70                  75                  80
```

```
Pro Glu Val Glu His Pro Glu Pro Asp His Ser Lys Arg Asn Ser Ile
                85                  90                  95

Pro Ile Val Thr Glu Gln Pro Leu Ile Ser Ala Gly Glu Asn Arg Val
            100                 105                 110

Gln Val Leu Lys Asn Val Pro Phe Asn Ile Val Leu Pro His Gly Asn
        115                 120                 125

Gln Leu Gly Ile Asp Lys Arg Gly His Leu Thr Ala Ser Asp Thr Thr
    130                 135                 140

Val Thr Val Ser Ile Ala Thr Met Pro Thr His Ser Ile Lys Thr Glu
145                 150                 155                 160

Thr Gln Pro His Gly Phe Ala Val Gly Ile Pro Pro Ala Val Tyr His
                165                 170                 175

Pro Glu Pro Thr Glu Arg Val Val Phe Asp Arg Asn Leu Asn Thr
            180                 185                 190

Asp Gln Phe Ser Ser Gly Ala Gln Pro Asn Ala Gln Arg Arg Thr
        195                 200                 205

Pro Asp Ser Thr Phe Ser Glu Thr Phe Lys Glu Gly Val Gln Glu Val
    210                 215                 220

Phe Phe Pro Ser Asp Leu Ser Leu Arg Met Pro Gly Met Asn Ser Glu
225                 230                 235                 240

Asp Tyr Val Phe Asp Ser Val Ser Gly Asn Asn Phe Glu Tyr Thr Leu
                245                 250                 255

Glu Ala Ser Lys Ser Leu Arg Gln Lys Pro Gly Asp Ser Thr Met Thr
            260                 265                 270

Tyr Leu Asn Lys Gly Gln Phe Tyr Pro Ile Thr Leu Lys Glu Val Ser
        275                 280                 285

Ser Ser Glu Gly Ile His His Pro Ile Ser Lys Val Arg Ser Val Ile
    290                 295                 300

Met Val Val Phe Ala Glu Asp Lys Ser Arg Glu Asp Gln Leu Arg His
305                 310                 315                 320

Trp Lys Tyr Trp His Ser Arg Gln His Thr Ala Lys Gln Arg Cys Ile
                325                 330                 335

Asp Ile Ala Asp Tyr Xaa Glu Ser Phe Asn Thr Ile Ser Asn Ile Glu
            340                 345                 350

Glu Ile Ala Tyr Asn Ala Ile Ser Phe Thr Trp Asp Ile Asn Asp Glu
        355                 360                 365

Ala Lys Val Phe Ile Ser Val Asn Cys Leu Ser Thr Asp Phe Ser Ser
370                 375                 380

Gln Lys Gly Val Lys Gly Leu Pro Leu Asn Ile Gln Val Asp Thr Tyr
385                 390                 395                 400

Ser Tyr Asn Asn Arg Ser Asn Lys Pro Val His Arg Ala Tyr Cys Gln
            405                 410                 415

Ile Lys Val Phe Cys Asp Lys Gly Ala Glu Arg Lys Ile Arg Asp Glu
        420                 425                 430

Glu Arg Lys Gln Ser Lys Arg Lys Val Ser Asp Val Lys Val Pro Leu
    435                 440                 445

Leu Pro Ser His Lys Arg Met Asp Ile Thr Val Phe Lys Pro Phe Ile
450                 455                 460

Asp Leu Asp Thr Gln Pro Val Leu Phe Ile Pro Asp Val His Phe Ala
465                 470                 475                 480

Asn Leu Gln Arg Gly Thr His Val Leu Pro Ile Ala Ser Glu Glu Leu
                485                 490                 495
```

```
Glu Gly Glu Gly Ser Val Leu Lys Arg Gly Pro Tyr Gly Thr Glu Asp
            500                 505                 510

Asp Phe Ala Val Pro Pro Ser Thr Lys Leu Ala Arg Ile Glu Glu Pro
        515                 520                 525

Lys Arg Val Leu Leu Tyr Val Arg Lys Glu Ser Glu Glu Val Phe Asp
    530                 535                 540

Ala Leu Met Leu Lys Thr Pro Ser Leu Lys Gly Leu Met Glu Ala Ile
545                 550                 555                 560

Ser Asp Lys Tyr Asp Val Pro His Asp Lys Ile Gly Lys Ile Phe Lys
                565                 570                 575

Lys Cys Lys Lys Gly Ile Leu Val Asn Met Asp Asn Ile Val Lys
            580                 585                 590

His Tyr Ser Asn Glu Asp Thr Phe Gln Leu Gln Ile Glu Glu Ala Gly
        595                 600                 605

Gly Ser Tyr Lys Leu Thr Leu Thr Glu Ile
    610                 615

<210> SEQ ID NO 5
<211> LENGTH: 4532
<212> TYPE: DNA
<213> ORGANISM: human
<220> FEATURE:
<221> NAME/KEY: CDS
<222> LOCATION: (67)..(1941)

<400> SEQUENCE: 5
ttgaaagtcc agtttcacca gaggctgagg ctccaggaaa aggggagcaa gttcattgga        60 tcaaac atg tca caa gag tca gac aat aat aaa aga cta gtg gcc tta         108
       Met Ser Gln Glu Ser Asp Asn Asn Lys Arg Leu Val Ala Leu
         1               5                  10 gtg ccc atg ccc agt gac cct cca ttc aat acc cga aga gcc tac acc       156
Val Pro Met Pro Ser Asp Pro Pro Phe Asn Thr Arg Arg Ala Tyr Thr
 15              20                  25                  30 agt gag gat gaa gcc tgg aag tca tac ttg gag aat ccc ctg aca gca       204
Ser Glu Asp Glu Ala Trp Lys Ser Tyr Leu Glu Asn Pro Leu Thr Ala
                 35                  40                  45 gcc acc aag gcc atg atg agc att aat ggt gat gag gac agt gct gct       252
Ala Thr Lys Ala Met Met Ser Ile Asn Gly Asp Glu Asp Ser Ala Ala
             50                  55                  60 gcc ctc ggc ctg ctc tat gac tac tac aag gtt cct cga gac aag agg       300
Ala Leu Gly Leu Leu Tyr Asp Tyr Tyr Lys Val Pro Arg Asp Lys Arg
         65                  70                  75 ctg ctg tct gta agc aaa gca agt gac agc caa gaa gac cag gag aaa       348
Leu Leu Ser Val Ser Lys Ala Ser Asp Ser Gln Glu Asp Gln Glu Lys
     80                  85                  90 aga aac tgc ctt ggc acc agt gaa gcc cag agt aat ttg agt gga gga       396
Arg Asn Cys Leu Gly Thr Ser Glu Ala Gln Ser Asn Leu Ser Gly Gly
 95                 100                 105                 110 gaa aac cga gtg caa gtc cta aag act gtt cca gtg aac ctt tcc cta       444
Glu Asn Arg Val Gln Val Leu Lys Thr Val Pro Val Asn Leu Ser Leu
                115                 120                 125 aat caa gat cac ctg gag aat tcc aag cgg gaa cag tac agc atc agc       492
Asn Gln Asp His Leu Glu Asn Ser Lys Arg Glu Gln Tyr Ser Ile Ser
            130                 135                 140 ttc ccc gag agc tct gcc atc atc ccg gtg tcg gga atc acg gtg gtg       540
Phe Pro Glu Ser Ser Ala Ile Ile Pro Val Ser Gly Ile Thr Val Val
        145                 150                 155 aaa gct gaa gat ttc aca cca gtt ttc atg gcc cca cct gtg cac tat       588
Lys Ala Glu Asp Phe Thr Pro Val Phe Met Ala Pro Pro Val His Tyr
```

```
                    160                 165                 170
ccc cgg gga gat ggg gaa gag caa cga gtg gtt atc ttt gaa cag act       636
Pro Arg Gly Asp Gly Glu Glu Gln Arg Val Val Ile Phe Glu Gln Thr
175                 180                 185                 190 cag tat gac gtg ccc tcg ctg gcc acc cac agc gcc tat ctc aaa gac       684
Gln Tyr Asp Val Pro Ser Leu Ala Thr His Ser Ala Tyr Leu Lys Asp
            195                 200                 205 gac cag cgc agc act ccg gac agc aca tac agc gag agc ttc aag gac       732
Asp Gln Arg Ser Thr Pro Asp Ser Thr Tyr Ser Glu Ser Phe Lys Asp
        210                 215                 220 gca gcc aca gag aaa ttt cgg agt gct tca gtt ggg gct gag gag tac       780
Ala Ala Thr Glu Lys Phe Arg Ser Ala Ser Val Gly Ala Glu Glu Tyr
    225                 230                 235 atg tat gat cag aca tca agt ggc aca ttt cag tac acc ctg gaa gcc       828
Met Tyr Asp Gln Thr Ser Ser Gly Thr Phe Gln Tyr Thr Leu Glu Ala
240                 245                 250 acc aaa tct ctc cgt cag aag cag ggg gag ggc ccc atg acc tac ctc       876
Thr Lys Ser Leu Arg Gln Lys Gln Gly Glu Gly Pro Met Thr Tyr Leu
255                 260                 265                 270 aac aaa gga cag ttc tat gcc ata aca ctc agc gag acc gga gac aac       924
Asn Lys Gly Gln Phe Tyr Ala Ile Thr Leu Ser Glu Thr Gly Asp Asn
            275                 280                 285 aaa tgc ttc cga cac ccc atc agc aaa gtc agg agt gtg gtg atg gtg       972
Lys Cys Phe Arg His Pro Ile Ser Lys Val Arg Ser Val Val Met Val
        290                 295                 300 gtc ttc agt gaa gac aaa aac aga gat gaa cag ctc aaa tac tgg aaa      1020
Val Phe Ser Glu Asp Lys Asn Arg Asp Glu Gln Leu Lys Tyr Trp Lys
    305                 310                 315 tac tgg cac tct cgg cag cat acg gcg aag cag agg gtc ctt gac att      1068
Tyr Trp His Ser Arg Gln His Thr Ala Lys Gln Arg Val Leu Asp Ile
320                 325                 330 gcc gat tac aag gag agc ttt aat acg att gga aac att gaa gag att      1116
Ala Asp Tyr Lys Glu Ser Phe Asn Thr Ile Gly Asn Ile Glu Glu Ile
335                 340                 345                 350 gca tat aat gct gtt tcc ttt acc tgg gac gtg aat gaa gag gcg aag      1164
Ala Tyr Asn Ala Val Ser Phe Thr Trp Asp Val Asn Glu Glu Ala Lys
            355                 360                 365 att ttc atc acc gtg aat tgc ttg agc aca gat ttc tcc tcc caa aaa      1212
Ile Phe Ile Thr Val Asn Cys Leu Ser Thr Asp Phe Ser Ser Gln Lys
        370                 375                 380 ggg gtg aaa gga ctt cct ttg atg att cag att gac aca tac agt tat      1260
Gly Val Lys Gly Leu Pro Leu Met Ile Gln Ile Asp Thr Tyr Ser Tyr
    385                 390                 395 aac aat cgt agc aat aaa ccc att cat aga gct tat tgc cag atc aag      1308
Asn Asn Arg Ser Asn Lys Pro Ile His Arg Ala Tyr Cys Gln Ile Lys
400                 405                 410 gtc ttc tgt gac aaa gga gca gaa aga aaa atc cga gat gaa gag cgg      1356
Val Phe Cys Asp Lys Gly Ala Glu Arg Lys Ile Arg Asp Glu Glu Arg
415                 420                 425                 430 aag cag aac agg aag aaa ggg aaa ggc cag gcc tcc caa act caa tgc      1404
Lys Gln Asn Arg Lys Lys Gly Lys Gly Gln Ala Ser Gln Thr Gln Cys
            435                 440                 445 aac agc tcc tct gat ggg aag ttg gct gcc ata cct tta cag aag aag      1452
Asn Ser Ser Ser Asp Gly Lys Leu Ala Ala Ile Pro Leu Gln Lys Lys
        450                 455                 460 agt gac atc acc tac ttc aaa acc atg cct gat ctc cac tca cag cca      1500
Ser Asp Ile Thr Tyr Phe Lys Thr Met Pro Asp Leu His Ser Gln Pro
    465                 470                 475 gtt ctc ttc ata cct gat gtt cac ttt gca aac ctg cag agg acc gga      1548
Val Leu Phe Ile Pro Asp Val His Phe Ala Asn Leu Gln Arg Thr Gly
```

```
                Val Leu Phe Ile Pro Asp Val His Phe Ala Asn Leu Gln Arg Thr Gly
                    480                 485                 490 cag gtg tat tac aac acg gat gat gaa cga gaa ggt ggc agt gtc ctt           1596
Gln Val Tyr Tyr Asn Thr Asp Asp Glu Arg Glu Gly Gly Ser Val Leu
495                 500                 505                 510 gtt aaa cgg atg ttc cgg ccc atg gaa gag gag ttt ggt cca gtg cct           1644
Val Lys Arg Met Phe Arg Pro Met Glu Glu Glu Phe Gly Pro Val Pro
                515                 520                 525 tca aag cag atg aaa gaa gaa ggg aca aag cga gtg ctc ttg tac gtg           1692
Ser Lys Gln Met Lys Glu Glu Gly Thr Lys Arg Val Leu Leu Tyr Val
            530                 535                 540 agg aag gag act gac gat gtg ttc gat gca ttg atg ttg aag tct ccc           1740
Arg Lys Glu Thr Asp Asp Val Phe Asp Ala Leu Met Leu Lys Ser Pro
        545                 550                 555 aca gtg aag ggc ctg atg gaa gcg ata tct gag aaa tat ggg ctg ccc           1788
Thr Val Lys Gly Leu Met Glu Ala Ile Ser Glu Lys Tyr Gly Leu Pro
    560                 565                 570 gtg gag aag ata gca aag ctt tac aag aaa agc aaa aaa ggc atc ttg           1836
Val Glu Lys Ile Ala Lys Leu Tyr Lys Lys Ser Lys Lys Gly Ile Leu
575                 580                 585                 590 gtg aac atg gat gac aac atc atc gag cac tac tcg aac gag gac acc           1884
Val Asn Met Asp Asp Asn Ile Ile Glu His Tyr Ser Asn Glu Asp Thr
                595                 600                 605 ttc atc ctc aac atg gag agc atg gtg gag ggc ttc aag gtc acg ctc           1932
Phe Ile Leu Asn Met Glu Ser Met Val Glu Gly Phe Lys Val Thr Leu
                610                 615                 620 atg gaa atc tagccctggg tttggcatcc gctttggctg gagctctcag                   1981
Met Glu Ile
        625 tgcgttcctc cctgagagag acagaagccc cagccccaga acctggagac ccatctcccc        2041 catctcacaa ctgctgttac aagaccgtgc tggggagtgg ggcaagggac aggcccccact       2101 gtcggtgtgc ttggcccatc cactggcacc taccacggga ctgaagcctg agcccctcag        2161 gaaggtgcct taggcctgtt ggattcctat ttattgccca ccttttcctg gagcccaggt        2221 ccaggcccgc caggactctg caggtcactg ctagctccag atgagaccgt ccagcgttcc        2281 cccttcaaga gaaacactca tcccgaacag cctaaaaaat tcccatccct tctctctcac        2341 ccctccatat ctatctcccg agtggctgga caaaatgagc tacgtctggg tgcagtagtt       2401 ataggtgggg caagaggtgg atgcccactt tctggtcaga cacctttagg ttgctctggg       2461 gaaggctgtc ttgctaaata cctccagggt tcccagcaag tggccaccag gccttgtaca      2521 ggaagacatt cagtcaccgt gtaattagta acacagaaag tctgcctgtc tgcattgtac      2581 atagtgttta taatattgta ataatatatt ttacctgtgg tatgtgggca tgtttactgc      2641 cactggcctt agaggagaca cagacctgga gaccgtttta atgggggttt ttgcctctgt      2701 gcctgttcaa gagacttgca gggctaggta gagggccttt gggatgttaa ggtgactgca      2761 gctgatgcca agatggactc tgcaatgggc atacctgggg gctcgttccc tgtccccaga      2821 ggaagccccc tctccttctc catgggcatg actctccttc gaggccacca cgtttatctc      2881 acaatgatgt gttttgcttg actttccctt tgcgctgtct cgtgggaaag gtcattctgt      2941 ctgagacccc agctccttct ccagctttgg ctgcgggcat ggcctgagct ttctggagag      3001 cctctgcagg gggtttgcca tcagggccct gtggctgggt ctgctgcaga gctccttggc      3061 tatcaggaga atcctggaca ctgtactgtg cctcccagtt tacaaacacg cccttcatct      3121 caagtggccc tttaaaaggc ctgctgccat gtgagagctg tgaacagctc agctctgagt      3181
```

```
cggcaggctg gggcttcctc ctgggccacc agatggaaag ggggtattgt ttgcctcact    3241
cctggatgct gcgttttaag gaagtgagtg agaaagaatg tgccaagata cctggctcct    3301
gtgaaaccag cctcaggagg gaaactggga gagagaagct gtggtctcct gctacatgcc    3361
ctgggagctg gaagagaaaa acactcccct aaacaatcgc aaaatgatga accatcatgg    3421
gccactgttc tctttgaggg gacaggttta ggggtttgcg ttcgcccttg tgggctgaag    3481
cactagcttt ttggtagcta gacacatcct gcacccaaag gttctctaca aaggcccaga    3541 tttgttttgta aagcactttg actcttacct ggaggcccgc tctctaaggg cttcctgcgc    3601
tcccacctca tctgtccctg agatgcagag caggatggag ggtctgcttc tagctcagct    3661
gtttctcctt gaggttgcgg aggaattgaa ttgaatggga cagagggcag gtgctgtggc    3721
caagaagatc tccgagcagc agtgacgggg caccttgctg tgtgtcctct gggcatgtta    3781
acccttctgt ggggccaaag gtttgcatcg tggatccagc tgtgctccag tctgtcccct    3841
cctcctccac tctgactgcc acgccccgga ccagcagctt ggggaccctc cagggtacta    3901
atggggctct gttctgagat ggacaaattc agtgttggaa atacatgttg tactatgcac    3961
ttcccatgct cctagggtta ggaatagttt caaacatgat tggcagacat aacaacggca    4021
aatactcgga ctggggcata ggactccaga gtaggaaaaa gacaaaagat ttggcagcct    4081
gacacaggca acctacccct ctctctccag cctctttatg aaactgtttg tttgccagtc    4141
ctgccctaag gcagaagatg aattgaagat gctgtgcatg tttcctaagt ccttgagcaa    4201
tcatggtggt gacaattgcc acaagggata tgaggccagt gccaccagag ggtggtgcca    4261
agtgccacat cccttccgat ccattcccct ctgcatcctc ggagcacccc agtttgcctt    4321
tgatgtgtcc gctgtgtatg ttagctgaac tttgatgagc aaaatttcct gagcgaaaca    4381
ctccaaagag ataggaaaac ttgccgcctc ttcttttttg tcccttaatc aaactcaaat    4441
aagcttaaaa aaaatccatg gaagatcatg gacatgtgaa atgagcattt ttttcttttt    4501
tttttttttt tttaacaaag tctgaactga g                                   4532
```

<210> SEQ ID NO 6
<211> LENGTH: 625
<212> TYPE: PRT
<213> ORGANISM: human

<400> SEQUENCE: 6

```
Met Ser Gln Glu Ser Asp Asn Asn Lys Arg Leu Val Ala Leu Val Pro
1               5                   10                  15

Met Pro Ser Asp Pro Pro Phe Asn Thr Arg Arg Ala Tyr Thr Ser Glu
                20                  25                  30

Asp Glu Ala Trp Lys Ser Tyr Leu Glu Asn Pro Leu Thr Ala Ala Thr
            35                  40                  45

Lys Ala Met Met Ser Ile Asn Gly Asp Glu Asp Ser Ala Ala Ala Leu
        50                  55                  60

Gly Leu Leu Tyr Asp Tyr Tyr Lys Val Pro Arg Asp Lys Arg Leu Leu
65                  70                  75                  80

Ser Val Ser Lys Ala Ser Asp Ser Gln Glu Asp Gln Glu Lys Arg Asn
                85                  90                  95

Cys Leu Gly Thr Ser Glu Ala Gln Ser Asn Leu Ser Gly Gly Glu Asn
                100                 105                 110

Arg Val Gln Val Leu Lys Thr Val Pro Val Asn Leu Ser Leu Asn Gln
            115                 120                 125

Asp His Leu Glu Asn Ser Lys Arg Glu Gln Tyr Ser Ile Ser Phe Pro
```

```
            130                 135                 140
Glu Ser Ser Ala Ile Ile Pro Val Ser Gly Ile Thr Val Val Lys Ala
145                 150                 155                 160

Glu Asp Phe Thr Pro Val Phe Met Ala Pro Val His Tyr Pro Arg
                165                 170                 175

Gly Asp Gly Glu Glu Gln Arg Val Val Ile Phe Glu Gln Thr Gln Tyr
                180                 185                 190

Asp Val Pro Ser Leu Ala Thr His Ser Ala Tyr Leu Lys Asp Asp Gln
                195                 200                 205

Arg Ser Thr Pro Asp Ser Thr Tyr Ser Glu Ser Phe Lys Asp Ala Ala
210                 215                 220

Thr Glu Lys Phe Arg Ser Ala Ser Val Gly Ala Glu Glu Tyr Met Tyr
225                 230                 235                 240

Asp Gln Thr Ser Ser Gly Thr Phe Gln Tyr Thr Leu Glu Ala Thr Lys
                245                 250                 255

Ser Leu Arg Gln Lys Gln Gly Glu Gly Pro Met Thr Tyr Leu Asn Lys
                260                 265                 270

Gly Gln Phe Tyr Ala Ile Thr Leu Ser Glu Thr Gly Asp Asn Lys Cys
                275                 280                 285

Phe Arg His Pro Ile Ser Lys Val Arg Ser Val Val Met Val Val Phe
                290                 295                 300

Ser Glu Asp Lys Asn Arg Asp Glu Gln Leu Lys Tyr Trp Lys Tyr Trp
305                 310                 315                 320

His Ser Arg Gln His Thr Ala Lys Gln Arg Val Leu Asp Ile Ala Asp
                325                 330                 335

Tyr Lys Glu Ser Phe Asn Thr Ile Gly Asn Ile Glu Glu Ile Ala Tyr
                340                 345                 350

Asn Ala Val Ser Phe Thr Trp Asp Val Asn Glu Glu Ala Lys Ile Phe
                355                 360                 365

Ile Thr Val Asn Cys Leu Ser Thr Asp Phe Ser Ser Gln Lys Gly Val
                370                 375                 380

Lys Gly Leu Pro Leu Met Ile Gln Ile Asp Thr Tyr Ser Tyr Asn Asn
385                 390                 395                 400

Arg Ser Asn Lys Pro Ile His Arg Ala Tyr Cys Gln Ile Lys Val Phe
                405                 410                 415

Cys Asp Lys Gly Ala Glu Arg Lys Ile Arg Asp Glu Glu Arg Lys Gln
                420                 425                 430

Asn Arg Lys Lys Gly Lys Gly Gln Ala Ser Gln Thr Gln Cys Asn Ser
                435                 440                 445

Ser Ser Asp Gly Lys Leu Ala Ala Ile Pro Leu Gln Lys Lys Ser Asp
                450                 455                 460

Ile Thr Tyr Phe Lys Thr Met Pro Asp Leu His Ser Gln Pro Val Leu
465                 470                 475                 480

Phe Ile Pro Asp Val His Phe Ala Asn Leu Gln Arg Thr Gly Gln Val
                485                 490                 495

Tyr Tyr Asn Thr Asp Asp Glu Arg Glu Gly Gly Ser Val Leu Val Lys
                500                 505                 510

Arg Met Phe Arg Pro Met Glu Glu Phe Gly Pro Val Pro Ser Lys
                515                 520                 525

Gln Met Lys Glu Glu Gly Thr Lys Arg Val Leu Leu Tyr Val Arg Lys
                530                 535                 540

Glu Thr Asp Asp Val Phe Asp Ala Leu Met Leu Lys Ser Pro Thr Val
545                 550                 555                 560
```

```
                Lys Gly Leu Met Glu Ala Ile Ser Glu Lys Tyr Gly Leu Pro Val Glu
                            565                 570                 575

Lys Ile Ala Lys Leu Tyr Lys Lys Ser Lys Lys Gly Ile Leu Val Asn
                        580                 585                 590

Met Asp Asp Asn Ile Ile Glu His Tyr Ser Asn Glu Asp Thr Phe Ile
                    595                 600                 605

Leu Asn Met Glu Ser Met Val Glu Gly Phe Lys Val Thr Leu Met Glu
                        610                 615                 620

Ile
                625

<210> SEQ ID NO 7
<211> LENGTH: 1870
<212> TYPE: DNA
<213> ORGANISM: HUMAN
<220> FEATURE:
<221> NAME/KEY: CDS
<222> LOCATION: (47)..(1867)
<220> FEATURE:
<221> NAME/KEY: VARIANT
<222> LOCATION: 117
<223> OTHER INFORMATION: Xaa = Phe, Leu
<220> FEATURE:
<221> NAME/KEY: VARIANT
<222> LOCATION: 172
<223> OTHER INFORMATION: Xaa = Thr

<400> SEQUENCE: 7
aggagatgtg ccaaactgtt aagagtggtt atttctgagc agaaga atg tgg atg            55
                                                  Met Trp Met
                                                    1 aat tcc att ctt cct att ttt ctt ttc agg tct gtg cgg ctg cta aag         103
Asn Ser Ile Leu Pro Ile Phe Leu Phe Arg Ser Val Arg Leu Leu Lys
   5                  10                  15 aac gac cca gtc aac ttg cag aaa ttc tct tac act agt gag gat gag         151
Asn Asp Pro Val Asn Leu Gln Lys Phe Ser Tyr Thr Ser Glu Asp Glu
 20                  25                  30                  35 gcc tgg aag acg tac cta gaa aac ccg ttg aca gct gcc aca aag gcc         199
Ala Trp Lys Thr Tyr Leu Glu Asn Pro Leu Thr Ala Ala Thr Lys Ala
                 40                  45                  50 atg atg aga gtc aat gga gat gat gac agt gtt gcg gcc ttg agc ttc         247
Met Met Arg Val Asn Gly Asp Asp Asp Ser Val Ala Ala Leu Ser Phe
             55                  60                  65 ctc tat gat tac tac atg ggt ccc aag gag aag cgg ata ttg tcc tcc         295
Leu Tyr Asp Tyr Tyr Met Gly Pro Lys Glu Lys Arg Ile Leu Ser Ser
         70                  75                  80 agc act ggg ggc agg aat gac caa gga aag agg tac tac cat ggc atg         343
Ser Thr Gly Gly Arg Asn Asp Gln Gly Lys Arg Tyr Tyr His Gly Met
     85                  90                  95 gaa tat gag acg gac ctc act ccc ctt gaa agc ccc aca cac ctc atg         391
Glu Tyr Glu Thr Asp Leu Thr Pro Leu Glu Ser Pro Thr His Leu Met
100                 105                 110                 115 aaa ytc ctg aca gag aac gtg tct gga acc cca gag tac cca gat ttg         439
Lys Xaa Leu Thr Glu Asn Val Ser Gly Thr Pro Glu Tyr Pro Asp Leu
                 120                 125                 130 ctc aag aag aat aac ctg atg agc ttg gag ggg gcc ttg ccc acc cct         487
Leu Lys Lys Asn Asn Leu Met Ser Leu Glu Gly Ala Leu Pro Thr Pro
             135                 140                 145 ggc aag gca gct ccc ctc cct gca ggc ccc agc aag ctg gag gcc ggc         535
Gly Lys Ala Ala Pro Leu Pro Ala Gly Pro Ser Lys Leu Glu Ala Gly
         150                 155                 160
```

```
tct gtg gac agc tac ctg tta ccc acy act gat atg tat gat aat ggc      583
Ser Val Asp Ser Tyr Leu Leu Pro Xaa Thr Asp Met Tyr Asp Asn Gly
    165                 170                 175 tcc ctc aac tcc ttg ttt gag agc att cat ggg gtg ccg ccc aca cag      631
Ser Leu Asn Ser Leu Phe Glu Ser Ile His Gly Val Pro Pro Thr Gln
180                 185                 190                 195 cgc tgg cag cca gac agc acc ttc aaa gat gac cca cag gag tcg atg      679
Arg Trp Gln Pro Asp Ser Thr Phe Lys Asp Asp Pro Gln Glu Ser Met
                    200                 205                 210 ctc ttc cca gat atc ctg aaa acc tcc ccg gaa ccc cca tgt cca gag      727
Leu Phe Pro Asp Ile Leu Lys Thr Ser Pro Glu Pro Pro Cys Pro Glu
                215                 220                 225 gac tac ccc agc ctc aaa agt gac ttt gaa tac acc ctg ggc tcc ccc      775
Asp Tyr Pro Ser Leu Lys Ser Asp Phe Glu Tyr Thr Leu Gly Ser Pro
            230                 235                 240 aaa gcc atc cac atc aag tca ggc gag tca ccc atg gcc tac ctc aac      823
Lys Ala Ile His Ile Lys Ser Gly Glu Ser Pro Met Ala Tyr Leu Asn
        245                 250                 255 aaa ggc cag ttc tac ccc gtc acc ctg cgg acc cca gca ggt ggc aaa      871
Lys Gly Gln Phe Tyr Pro Val Thr Leu Arg Thr Pro Ala Gly Gly Lys
260                 265                 270                 275 ggc ctt gcc ttg tcc tcc aac aaa gtc aag agt gtg gtg atg gtt gtc      919
Gly Leu Ala Leu Ser Ser Asn Lys Val Lys Ser Val Val Met Val Val
                    280                 285                 290 ttc gac aat gag aag gtc cca gta gag cag ctg cgc ttc tgg aag cac      967
Phe Asp Asn Glu Lys Val Pro Val Glu Gln Leu Arg Phe Trp Lys His
                295                 300                 305 tgg cat tcc cgg caa ccc act gcc aag cag cgg gtc att gac gtg gct     1015
Trp His Ser Arg Gln Pro Thr Ala Lys Gln Arg Val Ile Asp Val Ala
            310                 315                 320 gac tgc aaa gaa aac ttc aac act gtg gag cac att gag gag gtg gcc     1063
Asp Cys Lys Glu Asn Phe Asn Thr Val Glu His Ile Glu Glu Val Ala
        325                 330                 335 tat aat gca ctg tcc ttt gtg tgg aac gtg aat gaa gag gcc aag gtg     1111
Tyr Asn Ala Leu Ser Phe Val Trp Asn Val Asn Glu Glu Ala Lys Val
340                 345                 350                 355 ttc atc ggc gta aac tgt ctg agc aca gac ttt tcc tca caa aag ggg     1159
Phe Ile Gly Val Asn Cys Leu Ser Thr Asp Phe Ser Ser Gln Lys Gly
                    360                 365                 370 gtg aag ggt gtc ccc ctg aac ctg cag att gac acc tat gac tgt ggc     1207
Val Lys Gly Val Pro Leu Asn Leu Gln Ile Asp Thr Tyr Asp Cys Gly
                375                 380                 385 ttg ggc act gag cgc ctg gta cac cgt gct gtc tgc cag atc aag atc     1255
Leu Gly Thr Glu Arg Leu Val His Arg Ala Val Cys Gln Ile Lys Ile
            390                 395                 400 ttc tgt gac aag gga gct gag agg aag atg cgc gat gac gag cgg aag     1303
Phe Cys Asp Lys Gly Ala Glu Arg Lys Met Arg Asp Asp Glu Arg Lys
        405                 410                 415 cag ttc cgg agg aag gtc aag tgc cct gac tcc agc aac agt ggc gtc     1351
Gln Phe Arg Arg Lys Val Lys Cys Pro Asp Ser Ser Asn Ser Gly Val
420                 425                 430                 435 aag ggc tgc ctg ctg tcg ggc ttc agg ggc aat gag acg acc tac ctt     1399
Lys Gly Cys Leu Leu Ser Gly Phe Arg Gly Asn Glu Thr Thr Tyr Leu
                    440                 445                 450 cgg cca gag act gac ctg gag acg cca ccc gtg ctg ttc atc ccc aat     1447
Arg Pro Glu Thr Asp Leu Glu Thr Pro Pro Val Leu Phe Ile Pro Asn
                455                 460                 465 gtg cac ttc tcc agc ctg cag cgc tct gga ggg gca gcc ccc tcg gca     1495
Val His Phe Ser Ser Leu Gln Arg Ser Gly Gly Ala Ala Pro Ser Ala
            470                 475                 480
```

```
gga ccc agc agc tcc aac agg ctg cct ctg aag cgt acc tgc tcg ccc    1543
Gly Pro Ser Ser Ser Asn Arg Leu Pro Leu Lys Arg Thr Cys Ser Pro
            485                 490                 495 ttc act gag gag ttt gag cct ctg ccc tcc aag cag gcc aag gaa ggc    1591
Phe Thr Glu Glu Phe Glu Pro Leu Pro Ser Lys Gln Ala Lys Glu Gly
500                 505                 510                 515 gac ctt cag aga gtt ctg ctg tat gtg cgg agg gag act gag gag gtg    1639
Asp Leu Gln Arg Val Leu Leu Tyr Val Arg Arg Glu Thr Glu Glu Val
                520                 525                 530 ttt gac gcg ctc atg ttg aag acc cca gac ctg aag ggg ctg agg aat    1687
Phe Asp Ala Leu Met Leu Lys Thr Pro Asp Leu Lys Gly Leu Arg Asn
            535                 540                 545 gcg atc tct gag aag tat ggg ttc cct gaa gag aac att tac aaa gtc    1735
Ala Ile Ser Glu Lys Tyr Gly Phe Pro Glu Glu Asn Ile Tyr Lys Val
        550                 555                 560 tac aag aaa tgc aag cga gga atc tta gtc aac atg gac aac aac atc    1783
Tyr Lys Lys Cys Lys Arg Gly Ile Leu Val Asn Met Asp Asn Asn Ile
    565                 570                 575 att cag cat tac agc aac cac gtc gcc ttc ctg ctg gac atg ggg gag    1831
Ile Gln His Tyr Ser Asn His Val Ala Phe Leu Leu Asp Met Gly Glu
580                 585                 590                 595 ctg gac ggc aaa att cag atc atc ctt aag gag ctg taa                1870
Leu Asp Gly Lys Ile Gln Ile Ile Leu Lys Glu Leu
                600                 605

<210> SEQ ID NO 8
<211> LENGTH: 607
<212> TYPE: PRT
<213> ORGANISM: HUMAN
<220> FEATURE:
<221> NAME/KEY: misc_feature
<222> LOCATION: (117)..(117)
<223> OTHER INFORMATION: The 'Xaa' at location 117 stands for Leu, or
      Phe.
<220> FEATURE:
<221> NAME/KEY: misc_feature
<222> LOCATION: (172)..(172)
<223> OTHER INFORMATION: The 'Xaa' at location 172 stands for Thr.

<400> SEQUENCE: 8

Met Trp Met Asn Ser Ile Leu Pro Ile Phe Leu Phe Arg Ser Val Arg
1               5                   10                  15

Leu Leu Lys Asn Asp Pro Val Asn Leu Gln Lys Phe Ser Tyr Thr Ser
            20                  25                  30

Glu Asp Glu Ala Trp Lys Thr Tyr Leu Glu Asn Pro Leu Thr Ala Ala
        35                  40                  45

Thr Lys Ala Met Met Arg Val Asn Gly Asp Asp Ser Val Ala Ala
    50                  55                  60

Leu Ser Phe Leu Tyr Asp Tyr Tyr Met Gly Pro Lys Glu Lys Arg Ile
65                  70                  75                  80

Leu Ser Ser Ser Thr Gly Gly Arg Asn Asp Gln Gly Lys Arg Tyr Tyr
                85                  90                  95

His Gly Met Glu Tyr Glu Thr Asp Leu Thr Pro Leu Glu Ser Pro Thr
            100                 105                 110

His Leu Met Lys Xaa Leu Thr Glu Asn Val Ser Gly Thr Pro Glu Tyr
        115                 120                 125

Pro Asp Leu Leu Lys Lys Asn Asn Leu Met Ser Leu Glu Gly Ala Leu
    130                 135                 140

Pro Thr Pro Gly Lys Ala Ala Pro Leu Pro Ala Gly Pro Ser Lys Leu
145                 150                 155                 160
```

```
Glu Ala Gly Ser Val Asp Ser Tyr Leu Leu Pro Xaa Thr Asp Met Tyr
                165                 170                 175

Asp Asn Gly Ser Leu Asn Ser Leu Phe Glu Ser Ile His Gly Val Pro
            180                 185                 190

Pro Thr Gln Arg Trp Gln Pro Asp Ser Thr Phe Lys Asp Asp Pro Gln
        195                 200                 205

Glu Ser Met Leu Phe Pro Asp Ile Leu Lys Thr Ser Pro Glu Pro Pro
    210                 215                 220

Cys Pro Glu Asp Tyr Pro Ser Leu Lys Ser Asp Phe Glu Tyr Thr Leu
225                 230                 235                 240

Gly Ser Pro Lys Ala Ile His Ile Lys Ser Gly Glu Ser Pro Met Ala
                245                 250                 255

Tyr Leu Asn Lys Gly Gln Phe Tyr Pro Val Thr Leu Arg Thr Pro Ala
            260                 265                 270

Gly Gly Lys Gly Leu Ala Leu Ser Ser Asn Lys Val Lys Ser Val Val
        275                 280                 285

Met Val Val Phe Asp Asn Glu Lys Val Pro Val Glu Gln Leu Arg Phe
    290                 295                 300

Trp Lys His Trp His Ser Arg Gln Pro Thr Ala Lys Gln Arg Val Ile
305                 310                 315                 320

Asp Val Ala Asp Cys Lys Glu Asn Phe Asn Thr Val Glu His Ile Glu
                325                 330                 335

Glu Val Ala Tyr Asn Ala Leu Ser Phe Val Trp Asn Val Asn Glu Glu
            340                 345                 350

Ala Lys Val Phe Ile Gly Val Asn Cys Leu Ser Thr Asp Phe Ser Ser
        355                 360                 365

Gln Lys Gly Val Lys Gly Val Pro Leu Asn Leu Gln Ile Asp Thr Tyr
    370                 375                 380

Asp Cys Gly Leu Gly Thr Glu Arg Leu Val His Arg Ala Val Cys Gln
385                 390                 395                 400

Ile Lys Ile Phe Cys Asp Lys Gly Ala Glu Arg Lys Met Arg Asp Asp
                405                 410                 415

Glu Arg Lys Gln Phe Arg Arg Lys Val Lys Cys Pro Asp Ser Ser Asn
            420                 425                 430

Ser Gly Val Lys Gly Cys Leu Leu Ser Gly Phe Arg Gly Asn Glu Thr
        435                 440                 445

Thr Tyr Leu Arg Pro Glu Thr Asp Leu Glu Thr Pro Pro Val Leu Phe
    450                 455                 460

Ile Pro Asn Val His Phe Ser Ser Leu Gln Arg Ser Gly Gly Ala Ala
465                 470                 475                 480

Pro Ser Ala Gly Pro Ser Ser Ser Asn Arg Leu Pro Leu Lys Arg Thr
                485                 490                 495

Cys Ser Pro Phe Thr Glu Glu Phe Glu Pro Leu Pro Ser Lys Gln Ala
            500                 505                 510

Lys Glu Gly Asp Leu Gln Arg Val Leu Leu Tyr Val Arg Arg Glu Thr
        515                 520                 525

Glu Glu Val Phe Asp Ala Leu Met Leu Lys Thr Pro Asp Leu Lys Gly
    530                 535                 540

Leu Arg Asn Ala Ile Ser Glu Lys Tyr Gly Phe Pro Glu Glu Asn Ile
545                 550                 555                 560

Tyr Lys Val Tyr Lys Lys Cys Lys Arg Gly Ile Leu Val Asn Met Asp
                565                 570                 575
```

```
Asn Asn Ile Ile Gln His Tyr Ser Asn His Val Ala Phe Leu Leu Asp
        580                 585                 590
Met Gly Glu Leu Asp Gly Lys Ile Gln Ile Ile Leu Lys Glu Leu
    595                 600                 605

<210> SEQ ID NO 9
<211> LENGTH: 3113
<212> TYPE: DNA
<213> ORGANISM: MURINE
<220> FEATURE:
<221> NAME/KEY: misc_feature
<222> LOCATION: (2634)..(2634)
<223> OTHER INFORMATION: n = any nucleotide
<220> FEATURE:
<221> NAME/KEY: misc_feature
<222> LOCATION: (2968)..(2968)
<223> OTHER INFORMATION: n = any nucleotide

<400> SEQUENCE: 9
gttcctccat gggttccttg agttcctgac atggcttccc ttgatgatga actgtgtgac      60
ctaaacagca taccaaatgt gacggagcag cccctcattt ctgctggaga aacagggta     120 caagtgctga aaacgtgcc cttcaacatc gtcctccccc atagcaacca gctgggcatt     180
gataagagag ccatctgac agctcccgat acaacagtca ctgtctccat agcgaccatg     240
cctacccact ccatcaagac agaaatccag ccgcacggct tgctgtgggg aatccctcca     300
gccgtgtacc actctgagcc caccgaacgc gtggtggttt tgaccggag cctcagcact     360 gatcagttca gctctggcac tcagcccccc aatgctcagc ggaggactcc agactccacc     420
ttctccgaga ccttcaagga gggcgttcag gaggttttct tcccctcgga actcagcctt     480
cggatgccgg gcatgaattc agaggactat gtctttgaca tgtttctgg gaacaacttt     540 gagtataccc tggaagcctc caagtcactg cggcagaagc aaggggacag cactatgaca     600
tacctgaata aggccagtt ctatcctgtc accttaaagg aaggaagcag caatgaaggg     660
attcaccacc ctatcagcaa agttcgaagt gtgatcatgg tggttttgc tgaagacaaa     720 agcagagaag accagctgag acactggaag tactggcact cccgtcagca cacggccaaa     780
cagaggtgca ttgacattgc tgactacaaa gaaagtttca cactatcag caacattgag     840 gagatagctt ataacgccat tccttcacg tgggacatca atgatgaggc aaaggtcttc     900
atctctgtga actgcttgag cacagatttc tcttctcaga agggtgtgaa gggcttgcca     960
ctcaacattc aaatcgacac atacagctat aacaaccgca gcaacaagcc ggttcaccgg    1020
gcctactgcc agataaaggt cttctgcgac aagggagctg aaaggaaat tcgggatgaa    1080 gaacgaaaac agagcaagag aaaagtgtct gacgttaaag tgcagctgct tccctcacac    1140
aaacggacag acatcacagt gttcaagccc ttcctggacc tcgacactca gcctgtcctc    1200
ttcattccgg acgtgcattt taccaacctg cagcggggca gtcatgttct ttccctcccc    1260
tctgaagaac tggaaggtga aggctctgtc ttgaaaagag ggccattcgg aaccgaagat    1320
gactttggag ttcctcctcc tgctaagctg actcggacag aagaacccaa gagagtgctg    1380
ctctatgtcc gaaaggaatc agaagaagtc ttcgacgccc tgatgctcaa gacgccgtct    1440
ttgaagggcc tgatggaggc aatttcagac aagtatgatg tcccccatga caagattggg    1500
aaaatattta gaagtgcaa aaagggatc tcgtgaaca tggacgacaa cattgtgaag    1560
cactactcca atgaggacac cttccagctg cagatagagg aagccggcgg ctcgtacaag    1620 ctcacccctga cagagattta aggggcagg ggtggggggc gctcggctcc caggcgtggg    1680
aattcagtga aagtgttcca gctgagaagc ccaggcacct accctgcaga accttaaata    1740
```

```
tcagggaagg aacctttcac gtaggaaatg gcgctgtgta taccgtgctg tgttgatgtt      1800
ttcttttgga tagaaatcca tgtgttgttt tgttgttgtt gtttgaattt ctgatgtgct      1860
tagaaagcga agcatgagaa ctttgtaccg gatctaagag accatgggac cgtttgggtt      1920
acctgctcca ctacctgtca aagtctgcct gtgtccataa gagtggtggg ctactggctg      1980
gcgagagagg ggaaggcagt agcttgtctt tgaggctttt gtgttctcgc ctgacctcag      2040
tctaactctg actgccttga ggagtgggcc cagccctcag caataaaggg ctaagccttc      2100
tccctccacc tctcctccag tgtttactaa atagggtgca ttcctggaac cttttcccgc      2160 aacttcccctt ggacatgtgg actgcctttc tgatgaagaa cttgcgtgag tgacagtgtg      2220
aagttagctc tgttaaagct gcgttgtata aagtgcaat atcttttga aggtctgcct       2280 gtaaatgtgt acatatatgt ctgatataaa tatataatat ataaatgcgg tgtctgtgta      2340
cagatagtga aggcgagcag gaagatctac cttgaaatcc ctcttagaga agaggttaag      2400
ttattattga taatgtggac caagcaggta gaacgctgtt ttcccaaaaa caagcaagtg      2460
ttccctagca tagcaaaaag ccatctcatg tggcagagcc atctgctctt gcgaatgttg      2520
tcaccgtgtg ggtttctgca ccctgagtgg agctaatgga agactggact gcagctacta      2580
tatgaggtgt gtgtgcaggt gtcagccaag ctgtgcccat gcagagactc agcngtgtca      2640
tgagccagcg attcaaacca aaatgggccg attctacaag gccatgtttc agagcttcca      2700
agcatcagct accgtgtgtt tgaactggaa ggcattcatg aatttacata actgtggcag      2760
gggaatgttt tgtgcacact taaatattta agaacaaaac gaaactttac aatgtaaytt      2820
tataatgaat cctgtaacag aaatacaatt gcgggtttct ttaggttcag ggaactagaa      2880
taggtcattt gtatgagtag gattgttagc ggtatacgta rgttaaaaag tactctaatg      2940
aagtatgtga acaaaatagc tggttttnta agatacggga tacgggtcat ataacaatat      3000
tttctatttt gttttatgaa atcagcttta cttgttttaa ttgtatcatt gaacatgtgt      3060
tttaaaccaa agggattgaa ttttatatgt ctatttcaaa aaaaaaaaaa aaa            3113
```

<210> SEQ ID NO 10
<211> LENGTH: 536
<212> TYPE: PRT
<213> ORGANISM: MURINE

<400> SEQUENCE: 10

```
Met Ala Ser Leu Asp Asp Glu Leu Cys Asp Leu Asn Ser Ile Pro Asn
1               5                   10                  15

Val Thr Glu Gln Pro Leu Ile Ser Ala Gly Glu Asn Arg Val Gln Val
            20                  25                  30

Leu Lys Asn Val Pro Phe Asn Ile Val Leu Pro His Ser Asn Gln Leu
        35                  40                  45

Gly Ile Asp Lys Arg Gly His Leu Thr Ala Pro Asp Thr Thr Val Thr
    50                  55                  60

Val Ser Ile Ala Thr Met Pro Thr His Ser Ile Lys Thr Glu Ile Gln
65                  70                  75                  80

Pro His Gly Phe Ala Val Gly Ile Pro Pro Ala Val Tyr His Ser Glu
                85                  90                  95

Pro Thr Glu Arg Val Val Val Phe Asp Arg Ser Leu Ser Thr Asp Gln
            100                 105                 110

Phe Ser Ser Gly Thr Gln Pro Pro Asn Ala Gln Arg Arg Thr Pro Asp
        115                 120                 125
```

-continued

```
Ser Thr Phe Ser Glu Thr Phe Lys Glu Gly Val Gln Glu Val Phe Phe
130                 135                 140

Pro Ser Glu Leu Ser Leu Arg Met Pro Gly Met Asn Ser Glu Asp Tyr
145                 150                 155                 160

Val Phe Asp Asn Val Ser Gly Asn Asn Phe Glu Tyr Thr Leu Glu Ala
                165                 170                 175

Ser Lys Ser Leu Arg Gln Lys Gln Gly Asp Ser Thr Met Thr Tyr Leu
                180                 185                 190

Asn Lys Gly Gln Phe Tyr Pro Val Thr Leu Lys Glu Gly Ser Ser Asn
                195                 200                 205

Glu Gly Ile His His Pro Ile Ser Lys Val Arg Ser Val Ile Met Val
210                 215                 220

Val Phe Ala Glu Asp Lys Ser Arg Glu Asp Gln Leu Arg His Trp Lys
225                 230                 235                 240

Tyr Trp His Ser Arg Gln His Thr Ala Lys Gln Arg Cys Ile Asp Ile
                245                 250                 255

Ala Asp Tyr Lys Glu Ser Phe Asn Thr Ile Ser Asn Ile Glu Glu Ile
                260                 265                 270

Ala Tyr Asn Ala Ile Ser Phe Thr Trp Asp Ile Asn Asp Glu Ala Lys
                275                 280                 285

Val Phe Ile Ser Val Asn Cys Leu Ser Thr Asp Phe Ser Ser Gln Lys
                290                 295                 300

Gly Val Lys Gly Leu Pro Leu Asn Ile Gln Ile Asp Thr Tyr Ser Tyr
305                 310                 315                 320

Asn Asn Arg Ser Asn Lys Pro Val His Arg Ala Tyr Cys Gln Ile Lys
                325                 330                 335

Val Phe Cys Asp Lys Gly Ala Glu Arg Lys Ile Arg Asp Glu Glu Arg
                340                 345                 350

Lys Gln Ser Lys Arg Lys Val Ser Asp Val Lys Val Gln Leu Leu Pro
                355                 360                 365

Ser His Lys Arg Thr Asp Ile Thr Val Phe Lys Pro Phe Leu Asp Leu
                370                 375                 380

Asp Thr Gln Pro Val Leu Phe Ile Pro Asp Val His Phe Thr Asn Leu
385                 390                 395                 400

Gln Arg Gly Ser His Val Leu Ser Leu Pro Ser Glu Glu Leu Glu Gly
                405                 410                 415

Glu Gly Ser Val Leu Lys Arg Gly Pro Phe Gly Thr Glu Asp Asp Phe
                420                 425                 430

Gly Val Pro Pro Pro Ala Lys Leu Thr Arg Thr Glu Glu Pro Lys Arg
                435                 440                 445

Val Leu Leu Tyr Val Arg Lys Glu Ser Glu Val Phe Asp Ala Leu
                450                 455                 460

Met Leu Lys Thr Pro Ser Leu Lys Gly Leu Met Glu Ala Ile Ser Asp
465                 470                 475                 480

Lys Tyr Asp Val Pro His Asp Lys Ile Gly Lys Ile Phe Lys Lys Cys
                485                 490                 495

Lys Lys Gly Ile Leu Val Asn Met Asp Asp Asn Ile Val Lys His Tyr
                500                 505                 510

Ser Asn Glu Asp Thr Phe Gln Leu Gln Ile Glu Glu Ala Gly Gly Ser
                515                 520                 525

Tyr Lys Leu Thr Leu Thr Glu Ile
                530                 535
```

<210> SEQ ID NO 11
<211> LENGTH: 3452
<212> TYPE: DNA
<213> ORGANISM: MURINE
<220> FEATURE:
<221> NAME/KEY: misc_feature
<222> LOCATION: (2973)..(2973)
<223> OTHER INFORMATION: n = any nucleotide
<220> FEATURE:
<221> NAME/KEY: misc_feature
<222> LOCATION: (3307)..(3307)
<223> OTHER INFORMATION: n = any nucleotide

<400> SEQUENCE: 11

```
cgccgctccg acccaccgc ctgccgccgc gcgccgcccg ccgccgcctc ctcccccgg       60
atcgggtgta ctgtcccaac ccgaaagtcc agttctgcgg cccggcagcg gcgagcgagc     120
gcgatgacac aggagtacga caacaaaagg cccgtgctgg tacttcagaa tgaagccctc     180
tacccacagc ggcgctccta taccagtgag gatgaagcct ggaagtcgtt cctggaaaac     240
cctctcactg cggcaaccaa agcgatgatg agcatcaacg gagacgaaga cagcgcggct     300
gcgctgggcc tgctctatga ctactacaag gtccccagag agcgccggtc atcagccgta     360
aagcccgagg gagagcaccc agagccagag cacagcaaaa gaaacagcat accaaatgtg     420
acggagcagc ccctcatttc tgctggagaa aacagggtac aagtgctgaa aaacgtgccc     480
ttcaacatcg tcctccccca tagcaaccag ctgggcattg ataagagagg ccatctgaca     540
gctcccgata caacagtcac tgtctccata gcgaccatgc ctacccactc catcaagaca     600
gaaatccagc cgcacggctt tgctgtggga atccctccag ccgtgtacca ctctgagccc     660
accgaacgcg tggtggtttt tgaccggagc ctcagcactg atcagttcag ctctggcact     720
cagccccca atgctcagcg gaggactcca gactccacct ctccgagac cttcaaggag       780
ggcgttcagg aggttttctt cccctcggaa ctcagccttc ggatgccggg catgaattca     840
gaggactatg tctttgacaa tgtttctggg aacaactttg agtatacccct ggaagcctcc   900
aagtcactgc ggcagaagca aggggacagc actatgacat acctgaataa aggccagttc   960
tatcctgtca ccttaaagga aggaagcagc aatgaaggga ttcaccaccc tatcagcaaa   1020
gttcgaagtg tgatcatggt ggttttgct gaagacaaaa gcagagaaga ccagctgaga   1080
cactggaagt actggcactc ccgtcagcac acggccaaac agaggtgcat tgacattgct   1140
gactacaaag aaagtttcaa cactatcagc aacattgagg agatagctta taacgccatt   1200
tccttcacgt gggacatcaa tgatgaggca aaggtcttca tctctgtgaa ctgcttgagc   1260
acagatttct cttctcagaa gggtgtgaag ggcttgccac tcaacattca aatcgacaca   1320
tacagctata caaccgcag caacaagccg gttcaccggg cctactgcca gataaaggtc   1380
ttctgcgaca agggagctga aggaaaatt cgggatgaag aacgaaaaca gagcaagaga   1440
aaagtgtctg acgttaaagt gcagctgctt ccctcacaca acggacaga catcacagtg     1500
ttcaagccct tcctggacct cgacactcag cctgtcctct tcattccgga cgtgcatttt   1560
accaacctgc agcggggcag tcatgttctt tccctcccct ctgaagaact ggaaggtgaa   1620
ggctctgtct tgaaaagagg gccattcgga accgaagatg actttggagt tcctcctcct   1680
gctaagctga ctcggacaga agaacccaag agagtgctgc tctatgtccg aaaggaatca   1740
gaagaagtct tcgacgccct gatgctcaag acgccgtctt tgagggcct gatggaggca   1800
atttcagaca gtatgatgt ccccccatgac aagattggga aaatatttaa gaagtgcaaa   1860
aaagggatcc tcgtgaacat ggacgacaac attgtgaagc actactccaa tgaggacacc   1920
```

-continued

```
ttccagctgc agatagagga agccggcggc tcgtacaagc tcaccctgac agagatttaa   1980
aggggcaggg gtgggggggcg ctcggctccc aggcgtggga attcagtgaa agtgttccag   2040
ctgagaagcc caggcaccta ccctgcagaa ccttaaatat cagggaagga acctttcacg   2100
taggaaatgg cgctgtgtat accgtgctgt gttgatgttt tcttttggat agaaatccat   2160
gtgttgtttt gttgttgttg tttgaatttc tgatgtgctt agaaagcgaa gcatgagaac   2220
tttgtaccgg atctaagaga ccatgggacc gtttgggtta cctgctccac tacctgtcaa   2280
agtctgcctg tgtccataag agtggtgggc tactggctgg cgagagaggg gaaggcagta   2340
gcttgtcttt gaggcttttg tgttctcgcc tgacctcagt ctaactctga ctgccttgag   2400
gagtgggccc agccctcagc aataaagggc taagccttct ccctccacct ctcctccagt   2460
gtttactaaa tagggtgcat tcctggaacc ttttcccgca acttcccttg acatgtggaa   2520
ctgcctttct gatgaagaac ttgcgtgagt gacagtgtga agttagctct gttaaagctg   2580
cgttgtatat aagtgcaata tcttttttgaa ggtctgcctg taaatgtgta catatatgtc   2640
tgatataaat ataatatata taaatgcggt gtctgtgtac agatagtgaa ggcgagcagg   2700
aagatctacc ttgaaatccc tcttagaaga gaggttaagt tattattgat aatgtggacc   2760
aagcaggtag aacgctgttt tcccaaaaac aagcaagtgt tccctagcat agcaaaaagc   2820
catctcatgt ggcagagcca tctgctcttg cgaatgttgt caccgtgtgg gtttctgcac   2880
cctgagtgga gctaatggaa gactggactg cagctactat atgaggtgtg tgtgcaggtg   2940
tcagccaagc tgtgcccatg cagagactca gcngtgtcat gagccagcga ttcaaaccaa   3000
aatgggccga ttctacaagg ccatgtttca gagcttccaa gcatcagcta ccgtgtgttt   3060
gaactggaag gcattcatga atttacataa ctgtggcagg ggaatgtttt gtgcacactt   3120
aaatatttaa gaacaaaacg aaactttaca atgtaaytt ataatgaatc ctgtaacaga   3180
aatacaattg cgggtttctt taggttcagg gaactagaat aggtcatttg tatgagtagg   3240
attgttagcg gtatacgtar gttaaaaagt actctaatga agtatgtgaa caaaatagct   3300
ggttttntaa gatacgggat acgggtcata taacaatatt ttctattttg ttttatgaaa   3360
tcagctttac ttgttttaat tgtatcattg aacatgtgtt ttaaaccaaa gggattgaat   3420
tttatatgtc tatttcaaaa aaaaaaaaaa aa   3452
```

<210> SEQ ID NO 12
<211> LENGTH: 618
<212> TYPE: PRT
<213> ORGANISM: MURINE

<400> SEQUENCE: 12

```
Met Thr Gln Glu Tyr Asp Asn Lys Arg Pro Val Leu Val Leu Gln Asn
1               5                   10                  15

Glu Ala Leu Tyr Pro Gln Arg Arg Ser Tyr Thr Ser Glu Asp Glu Ala
            20                  25                  30

Trp Lys Ser Phe Leu Glu Asn Pro Leu Thr Ala Ala Thr Lys Ala Met
        35                  40                  45

Met Ser Ile Asn Gly Asp Glu Asp Ser Ala Ala Ala Leu Gly Leu Leu
    50                  55                  60

Tyr Asp Tyr Tyr Lys Val Pro Arg Glu Arg Arg Ser Ser Ala Val Lys
65                  70                  75                  80

Pro Glu Gly Glu His Pro Glu Pro Glu His Ser Lys Arg Asn Ser Ile
                85                  90                  95

Pro Asn Val Thr Glu Gln Pro Leu Ile Ser Ala Gly Glu Asn Arg Val
```

-continued

```
                100                 105                 110
Gln Val Leu Lys Asn Val Pro Phe Asn Ile Val Leu Pro His Ser Asn
            115                 120                 125
Gln Leu Gly Ile Asp Lys Arg Gly His Leu Thr Ala Pro Asp Thr Thr
        130                 135                 140
Val Thr Val Ser Ile Ala Thr Met Pro Thr His Ser Ile Lys Thr Glu
145                 150                 155                 160
Ile Gln Pro His Gly Phe Ala Val Gly Ile Pro Pro Ala Val Tyr His
                165                 170                 175
Ser Glu Pro Thr Glu Arg Val Val Phe Asp Arg Ser Leu Ser Thr
            180                 185                 190
Asp Gln Phe Ser Ser Gly Thr Gln Pro Pro Asn Ala Gln Arg Arg Thr
        195                 200                 205
Pro Asp Ser Thr Phe Ser Glu Thr Phe Lys Glu Gly Val Gln Glu Val
210                 215                 220
Phe Phe Pro Ser Glu Leu Ser Leu Arg Met Pro Gly Met Asn Ser Glu
225                 230                 235                 240
Asp Tyr Val Phe Asp Asn Val Ser Gly Asn Asn Phe Glu Tyr Thr Leu
                245                 250                 255
Glu Ala Ser Lys Ser Leu Arg Gln Lys Gln Gly Asp Ser Thr Met Thr
            260                 265                 270
Tyr Leu Asn Lys Gly Gln Phe Tyr Pro Val Thr Leu Lys Glu Gly Ser
        275                 280                 285
Ser Asn Glu Gly Ile His His Pro Ile Ser Lys Val Arg Ser Val Ile
290                 295                 300
Met Val Val Phe Ala Glu Asp Lys Ser Arg Glu Asp Gln Leu Arg His
305                 310                 315                 320
Trp Lys Tyr Trp His Ser Arg Gln His Thr Ala Lys Gln Arg Cys Ile
                325                 330                 335
Asp Ile Ala Asp Tyr Lys Glu Ser Phe Asn Thr Ile Ser Asn Ile Glu
            340                 345                 350
Glu Ile Ala Tyr Asn Ala Ile Ser Phe Thr Trp Asp Ile Asn Asp Glu
        355                 360                 365
Ala Lys Val Phe Ile Ser Val Asn Cys Leu Ser Thr Asp Phe Ser Ser
370                 375                 380
Gln Lys Gly Val Lys Gly Leu Pro Leu Asn Ile Gln Ile Asp Thr Tyr
385                 390                 395                 400
Ser Tyr Asn Asn Arg Ser Asn Lys Pro Val His Arg Ala Tyr Cys Gln
                405                 410                 415
Ile Lys Val Phe Cys Asp Lys Gly Ala Glu Arg Lys Ile Arg Asp Glu
            420                 425                 430
Glu Arg Lys Gln Ser Lys Arg Lys Val Ser Asp Val Lys Val Gln Leu
        435                 440                 445
Leu Pro Ser His Lys Arg Thr Asp Ile Thr Val Phe Lys Pro Phe Leu
450                 455                 460
Asp Leu Asp Thr Gln Pro Val Leu Phe Ile Pro Asp Val His Phe Thr
465                 470                 475                 480
Asn Leu Gln Arg Gly Ser His Val Leu Ser Leu Pro Ser Glu Leu
                485                 490                 495
Glu Gly Glu Gly Ser Val Leu Lys Arg Gly Pro Phe Gly Thr Glu Asp
            500                 505                 510
Asp Phe Gly Val Pro Pro Ala Lys Leu Thr Arg Thr Glu Glu Pro
        515                 520                 525
```

```
Lys Arg Val Leu Leu Tyr Val Arg Lys Glu Ser Glu Glu Val Phe Asp
    530                 535                 540
Ala Leu Met Leu Lys Thr Pro Ser Leu Lys Gly Leu Met Glu Ala Ile
545                 550                 555                 560
Ser Asp Lys Tyr Asp Val Pro His Asp Lys Ile Gly Lys Ile Phe Lys
                565                 570                 575
Lys Cys Lys Lys Gly Ile Leu Val Asn Met Asp Asp Asn Ile Val Lys
            580                 585                 590
His Tyr Ser Asn Glu Asp Thr Phe Gln Leu Gln Ile Glu Glu Ala Gly
        595                 600                 605
Gly Ser Tyr Lys Leu Thr Leu Thr Glu Ile
    610                 615

<210> SEQ ID NO 13
<211> LENGTH: 2195
<212> TYPE: DNA
<213> ORGANISM: murine

<400> SEQUENCE: 13
cgcccgggca ggtcagactt gaaagtccag tttcaccaga ggctgaggct ccaggaaaag      60
gggagcgagt tcattggatc aaacatgtca caagagtcgg acaataataa aagactagtg     120
gccttagtgc ccatgcccag tgaccctccc ttcaacaccc gaagagccta cacaagtgag     180
gatgaggcct ggaagtcata tctggagaac cccctgactg cggccaccaa ggcgatgatg     240
agcatcaacg gggacgagga cagtgctgcc gccctgggcc tgctctatga ctactacaag     300
gttcctcgag acaagagact tctgtctgtg agcaaagcaa gtgacagcca agaagaccag     360
gataaaagaa actgccttgg caccagtgaa gcccagatca atttgagcgg aggcgagaac     420
agagtgcagg ttctgaagac tgtcccggtg aacctctgtc taagtcaaga ccacatggag     480
aattcgaagc gcgagcagta cagtgtatcc atcaccgaga gctctgccgt catccccgtg     540
tcaggcatca ccgtggtgaa agccgaggat ttcacaccgg tgttcatggc gccccggtg      600
cactatcccc gcgcggacag tgaggagcag cgcgtggtta tctttgaaca gactcagtac     660
gacctgccct ccatagccag ccacagctcc tatctcaagg acgaccagcg cagcacgccg     720
gacagcacct cagcgagag ctttaaggac ggcgcctcgg agaaatttcg gagtacttct      780
gttggtgctg acgagtatac atatgaccag acgggaagtg gtacatttca gtacaccctg     840
gaagccacca atctctccg tcagaaacag ggggagggcc ccatgaccta cctcaacaaa      900
ggacaattct atgccataac actcagtgag actggagaca caaatgcttc cgacacccc      960
atcagcaaag tcaggagtgt ggtgatggtg gtctttagtg aagacaaaaa ccgagatgag    1020
cagctgaaat actggaagta ctggcactcc cggcagcaca ctgccaagca gagggtcctt    1080
gacattgctg attacaagga gagcttcaac accatcggga acattgaaga gatcgcatac    1140
aatgctgttt ccttcacctg ggatgtgaac gaggaggcaa agattttat caccgtgaat     1200
tgcctgagta cagatttctc ctcccaaaag ggtgtaaaag acttcccct gatgattcag     1260
atcgacacgt acagctacaa caaccgcagc aataaaccca tccacagagc atactgccag    1320
atcaaggtct tctgtgacaa gggagcagaa agaaaaatcc gggatgaaga gagaaagcag    1380
aacaggaaga aagggaaggg ccaggcctct caagcccagt gcaacaactc ctctgatggg    1440
aagatggccg cctaccgtt acagaagaag agtgacatca cgtacttcaa aaccatgccc    1500
gacctgcact cacagcctgt gctcttcata ccagatgttc actttgcaaa cctacagagg    1560
```

-continued

```
accggacagg tttattacaa cacagacgat gagcgagaag gcagcagcgt ccttgttaag      1620
cggatgttca ggcccatgga agaggagttt ggtccaacac cgtctaagca gatcaaagaa      1680
gaaaacgtaa aacgagtgct tttatatgtg aggaaggaga acgatgacgt cttcgatgct      1740
ctgatgctga aatcacccac ggtgaagggt ctgatggaag cgctgtctga aagtatgggg      1800
ctgccagtgg agaaaatcac aaagctttat aagaagagca aaagggcat cctggtcaac       1860 atggatgaca acatcattga gcactattca aatgaggaca ccttcatcct caacatggag      1920
agcatggtgg aaggcttcaa gatcacgctg atggagatct gagccctggg tgtcccctcg      1980
ataggagctt ttggtatact ccttcctggg agagatggga tctctgccgc cccaggacct      2040
ggagacccac ccatctcact cacctctcaa gactgttaca agactgctgg gaagggggc       2100 agggcccaag gcccagtaat ggacttcctt caactcttcc acttgctccc tatggagctg      2160
aagcctgagc ccctcagcaa atttcttctc gtgcc                                 2195
```

<210> SEQ ID NO 14
<211> LENGTH: 625
<212> TYPE: PRT
<213> ORGANISM: murine

<400> SEQUENCE: 14

```
Met Ser Gln Glu Ser Asp Asn Asn Lys Arg Leu Val Ala Leu Val Pro
 1               5                  10                  15

Met Pro Ser Asp Pro Pro Phe Asn Thr Arg Arg Ala Tyr Thr Ser Glu
                20                  25                  30

Asp Glu Ala Trp Lys Ser Tyr Leu Glu Asn Pro Leu Thr Ala Ala Thr
             35                  40                  45

Lys Ala Met Met Ser Ile Asn Gly Asp Glu Asp Ser Ala Ala Ala Leu
         50                  55                  60

Gly Leu Leu Tyr Asp Tyr Tyr Lys Val Pro Arg Asp Lys Arg Leu Leu
 65                  70                  75                  80

Ser Val Ser Lys Ala Ser Asp Ser Gln Glu Asp Gln Asp Lys Arg Asn
                 85                  90                  95

Cys Leu Gly Thr Ser Glu Ala Gln Ile Asn Leu Ser Gly Gly Glu Asn
                100                 105                 110

Arg Val Gln Val Leu Lys Thr Val Pro Val Asn Leu Cys Leu Ser Gln
            115                 120                 125

Asp His Met Glu Asn Ser Lys Arg Glu Gln Tyr Ser Val Ser Ile Thr
        130                 135                 140

Glu Ser Ser Ala Val Ile Pro Val Ser Gly Ile Thr Val Val Lys Ala
145                 150                 155                 160

Glu Asp Phe Thr Pro Val Phe Met Ala Pro Val His Tyr Pro Arg
                165                 170                 175

Ala Asp Ser Glu Glu Gln Arg Val Val Ile Phe Glu Gln Thr Gln Tyr
            180                 185                 190

Asp Leu Pro Ser Ile Ala Ser His Ser Ser Tyr Leu Lys Asp Asp Gln
        195                 200                 205

Arg Ser Thr Pro Asp Ser Thr Tyr Ser Glu Ser Phe Lys Asp Gly Ala
    210                 215                 220

Ser Glu Lys Phe Arg Ser Thr Ser Val Gly Ala Asp Glu Tyr Thr Tyr
225                 230                 235                 240

Asp Gln Thr Gly Ser Gly Thr Phe Gln Tyr Thr Leu Glu Ala Thr Lys
                245                 250                 255

Ser Leu Arg Gln Lys Gln Gly Glu Gly Pro Met Thr Tyr Leu Asn Lys
```

```
                260                 265                 270
Gly Gln Phe Tyr Ala Ile Thr Leu Ser Glu Thr Gly Asp Asn Lys Cys
        275                 280                 285

Phe Arg His Pro Ile Ser Lys Val Arg Ser Val Val Met Val Val Phe
    290                 295                 300

Ser Glu Asp Lys Asn Arg Asp Glu Gln Leu Lys Tyr Trp Lys Tyr Trp
305                 310                 315                 320

His Ser Arg Gln His Thr Ala Lys Gln Arg Val Leu Asp Ile Ala Asp
                325                 330                 335

Tyr Lys Glu Ser Phe Asn Thr Ile Gly Asn Ile Glu Glu Ile Ala Tyr
            340                 345                 350

Asn Ala Val Ser Phe Thr Trp Asp Val Asn Glu Glu Ala Lys Ile Phe
        355                 360                 365

Ile Thr Val Asn Cys Leu Ser Thr Asp Phe Ser Ser Gln Lys Gly Val
    370                 375                 380

Lys Gly Leu Pro Leu Met Ile Gln Ile Asp Thr Tyr Ser Tyr Asn Asn
385                 390                 395                 400

Arg Ser Asn Lys Pro Ile His Arg Ala Tyr Cys Gln Ile Lys Val Phe
                405                 410                 415

Cys Asp Lys Gly Ala Glu Arg Lys Ile Arg Asp Glu Arg Lys Gln
            420                 425                 430

Asn Arg Lys Lys Gly Lys Gly Gln Ala Ser Gln Ala Gln Cys Asn Asn
        435                 440                 445

Ser Ser Asp Gly Lys Met Ala Ala Ile Pro Leu Gln Lys Lys Ser Asp
    450                 455                 460

Ile Thr Tyr Phe Lys Thr Met Pro Asp Leu His Ser Gln Pro Val Leu
465                 470                 475                 480

Phe Ile Pro Asp Val His Phe Ala Asn Leu Gln Arg Thr Gly Gln Val
                485                 490                 495

Tyr Tyr Asn Thr Asp Asp Glu Arg Glu Gly Ser Ser Val Leu Val Lys
            500                 505                 510

Arg Met Phe Arg Pro Met Glu Glu Phe Gly Pro Thr Pro Ser Lys
        515                 520                 525

Gln Ile Lys Glu Glu Asn Val Lys Arg Val Leu Leu Tyr Val Arg Lys
    530                 535                 540

Glu Asn Asp Asp Val Phe Asp Ala Leu Met Leu Lys Ser Pro Thr Val
545                 550                 555                 560

Lys Gly Leu Met Glu Ala Leu Ser Glu Lys Tyr Gly Leu Pro Val Glu
                565                 570                 575

Lys Ile Thr Lys Leu Tyr Lys Lys Ser Lys Lys Gly Ile Leu Val Asn
            580                 585                 590

Met Asp Asp Asn Ile Ile Glu His Tyr Ser Asn Glu Asp Thr Phe Ile
        595                 600                 605

Leu Asn Met Glu Ser Met Val Glu Gly Phe Lys Ile Thr Leu Met Glu
    610                 615                 620

Ile
625

<210> SEQ ID NO 15
<211> LENGTH: 2831
<212> TYPE: DNA
<213> ORGANISM: murine
<220> FEATURE:
<221> NAME/KEY: CDS
<222> LOCATION: (200)..(2008)
```

```
<220> FEATURE:
<221> NAME/KEY: misc_feature
<222> LOCATION: (2806)..(2806)
<223> OTHER INFORMATION: n = any nucleotide

<400> SEQUENCE: 15
acctgtgctt ccagccaatc agcgccaccg cagccgggga ccgctgtcag caaaatctca     60
acatccagag cgcaacgtag agcaaacgct tccccgggca ggaagggaat gtctgtgtca    120
gaggagaatt aagagacgag tggtcagcag cgcctgcgag ccaaccagag acggatcgct    180
ggaacctcgg agaaggaag atg tcg aat gaa ctt gat ttc agg tct gtg cgg    232
                     Met Ser Asn Glu Leu Asp Phe Arg Ser Val Arg
                      1               5                  10 ttg ctg aag aat gac cct gtg agc ttc cag aag ttt ccc tac agt aat    280
Leu Leu Lys Asn Asp Pro Val Ser Phe Gln Lys Phe Pro Tyr Ser Asn
             15                  20                  25 gag gac gag gcc tgg aag aca tac ctg gag aac cct ttg acg gct gcc    328
Glu Asp Glu Ala Trp Lys Thr Tyr Leu Glu Asn Pro Leu Thr Ala Ala
 30                  35                  40 acc aaa gcc atg atg aga gtc aac ggg gac gag gag agt gtg gct gct    376
Thr Lys Ala Met Met Arg Val Asn Gly Asp Glu Glu Ser Val Ala Ala
 45                  50                  55 ctg agc ttc ctc tac gac tac tat atg ggt ccc aag gag aag cgg ata    424
Leu Ser Phe Leu Tyr Asp Tyr Tyr Met Gly Pro Lys Glu Lys Arg Ile
 60                  65                  70                  75 ctg tcc tcc agc act ggt ggc cgg aat gac caa gga aag aag ttc tac    472
Leu Ser Ser Ser Thr Gly Gly Arg Asn Asp Gln Gly Lys Lys Phe Tyr
             80                  85                  90 cac agc atg gac tat gag ccg gat ctt gcc ccc ctc gag agc ccc aca    520
His Ser Met Asp Tyr Glu Pro Asp Leu Ala Pro Leu Glu Ser Pro Thr
             95                 100                 105 cac ctc atg aaa ttt ttg aca gag aac gtg tct gga agt cca gac tac    568
His Leu Met Lys Phe Leu Thr Glu Asn Val Ser Gly Ser Pro Asp Tyr
            110                 115                 120 aca gac cag ctc aag aaa aac aat ctg cta ggc ttg gag ggg gtt cta    616
Thr Asp Gln Leu Lys Lys Asn Asn Leu Leu Gly Leu Glu Gly Val Leu
            125                 130                 135 ccc acc ccc ggc aag acc aat acc gtc ccc cca ggt ccg agt aaa ctg    664
Pro Thr Pro Gly Lys Thr Asn Thr Val Pro Pro Gly Pro Ser Lys Leu
140                 145                 150                 155 gaa gcc agc tcc atg gac agc tac ctc ttg ccc gcc agt gac ata tat    712
Glu Ala Ser Ser Met Asp Ser Tyr Leu Leu Pro Ala Ser Asp Ile Tyr
                160                 165                 170 gac aat ggc tcc ctc aac tca tta ttt gag agc att cat ggg gtt cca    760
Asp Asn Gly Ser Leu Asn Ser Leu Phe Glu Ser Ile His Gly Val Pro
            175                 180                 185 ccc aca cag cgc tgg cag cca gac agc acc ttc aaa gat gac cca cag    808
Pro Thr Gln Arg Trp Gln Pro Asp Ser Thr Phe Lys Asp Asp Pro Gln
            190                 195                 200 gag tct ctg ctc ttc cct gat att ctg aag aca tcc ccg gac ccc cca    856
Glu Ser Leu Leu Phe Pro Asp Ile Leu Lys Thr Ser Pro Asp Pro Pro
205                 210                 215 tgc cca gag gat tat cca ggc ctc aag agt gac ttt gaa tac acc ctg    904
Cys Pro Glu Asp Tyr Pro Gly Leu Lys Ser Asp Phe Glu Tyr Thr Leu
220                 225                 230                 235 ggc tcc ccc aaa gcc att cac atc aaa gca ggg gag tca ccc atg gcc    952
Gly Ser Pro Lys Ala Ile His Ile Lys Ala Gly Glu Ser Pro Met Ala
            240                 245                 250 tac ctc aac aag ggt cag ttc tac ccc gtc acc cta cgc acc cca gca   1000
Tyr Leu Asn Lys Gly Gln Phe Tyr Pro Val Thr Leu Arg Thr Pro Ala
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 255 |     |     |     | 260 |     |     |     | 265 |     |     |     |     |     |      |
| gga | ggg | aaa | ggc | ctc | gct | ctg | tcc | tcc | agc | aaa | gtc | aag | agc | gtg | gtg | 1048 |
| Gly | Gly | Lys | Gly | Leu | Ala | Leu | Ser | Ser | Ser | Lys | Val | Lys | Ser | Val | Val |      |
|     |     | 270 |     |     |     | 275 |     |     |     | 280 |     |     |     |     |     |      |
| atg | gtc | gtg | ttc | gat | aat | gac | aag | gtc | ccc | gtg | gag | cag | ctg | cgt | ttc | 1096 |
| Met | Val | Val | Phe | Asp | Asn | Asp | Lys | Val | Pro | Val | Glu | Gln | Leu | Arg | Phe |      |
|     | 285 |     |     |     |     | 290 |     |     |     |     | 295 |     |     |     |     |      |
| tgg | agg | cac | tgg | cat | tcc | cgg | cag | ccc | acc | gcc | aag | cag | cgc | gtc | atc | 1144 |
| Trp | Arg | His | Trp | His | Ser | Arg | Gln | Pro | Thr | Ala | Lys | Gln | Arg | Val | Ile |      |
| 300 |     |     |     |     | 305 |     |     |     |     | 310 |     |     |     |     | 315 |      |
| gac | gta | gct | gac | tgt | aag | gaa | aac | ttc | aac | acg | gtc | cag | cac | att | gaa | 1192 |
| Asp | Val | Ala | Asp | Cys | Lys | Glu | Asn | Phe | Asn | Thr | Val | Gln | His | Ile | Glu |      |
|     |     |     |     | 320 |     |     |     |     | 325 |     |     |     |     | 330 |     |      |
| gag | gtg | gcc | tat | aac | gcg | ctg | tcc | ttt | gtg | tgg | aat | gtc | aac | gag | gaa | 1240 |
| Glu | Val | Ala | Tyr | Asn | Ala | Leu | Ser | Phe | Val | Trp | Asn | Val | Asn | Glu | Glu |      |
|     |     |     | 335 |     |     |     |     | 340 |     |     |     |     | 345 |     |     |      |
| gcc | aag | gtg | ttt | atc | ggt | gtc | aac | tgt | ctg | agc | aca | gac | ttc | tcc | tcg | 1288 |
| Ala | Lys | Val | Phe | Ile | Gly | Val | Asn | Cys | Leu | Ser | Thr | Asp | Phe | Ser | Ser |      |
|     |     | 350 |     |     |     |     | 355 |     |     |     |     | 360 |     |     |     |      |
| cag | aag | gga | gtg | aag | ggt | gtc | ccc | ctg | aac | ttg | caa | att | gac | acc | tat | 1336 |
| Gln | Lys | Gly | Val | Lys | Gly | Val | Pro | Leu | Asn | Leu | Gln | Ile | Asp | Thr | Tyr |      |
|     | 365 |     |     |     |     | 370 |     |     |     |     | 375 |     |     |     |     |      |
| gac | tgt | gga | gca | ggc | act | gag | cgc | ctg | gta | cac | cgt | gct | gtc | tgc | cag | 1384 |
| Asp | Cys | Gly | Ala | Gly | Thr | Glu | Arg | Leu | Val | His | Arg | Ala | Val | Cys | Gln |      |
| 380 |     |     |     |     | 385 |     |     |     |     | 390 |     |     |     |     | 395 |      |
| atc | aag | atc | ttc | tgt | gat | aag | gga | gct | gag | agg | aag | atg | cgc | gat | gat | 1432 |
| Ile | Lys | Ile | Phe | Cys | Asp | Lys | Gly | Ala | Glu | Arg | Lys | Met | Arg | Asp | Asp |      |
|     |     |     |     | 400 |     |     |     |     | 405 |     |     |     |     | 410 |     |      |
| gaa | cgg | aag | cag | ttt | cga | agg | aag | gtc | aag | tgc | cca | gac | tcc | agt | aac | 1480 |
| Glu | Arg | Lys | Gln | Phe | Arg | Arg | Lys | Val | Lys | Cys | Pro | Asp | Ser | Ser | Asn |      |
|     |     |     | 415 |     |     |     |     | 420 |     |     |     |     | 425 |     |     |      |
| aat | gca | gga | atc | aag | ggc | tgc | ctg | ctg | tca | ggc | ttc | agg | ggc | aat | gag | 1528 |
| Asn | Ala | Gly | Ile | Lys | Gly | Cys | Leu | Leu | Ser | Gly | Phe | Arg | Gly | Asn | Glu |      |
|     |     | 430 |     |     |     |     | 435 |     |     |     |     | 440 |     |     |     |      |
| acc | aca | tac | ttg | cgg | cca | gaa | act | gac | ctg | gag | acc | cag | cct | gtg | ttg | 1576 |
| Thr | Thr | Tyr | Leu | Arg | Pro | Glu | Thr | Asp | Leu | Glu | Thr | Gln | Pro | Val | Leu |      |
|     | 445 |     |     |     |     | 450 |     |     |     |     | 455 |     |     |     |     |      |
| ttt | atc | ccc | aat | ctg | cat | ttt | tcc | agc | cta | cag | cgc | cca | gga | ggg | gtt | 1624 |
| Phe | Ile | Pro | Asn | Leu | His | Phe | Ser | Ser | Leu | Gln | Arg | Pro | Gly | Gly | Val |      |
| 460 |     |     |     |     | 465 |     |     |     |     | 470 |     |     |     |     | 475 |      |
| gtc | ccc | tca | gca | gga | cac | agc | agc | tct | gac | agg | ctg | cct | ctg | aag | cga | 1672 |
| Val | Pro | Ser | Ala | Gly | His | Ser | Ser | Ser | Asp | Arg | Leu | Pro | Leu | Lys | Arg |      |
|     |     |     |     | 480 |     |     |     |     | 485 |     |     |     |     | 490 |     |      |
| acc | tgc | tca | ccc | ttt | gct | gag | gag | ttt | gag | cct | ctt | cct | tct | aaa | caa | 1720 |
| Thr | Cys | Ser | Pro | Phe | Ala | Glu | Glu | Phe | Glu | Pro | Leu | Pro | Ser | Lys | Gln |      |
|     |     |     | 495 |     |     |     |     | 500 |     |     |     |     | 505 |     |     |      |
| gcc | aag | gaa | gat | gac | ctt | cag | aga | gtt | ctg | ttg | tat | gtg | agg | agg | gag | 1768 |
| Ala | Lys | Glu | Asp | Asp | Leu | Gln | Arg | Val | Leu | Leu | Tyr | Val | Arg | Arg | Glu |      |
|     | 510 |     |     |     |     | 515 |     |     |     |     | 520 |     |     |     |     |      |
| aca | gag | gag | gtg | ttt | gac | gcg | ctc | atg | ttg | aag | acc | ccg | gac | ctg | aag | 1816 |
| Thr | Glu | Glu | Val | Phe | Asp | Ala | Leu | Met | Leu | Lys | Thr | Pro | Asp | Leu | Lys |      |
| 525 |     |     |     |     | 530 |     |     |     |     | 535 |     |     |     |     |     |      |
| ggc | ctg | agg | aat | gcg | atc | tct | gag | aag | tac | ggc | ctc | ccc | gag | gag | aat | 1864 |
| Gly | Leu | Arg | Asn | Ala | Ile | Ser | Glu | Lys | Tyr | Gly | Leu | Pro | Glu | Glu | Asn |      |
| 540 |     |     |     |     | 545 |     |     |     |     | 550 |     |     |     |     | 555 |      |
| att | tgc | aaa | gtc | tac | aag | aaa | tgc | aag | cga | ggc | atc | ctg | gtt | aac | atg | 1912 |
| Ile | Cys | Lys | Val | Tyr | Lys | Lys | Cys | Lys | Arg | Gly | Ile | Leu | Val | Asn | Met |      |
|     |     |     |     | 560 |     |     |     |     | 565 |     |     |     |     | 570 |     |      |
| gac | aac | aac | atc | atc | caa | cac | tac | agc | aac | cac | gtg | gcc | ttc | ctg | ctg | 1960 |

```
                    Asp Asn Asn Ile Ile Gln His Tyr Ser Asn His Val Ala Phe Leu Leu
                                575                 580                 585 gac atg ggt gag ctg gac ggc aag atc cag atc atc ctg aag gag cta        2008
Asp Met Gly Glu Leu Asp Gly Lys Ile Gln Ile Ile Leu Lys Glu Leu
            590                 595                 600 tgagggcccg gcctcaagcg tcccacaccc ggggcccggc tcaagccacg tacaacctct     2068
tctgtgtcag ctgttacttg aaatgccttt ctttgggaaa gaggtctcgc aagcaaccaa     2128
ctcggtgatg tccaagccag ggagagacca agaaggttcc aggatctaaa tgtcccaccc     2188
aggctcgaac tcactccaga gcttcctgaa agcacccagc ccaccggaga gtctgagcaa     2248
cacagaccca actgcctgct ttctcttcta agtcccgctg cagaggccct tacaggggac     2308 ggggtcaca ccaccttctc tgcagggcta cacccgctgt ctcgatcggt tctgacgttc      2368
actgtttcct ttctaccaac ttcagaccag agagttctca cactttggcc aaataacttg     2428
aaaactcgtg actttcacag cagatgcctt tgtgaggccc ttggagagga aactttctta     2488
ttgacttcct cggcacaaga tgtaagtcac catcatcgag ctgacaggaa caaatacccct    2548 tgccacctac tgttgtacac atttcttatt tacagttttc attatgtgat tatatatata    2608
tatatgtaag tatatattat gtacatatat gcaacatttt gtatgtccat gttacatttt    2668
tatcatttca aaatatgta tttcatattt cttgaactat tttttagct gttattcgat      2728 tatgcatttt gtatatcata gggtttagta ataaaagcct acccatgcac acttaaaaaa    2788
aaaaaaaaaa aaatatcnag cttatcgata ccgtcgacct cga                       2831

<210> SEQ ID NO 16
<211> LENGTH: 603
<212> TYPE: PRT
<213> ORGANISM: murine

<400> SEQUENCE: 16

Met Ser Asn Glu Leu Asp Phe Arg Ser Val Arg Leu Leu Lys Asn Asp
1               5                   10                  15

Pro Val Ser Phe Gln Lys Phe Pro Tyr Ser Asn Glu Asp Glu Ala Trp
            20                  25                  30

Lys Thr Tyr Leu Glu Asn Pro Leu Thr Ala Ala Thr Lys Ala Met Met
        35                  40                  45

Arg Val Asn Gly Asp Glu Glu Ser Val Ala Ala Leu Ser Phe Leu Tyr
    50                  55                  60

Asp Tyr Tyr Met Gly Pro Lys Glu Lys Arg Ile Leu Ser Ser Ser Thr
65                  70                  75                  80

Gly Gly Arg Asn Asp Gln Gly Lys Lys Phe Tyr His Ser Met Asp Tyr
                85                  90                  95

Glu Pro Asp Leu Ala Pro Leu Glu Ser Pro Thr His Leu Met Lys Phe
            100                 105                 110

Leu Thr Glu Asn Val Ser Gly Ser Pro Asp Tyr Thr Asp Gln Leu Lys
        115                 120                 125

Lys Asn Asn Leu Leu Gly Leu Glu Gly Val Leu Pro Thr Pro Gly Lys
    130                 135                 140

Thr Asn Thr Val Pro Pro Gly Pro Ser Lys Leu Glu Ala Ser Ser Met
145                 150                 155                 160

Asp Ser Tyr Leu Leu Pro Ala Ser Asp Ile Tyr Asp Asn Gly Ser Leu
                165                 170                 175

Asn Ser Leu Phe Glu Ser Ile His Gly Val Pro Pro Thr Gln Arg Trp
            180                 185                 190
```

```
Gln Pro Asp Ser Thr Phe Lys Asp Asp Pro Gln Glu Ser Leu Leu Phe
    195                 200                 205

Pro Asp Ile Leu Lys Thr Ser Pro Asp Pro Pro Cys Pro Glu Asp Tyr
210                 215                 220

Pro Gly Leu Lys Ser Asp Phe Glu Tyr Thr Leu Gly Ser Pro Lys Ala
225                 230                 235                 240

Ile His Ile Lys Ala Gly Glu Ser Pro Met Ala Tyr Leu Asn Lys Gly
                245                 250                 255

Gln Phe Tyr Pro Val Thr Leu Arg Thr Pro Ala Gly Lys Gly Leu
            260                 265                 270

Ala Leu Ser Ser Ser Lys Val Lys Ser Val Val Met Val Val Phe Asp
            275                 280                 285

Asn Asp Lys Val Pro Val Glu Gln Leu Arg Phe Trp Arg His Trp His
290                 295                 300

Ser Arg Gln Pro Thr Ala Lys Gln Arg Val Ile Asp Val Ala Asp Cys
305                 310                 315                 320

Lys Glu Asn Phe Asn Thr Val Gln His Ile Glu Val Ala Tyr Asn
                325                 330                 335

Ala Leu Ser Phe Val Trp Asn Val Asn Glu Glu Ala Lys Val Phe Ile
            340                 345                 350

Gly Val Asn Cys Leu Ser Thr Asp Phe Ser Ser Gln Lys Gly Val Lys
            355                 360                 365

Gly Val Pro Leu Asn Leu Gln Ile Asp Thr Tyr Asp Cys Gly Ala Gly
            370                 375                 380

Thr Glu Arg Leu Val His Arg Ala Val Cys Gln Ile Lys Ile Phe Cys
385                 390                 395                 400

Asp Lys Gly Ala Glu Arg Lys Met Arg Asp Asp Glu Arg Lys Gln Phe
                405                 410                 415

Arg Arg Lys Val Lys Cys Pro Asp Ser Ser Asn Asn Ala Gly Ile Lys
            420                 425                 430

Gly Cys Leu Leu Ser Gly Phe Arg Gly Asn Glu Thr Thr Tyr Leu Arg
            435                 440                 445

Pro Glu Thr Asp Leu Glu Thr Gln Pro Val Leu Phe Ile Pro Asn Leu
    450                 455                 460

His Phe Ser Ser Leu Gln Arg Pro Gly Val Val Pro Ser Ala Gly
465                 470                 475                 480

His Ser Ser Ser Asp Arg Leu Pro Leu Lys Arg Thr Cys Ser Pro Phe
                485                 490                 495

Ala Glu Glu Phe Glu Pro Leu Pro Ser Lys Gln Ala Lys Glu Asp Asp
            500                 505                 510

Leu Gln Arg Val Leu Leu Tyr Arg Arg Glu Thr Glu Val Phe
    515                 520                 525

Asp Ala Leu Met Leu Lys Thr Pro Asp Leu Lys Gly Leu Arg Asn Ala
530                 535                 540

Ile Ser Glu Lys Tyr Gly Leu Pro Glu Glu Asn Ile Cys Lys Val Tyr
545                 550                 555                 560

Lys Lys Cys Lys Arg Gly Ile Leu Val Asn Met Asp Asn Asn Ile Ile
                565                 570                 575

Gln His Tyr Ser Asn His Val Ala Phe Leu Leu Asp Met Gly Glu Leu
            580                 585                 590

Asp Gly Lys Ile Gln Ile Ile Leu Lys Glu Leu
    595                 600
```

<210> SEQ ID NO 17
<211> LENGTH: 4840
<212> TYPE: DNA
<213> ORGANISM: drosphila

<400> SEQUENCE: 17

```
aaaaatagaa aaacaacaa caaattggct tgaaaacgca aatgccaggc gcaacgcccc      60
cgaaccgacc cgccccctca acttttgcgc cctccagtag caatagcagc aatatgagca    120
gcagcaacat caaatgttag gccaaaatgc acaaaccgcc agcaacaaag gcagcaccaa    180
gcgaacgaaa caacaacagc tccacatacc acaaagagtg gcacattaga agcggccaaa    240
agcagccagc cgagagcatt gtgtaagcca aaggcccaga gagccaggct aaaagccccc    300
agacgcacaa caacaacaac aacaactaaa acagcacaaa gagtggcgaa aggtgcaccc    360
accagcaaaa cagcaacaac ggagcaacca acaacagcag cagcagcagc agcagccaca    420
tttcagttac agctccagac tcccaggttg cagactccca agcaaacag actccagtcc     480
acgatccagc tccagttcca ccgatccgat ccactgctcc agcgtgctcg agtgccatag    540
atcctcacca agtgccaaaa tccgcatcct gatcccaaga gctcaaggca ccccggccca    600
aaattgagct gagaacgaaa cgaaggaagt tccttagtgc catagaaagc agttaatgaa    660
acaacgacta agacgaagat cgaccatcca gaaccgagg gagctaattg cgaacgaaag     720
aaaccacaaa gtgccttcca tcaatccgtt gataagtgat atttattatg tttatacttg    780
ccagcagccg aggcagcaac agcaatagca acaaccatag gggatcacgg catcgatgat    840
cagtccacga ccaagtccta gtgcaatccg gaatccagtt caaattagtt caataagccg    900
tatctaccac gtataatgtc cacatccacc gccacaacga gcgttatcac gtccaacgag    960
ctctcgctgt ccggccacgc ccacggtcac ggtcacgccc accagttgca ccagcacacc   1020
cacagccgcc taggagttgg cgttggtgtt ggcatcctta gcgacgcatc cctatcgccc   1080
atccaacaag gcagtggcgg ccacagcggc ggaggtaaca caaacagttc accactggcg   1140
cccaacggag tgccacttct cacaacaatg caccgatcac cggactcacc gcagccagaa   1200
ttggccacca tgacgaacgt caacgtgctg gatctgcaca cggataactc caagctgtac   1260
gacaaggagg ctgtatttat atacgaaacg cccaaggtgg tgatgccagc ggatggcggg   1320
ggtggcaata attccgatga aggtcatgcc atcgatgcgc ggattgcggc ccaaatgggc   1380
aaccaagccc agcaacagca gcagcagcaa cagcagacgg aacaccagcc gctggccaag   1440
atcgagttcg atgagaacca gataatccgg gtggtgggac caaatggcga gcaacagcaa   1500
atcatctcgc gggagatcat caatggggag catcatatcc tgtcgcgaaa cgaggctggt   1560
gagcacattc tcacacggat cgtcagtgat ccctccaagt tgatgcccaa tgacaatgca   1620
gtggccacgg ccatgtacaa ccaggcccaa aagatgaaca atgatcacgg gcaggcggta   1680
tatcagacat caccattgcc gctagacgcg tctgtattgc attatagtgg cggcaatgat   1740
tcgaatgtaa ttaagacgga ggccgatatc tacgaggatc acaagaaaca tgcggctgca   1800
gcagcagctg ctgccggcgg aggatccatc atatacacca catccgatcc gaacggagtg   1860
aatgtgaaac aactgcccca tttgacggta ccccaaaaac ttgatcccga cctctatcaa   1920
gccgataagc atatagattt gatctacaac gatggcagca agacggtgat ttactccact   1980
acggatcaga agagtttgga aatatactcg ggcggcgaca tcggcagcct ggtgtccgac   2040
ggccaagtgg tggtccaggc gggactgccg tatgccacca ccaccggagc cggcggccag   2100
cccgtctata tcgtggccga cggtgccttg ccagcgggag tcgaggagca tctgcagagt   2160
```

```
ggaaagctca atggccagac cacacctatc gatgtctctg gcctatcgca aaatgagatt    2220
caaggctttt tgctcggctc acacccctcg tcatcggcga cggtaagcac aaccggcgtt    2280
gtctccacga caacgatctc gcatcaccag caacagcagc agcagcagca acagcaacag    2340
cagcagcagc agcagcaaca ccagcagcag cagcaacatc ccggcgacat tgttagtgcc    2400
gctggcgtgg ggagcacggg ctccattgtc tcctctgcgg cgcaacagca gcagcagcag    2460
caactaatta gcatcaaacg agagcccgaa gacttgcgca aggatcccaa gaatggcaac    2520
attgccggtg cagcaacagc aaatggaccc ggttcggtca taacccaaaa gtcctttgat    2580
tatacggaat tgtgccagcc gggcacgctg atcgatgcca atggcagcat acccgtcagc    2640
gtgaacagca tccagcagag aacggcggtc catggcagcc agaacagtcc caccacatcg    2700
ctggtggaca ccagcaccaa tggatccacg cgatcgcggc cctggcacga ctttggacgt    2760
cagaatgatg ccgacaaaat acaaatacca aaaatcttca caaacgtggg cttccgatat    2820
cacctggaga gccccatcag ttcatcgcag aggcgcgagg acgatcgcat cacctacatc    2880
aacaagggtc aattctatgg aataacgctg gagtatgtgc acgatgcgga aaagcccatt    2940
aagaacacca ccgtcaagag tgtgatcatg ctaatgttcc gcgaggagaa gagtcccgag    3000
gatgagatca aggcctggca attctggcac agtcgtcagc attccgtgaa gcagagaatc    3060
ttggatgcag atacgaagaa ctcggttggc ctcgttggct gcatcgagga agtgtcgcac    3120
aatgccatcg ccgtctactg gaatccgctg gagagctccg ccaagatcaa cattgcggtt    3180
cagtgcttga gcacggattt cagcagtcaa aagggaggcc tgccgctgca cgtacaaatc    3240
gacacatttg aggaccccag agatacggcg gtcttccacc gcggctactg tcagataaag    3300
gtcttctgcg ataagggcgc cgaacgaaag acgcgcgatg aagagcggcg ggccgccaaa    3360
cgaaagatga cagccacggg cagaaagaag ctggacgagc tttaccatcc ggtaacggat    3420
cggtccgagt tctatggcat gcaggacttc gccaagccgc cggtgctatt ctcgcccgcc    3480
gaggacatgg agaaggtagg tcagctgggc attggcgctg ccaccggcat gacattcaac    3540
cccctgagca acggcaactc caactccaac tcgcactcgt ccttgcagag cttctacggc    3600
catgagactg actcgccgga cctgaagggg gcctcaccgt tcctgctcca cggccagaag    3660
gtggccacgc cgacgctcaa gttccacaac cattttccgc cgacatgca gaccgataag     3720 aaggatcaca tactggacca gaacatgttg accagcacac ccctgaccga ctttggtccg    3780
ccgatgaagc gcggcaggat gacgccgccg acctcggaac gcgtgatgct gtacgtgcgg    3840
caggagaacg aggaggtgta tacaccgttg cacgtggtgc cgcccaccac gatcggcctg    3900
ctaaatgcga ttgaaaacaa atacaaaatc tcaacaacga gcataaataa catttatcgc    3960
acaaacaaga aggggattac tgcgaaaatt gacgatgaca tgatatcgtt ctactgcaac    4020
gaggacatct ttctgctgga ggtgcaacag atcgaggacg acctgtacga tgtgacgctc    4080
acggagctgc ccaatcagta gcgctggcag tacgggtagc acccgctaac cgcactcaaa    4140 aaaaaagca aacaaacaca caaattacgg acacaacaag ttgtttcaat aagccatttt    4200
ccatagagcc taagtctaaa tatcgtagtt ataataatgg gatccgcaac aaatcgagtt    4260
gcaacgaatg ttaagaacgc taacacaata cgcatgtaaa atgatacttt aaaattgatt    4320
tagttatttt agcaacaatg agattatcta aaattgtttg atcaaatttt acattctcgc    4380
tatgtctata gataattcta agcccgtaag cccataagcg taatcgtaat cgtaatcgta    4440
ccgtgtattt atgctcatat ataaacaact atatatatat atatatatat atatatgtgc    4500
ggagtgcaac agtgtctgtc cagtaggaga taagtctcgt ttccgctccc ctgcttatgc    4560
```

-continued

```
tatgacctta ggtccagggc aagtatgagt taccgaatct atctattagg tgcatctaac    4620
gaaaggaatc attagctctg cacgaactct agccgtagcc tattgtaatc catttgtatg    4680
tttggcttaa gcgttttact tgttgaatat aaagtgtaaa attatttttg aaaaaaaaaa    4740
acccacacaa aacacaaatc gtttgttcta tatttctgtt tcaaaactaa ctcgttaccc    4800
acaatcccct ctgttatgta taattaggat ctctgtacac                          4840
```

<210> SEQ ID NO 18
<211> LENGTH: 1061
<212> TYPE: PRT
<213> ORGANISM: murine

<400> SEQUENCE: 18

```
Met Ser Thr Ser Thr Ala Thr Thr Ser Val Ile Thr Ser Asn Glu Leu
1               5                   10                  15

Ser Leu Ser Gly His Ala His Gly His Gly His Ala His Gln Leu His
            20                  25                  30

Gln His Thr His Ser Arg Leu Gly Val Gly Val Gly Val Gly Ile Leu
        35                  40                  45

Ser Asp Ala Ser Leu Ser Pro Ile Gln Gln Gly Ser Gly Gly His Ser
    50                  55                  60

Gly Gly Gly Asn Thr Asn Ser Ser Pro Leu Ala Pro Asn Gly Val Pro
65                  70                  75                  80

Leu Leu Thr Thr Met His Arg Ser Pro Asp Ser Pro Gln Pro Glu Leu
                85                  90                  95

Ala Thr Met Thr Asn Val Asn Val Leu Asp Leu His Thr Asp Asn Ser
            100                 105                 110

Lys Leu Tyr Asp Lys Glu Ala Val Phe Ile Tyr Glu Thr Pro Lys Val
        115                 120                 125

Val Met Pro Ala Asp Gly Gly Gly Asn Asn Ser Asp Glu Gly His
    130                 135                 140

Ala Ile Asp Ala Arg Ile Ala Ala Gln Met Gly Asn Gln Ala Gln Gln
145                 150                 155                 160

Gln Gln Gln Gln Gln Gln Thr Glu His Gln Pro Leu Ala Lys Ile
                165                 170                 175

Glu Phe Asp Glu Asn Gln Ile Ile Arg Val Val Gly Pro Asn Gly Glu
            180                 185                 190

Gln Gln Gln Ile Ile Ser Arg Glu Ile Ile Asn Gly Glu His His Ile
        195                 200                 205

Leu Ser Arg Asn Glu Ala Gly Glu His Ile Leu Thr Arg Ile Val Ser
    210                 215                 220

Asp Pro Ser Lys Leu Met Pro Asn Asp Asn Ala Val Ala Thr Ala Met
225                 230                 235                 240

Tyr Asn Gln Ala Gln Lys Met Asn Asn Asp His Gly Gln Ala Val Tyr
                245                 250                 255

Gln Thr Ser Pro Leu Pro Leu Asp Ala Ser Val Leu His Tyr Ser Gly
            260                 265                 270

Gly Asn Asp Ser Asn Val Ile Lys Thr Glu Ala Asp Ile Tyr Glu Asp
        275                 280                 285

His Lys Lys His Ala Ala Ala Ala Ala Ala Gly Gly Gly Ser
    290                 295                 300

Ile Ile Tyr Thr Thr Ser Asp Pro Asn Gly Val Asn Val Lys Gln Leu
305                 310                 315                 320
```

-continued

```
Pro His Leu Thr Val Pro Gln Lys Leu Asp Pro Asp Leu Tyr Gln Ala
            325                 330                 335

Asp Lys His Ile Asp Leu Ile Tyr Asn Asp Gly Ser Lys Thr Val Ile
            340                 345                 350

Tyr Ser Thr Thr Asp Gln Lys Ser Leu Glu Ile Tyr Ser Gly Gly Asp
            355                 360                 365

Ile Gly Ser Leu Val Ser Asp Gly Gln Val Val Gln Ala Gly Leu
    370                 375                 380

Pro Tyr Ala Thr Thr Thr Gly Ala Gly Gly Gln Pro Val Tyr Ile Val
385                 390                 395                 400

Ala Asp Gly Ala Leu Pro Ala Gly Val Glu Glu His Leu Gln Ser Gly
                405                 410                 415

Lys Leu Asn Gly Gln Thr Thr Pro Ile Asp Val Ser Gly Leu Ser Gln
            420                 425                 430

Asn Glu Ile Gln Gly Phe Leu Leu Gly Ser His Pro Ser Ser Ser Ala
            435                 440                 445

Thr Val Ser Thr Thr Gly Val Val Ser Thr Thr Ile Ser His His
    450                 455                 460

Gln Gln Gln Gln Gln Gln Gln Gln Gln Gln Gln Gln Gln Gln Gln Gln
465                 470                 475                 480

Gln His Gln Gln Gln Gln His Pro Gly Asp Ile Val Ser Ala Ala
                485                 490                 495

Gly Val Gly Ser Thr Gly Ser Ile Val Ser Ala Ala Gln Gln Gln
            500                 505                 510

Gln Gln Gln Gln Leu Ile Ser Ile Lys Arg Glu Pro Glu Asp Leu Arg
            515                 520                 525

Lys Asp Pro Lys Asn Gly Asn Ile Ala Gly Ala Ala Thr Ala Asn Gly
530                 535                 540

Pro Gly Ser Val Ile Thr Gln Lys Ser Phe Asp Tyr Thr Glu Leu Cys
545                 550                 555                 560

Gln Pro Gly Thr Leu Ile Asp Ala Asn Gly Ser Ile Pro Val Ser Val
                565                 570                 575

Asn Ser Ile Gln Gln Arg Thr Ala Val His Gly Ser Gln Asn Ser Pro
            580                 585                 590

Thr Thr Ser Leu Val Asp Thr Thr Asn Gly Ser Thr Arg Ser Arg
            595                 600                 605

Pro Trp His Asp Phe Gly Arg Gln Asn Asp Ala Asp Lys Ile Gln Ile
    610                 615                 620

Pro Lys Ile Phe Thr Asn Val Gly Phe Arg Tyr His Leu Glu Ser Pro
625                 630                 635                 640

Ile Ser Ser Ser Gln Arg Arg Glu Asp Arg Ile Thr Tyr Ile Asn
            645                 650                 655

Lys Gly Gln Phe Tyr Gly Ile Thr Leu Glu Tyr Val His Asp Ala Glu
            660                 665                 670

Lys Pro Ile Lys Asn Thr Thr Val Lys Ser Val Ile Met Leu Met Phe
    675                 680                 685

Arg Glu Glu Lys Ser Pro Glu Asp Glu Ile Lys Ala Trp Gln Phe Trp
    690                 695                 700

His Ser Arg Gln His Ser Val Lys Gln Arg Ile Leu Asp Ala Asp Thr
705                 710                 715                 720

Lys Asn Ser Val Gly Leu Val Gly Cys Ile Glu Glu Val Ser His Asn
                725                 730                 735

Ala Ile Ala Val Tyr Trp Asn Pro Leu Glu Ser Ser Ala Lys Ile Asn
```

-continued

```
                740                 745                 750
Ile Ala Val Gln Cys Leu Ser Thr Asp Phe Ser Gln Lys Gly Gly
        755                 760                 765
Leu Pro Leu His Val Gln Ile Asp Thr Phe Glu Asp Pro Arg Asp Thr
    770                 775                 780
Ala Val Phe His Arg Gly Tyr Cys Gln Ile Lys Val Phe Cys Asp Lys
785                 790                 795                 800
Gly Ala Glu Arg Lys Thr Arg Asp Glu Glu Arg Ala Ala Lys Arg
            805                 810                 815
Lys Met Thr Ala Thr Gly Arg Lys Lys Leu Asp Glu Leu Tyr His Pro
        820                 825                 830
Val Thr Asp Arg Ser Glu Phe Tyr Gly Met Gln Asp Phe Ala Lys Pro
        835                 840                 845
Pro Val Leu Phe Ser Pro Ala Glu Asp Met Glu Lys Val Gly Gln Leu
    850                 855                 860
Gly Ile Gly Ala Ala Thr Gly Met Thr Phe Asn Pro Leu Ser Asn Gly
865                 870                 875                 880
Asn Ser Asn Ser Asn Ser His Ser Ser Leu Gln Ser Phe Tyr Gly His
            885                 890                 895
Glu Thr Asp Ser Pro Asp Leu Lys Gly Ala Ser Pro Phe Leu Leu His
        900                 905                 910
Gly Gln Lys Val Ala Thr Pro Thr Leu Lys Phe His Asn His Phe Pro
    915                 920                 925
Pro Asp Met Gln Thr Asp Lys Lys Asp His Ile Leu Asp Gln Asn Met
930                 935                 940
Leu Thr Ser Thr Pro Leu Thr Asp Phe Gly Pro Pro Met Lys Arg Gly
945                 950                 955                 960
Arg Met Thr Pro Pro Thr Ser Glu Arg Val Met Leu Tyr Val Arg Gln
            965                 970                 975
Glu Asn Glu Glu Val Tyr Thr Pro Leu His Val Val Pro Pro Thr Thr
        980                 985                 990
Ile Gly Leu Leu Asn Ala Ile Glu  Asn Lys Tyr Lys Ile  Ser Thr Thr
    995                 1000                1005
Ser Ile Asn Asn Ile Tyr Arg  Thr Asn Lys Lys Gly  Ile Thr Ala
    1010                1015                1020
Lys Ile Asp Asp Asp Met Ile  Ser Phe Tyr Cys Asn  Glu Asp Ile
    1025                1030                1035
Phe Leu Leu Glu Val Gln Gln  Ile Glu Asp Asp Leu  Tyr Asp Val
    1040                1045                1050
Thr Leu Thr Glu Leu Pro Asn  Gln
    1055                1060
```

<210> SEQ ID NO 19
<211> LENGTH: 21
<212> TYPE: DNA
<213> ORGANISM: human

<400> SEQUENCE: 19
gaagtctttg atgccctgat g                                                21

<210> SEQ ID NO 20
<211> LENGTH: 21
<212> TYPE: DNA
<213> ORGANISM: human
<220> FEATURE:
<221> NAME/KEY: misc_feature
<223> OTHER INFORMATION: human p49 mgr

<400> SEQUENCE: 20
aacccattcc ctcgacatag a       21

<210> SEQ ID NO 21
<211> LENGTH: 20
<212> TYPE: DNA
<213> ORGANISM: human

<400> SEQUENCE: 21
agcgcgatga cacaggagta       20

<210> SEQ ID NO 22
<211> LENGTH: 20
<212> TYPE: DNA
<213> ORGANISM: human

<400> SEQUENCE: 22
cgttgctatg gagacagtga       20

<210> SEQ ID NO 23
<211> LENGTH: 20
<212> TYPE: DNA
<213> ORGANISM: human

<400> SEQUENCE: 23
ccgtttaaca aggacactgc       20

<210> SEQ ID NO 24
<211> LENGTH: 20
<212> TYPE: DNA
<213> ORGANISM: murine

<400> SEQUENCE: 24
ctggaagcca ccaaatctct       20

<210> SEQ ID NO 25
<211> LENGTH: 20
<212> TYPE: DNA
<213> ORGANISM: murine

<400> SEQUENCE: 25
agcgcgatga cacaggagta       20

<210> SEQ ID NO 26
<211> LENGTH: 20
<212> TYPE: DNA
<213> ORGANISM: murine

<400> SEQUENCE: 26
agtgccagag ctgaactgat       20

<210> SEQ ID NO 27
<211> LENGTH: 20
<212> TYPE: DNA
<213> ORGANISM: murine

<400> SEQUENCE: 27
tccatgggtt ccttgagttc       20

<210> SEQ ID NO 28
<211> LENGTH: 20

```
<212> TYPE: DNA
<213> ORGANISM: murine

<400> SEQUENCE: 28
agtgccagag ctgaactgat                                                 20

<210> SEQ ID NO 29
<211> LENGTH: 20
<212> TYPE: DNA
<213> ORGANISM: murine

<400> SEQUENCE: 29 aaagggagc gagttcattg                                                  20

<210> SEQ ID NO 30
<211> LENGTH: 20
<212> TYPE: DNA
<213> ORGANISM: murine

<400> SEQUENCE: 30
agagctctcg gtgatggata                                                 20

<210> SEQ ID NO 31
<211> LENGTH: 34
<212> TYPE: DNA
<213> ORGANISM: drosophila dopa decarboxylase promoter

<400> SEQUENCE: 31
ggtggtgctc taataaccgg tttccaagat gcgc                                 34

<210> SEQ ID NO 32
<211> LENGTH: 34
<212> TYPE: DNA
<213> ORGANISM: drosophila PCNA promoter

<400> SEQUENCE: 32
gggtaaaaag tgtgaacaat caaaccagtt ggca                                 34

<210> SEQ ID NO 33
<211> LENGTH: 84
<212> TYPE: DNA
<213> ORGANISM: human

<400> SEQUENCE: 33
ggacacacac ccaaacccac acccacccac aaacacacaa accggcagtg acaacaacca     60
cccatccttc aataacagca acca                                            84

<210> SEQ ID NO 34
<211> LENGTH: 4747
<212> TYPE: DNA
<213> ORGANISM: Drosophila

<400> SEQUENCE: 34
aaaaatagaa aaacaacaa caaattggct tgaaaacgca aatgccaggc gcaacgcccc      60
cgaaccgacc cgcccctca acttttgcgc cctccagtag caatagcagc aatatgagca     120
gcagcaacat caaatgttag gccaaaatgc acaaaccgcc agcaacaaag gcagcaccaa    180
gcgaacgaaa caacaacagc tccacatacc acaaagagtg gcacattaga agcggccaaa    240
agcagccagc cgagagcatt gtgtaagcca aaggccagat gagccaggct aaaagccccc    300
agacgcacaa caacaacaac aacaactaaa acagcacaaa gagtggcgaa aggtgcaccc    360
```

```
accagcaaaa cagcaacaac ggagcaacca acaacagcag cagcagcagc agcagccaca     420
tttcagttac agctccagac tcccaggttg cagactccca aagcaaacag actccagtcc     480
acgatccagc tccagttcca ccgatccgat ccactgctcc agcgtgctcg agtgccatag     540
atcctcacca agtgccaaaa tccgcatcct gatcccaaga gctcaaggca ccccggccca     600
aaattgagct gagaacgaaa cgaaggaagt tccttagtgc catagaaagc agttaatgaa     660
acaacgacta agacgaagat cgaccatcca gaaccggagg gagctaattg cgaacgaaag     720
aaaccacaaa gtgccttcca tcaatccgtt gataagtgat atttattatg tttatacttg     780
ccagcagccg aggcagcaac agcaatagca acaaccatag gggatcacgg catcgatgat     840
cagtccacga ccaagtccta gtgcaatccg gaatccagtt caaattagtt caataagccg     900
tatctaccac gtataatgtc cacatccacc gccacaacga gcgttatcac gtccaacgag     960
ctctcgctgt ccggccacgc ccacggtcac ggtcacgccc accagttgca ccagcacacc    1020
cacagccgcc taggagttgg cgttggtgtt ggcatcctta gcgacgcatc cctatcgccc    1080
atccaacaag gcagtggcgg ccacagcggc ggaggtaaca caaacagttc accactggcg    1140
cccaacggag tgccacttct cacaacaatg caccgatcac cggactcacc gcagccagaa    1200
ttggccacca tgacgaacgt caacgtgctg gatctgcaca cggataactc caagctgtac    1260
gacaaggagg ctgtatttat atacgaaacg cccaaggtgg tgatgccagc ggatggcggg    1320
ggtggcaata attccgatga aggtcatgcc atcgatgcgc ggattgcggc ccaaatgggc    1380
aaccaagccc agcaacagca gcagcagcaa cagcagacgg aacaccagcc gctggccaag    1440
atcgagttcg atgagaacca gataatccgg gtggtgggac caaatggcga gcaacagcaa    1500
atcatctcgc gggagatcat caatggggag catcatatcc tgtcgcgaaa cgaggctggt    1560
gagcacattc tcacacggat cgtcagtgat ccctccaagt tgatgcccaa tgacaatgca    1620
gtggccacgg ccatgtacaa ccaggcccaa aagatgaaca atgatcacgg gcaggcggta    1680
tatcagacat caccattgcc gctagacgcg tctgtattgc attatagtgg cggcaatgat    1740
tcgaatgtaa ttaagacgga ggccgatatc tacgaggatc acaagaaaca tgcggctgca    1800
gcagcagctg ctgccggcgg aggatccatc atatacacca catccgatcc gaacggagtg    1860
aatgtgaaac aactgcccca tttgacggta ccccaaaaac ttgatcccga cctctatcaa    1920
gccgataagc atatagattt gatctacaac gatggcagca agacggtgat ttactccact    1980
acggatcaga agagtttgga aatatactcg ggcggcgaca tcggcagcct ggtgtccgac    2040
ggccaagtgg tggtccaggc gggactgccg tatgccacca ccaccggagc cggcggccag    2100
cccgtctata tcgtggccga cggtgccttg ccagcgggag tcgaggagca tctgcagagt    2160
ggaaagctca atggccagac cacacctatc gatgtctctg gctatcgca aaatgagatt    2220 caaggctttt tgctcggctc acacccctcg tcatcggcga cggtaagcac aaccggcgtt    2280
gtctccacga caacgatctc gcatcaccag caacagcagc agcagcagca acagcaacag    2340
cagcagcagc agcagcaaca ccagcagcag cagcaacatc ccggcgacat tgttagtgcc    2400
gctggcgtgg ggagcacggg ctccattgtc tcctctgcgg cgcaacagca gcagcagcag    2460
caactaatta gcatcaaacg agagcccgaa gacttgcgca aggatcccaa gaatggcaac    2520
attgccggtg cagcaacagc aaatggaccc ggttcggtca taacccaaaa gtcctttgat    2580
tatacggaat tgtgccagcc gggcacgctg atcgatgcca atggcagcat acccgtcagc    2640
gtgaacagca tccagcagag aacggcggtc catggcagcc agaacagtcc caccacatcg    2700
ctggtggaca ccagcaccaa tggatccacg cgatcgcggc cctggcacga ctttggacgt    2760
```

-continued

```
cagaatgatg ccgacaaaat acaaatacca aaaatcttca caaacgtggg cttccgatat    2820
cacctggaga gccccatcag ttcatcgcag aggcgcgagg acgatcgcat cacctacatc    2880
aacaagggtc aattctatgg aataacgctg gagtatgtgc acgatgcgga aaagcccatt    2940
aagaacacca ccgtcaagag tgtgatcatg ctaatgttcc gcgaggagaa gagtcccgag    3000
gatgagatca aggcctggca attctggcac agtcgtcagc attccgtgaa gcagagaatc    3060
ttggatgcag atacgaagaa ctcggttggc ctcgttggct gcatcgagga agtgtcgcac    3120
aatgccatcg ccgtctactg gaatccgctg gagagctccg ccaagatcaa cattgcggtt    3180
cagtgcttga gcacggattt cagcagtcaa aagggaggcc tgccgctgca cgtacaaatc    3240
gacacatttg aggaccccag agatacgcg gtcttccacc gcggctactg tcagataaag    3300
gtcttctgcg ataagggcgc cgaacgaaag acgcgcgatg aagagcggcg ggccgccaaa    3360
cgaaagatga cagccacggg cagaaagaag ctggacgagc tttaccatcc ggtaacggat    3420
cggtccgagt tctatggcat gcaggacttc gccaagccgc cggtgctatt ctcgcccgcc    3480
gaggacatgg agaagagctt ctacggccat gagactgact cgccggacct gaaggggggcc    3540 tcaccgttcc tgctccacgg ccagaaggtg gccacgccga cgctcaagtt ccacaaccat    3600
tttccgcccg acatgcagac cgataagaag gatcacatac tggaccagaa catgttgacc    3660
agcacacccc tgaccgactt tggtccgccg atgaagcgcg gcaggatgac gccgccgacc    3720
tcggaacgcg tgatgctgta cgtgcggcag gagaacgagg aggtgtatac accgttgcac    3780
gtggtgccgc ccaccacgat cggcctgcta aatgcgattg aaaacaaata caaaatctca    3840
acaacgagca taataacat ttatcgcaca aacaagaagg ggattactgc gaaaattgac    3900
gatgacatga tatcgttcta ctgcaacgag acatctttc tgctggaggt gcaacagatc    3960
gaggacgacc tgtacgatgt gacgctcacg gagctgccca atcagtagcg ctggcagtac    4020
gggtagcacc cgctaaccgc actcaaaaaa aaaagcaaac aaacacacaa attacgggaca    4080 caacaagttg tttcaataag ccattttcca tagagcctaa gtctaaatat cgtagttata    4140
ataatgggat ccgcaacaaa tcgagttgca acgaatgtta agaacgctaa cacaatacgc    4200
atgtaaaatg atactttaaa attgatttag ttattttagc aacaatgaga ttatctaaaa    4260
ttgtttgatc aaattttaca ttctcgctat gtctatagat aattctaagc ccgtaagccc    4320
ataagcgtaa tcgtaatcgt aatcgtaccg tgtatttatg ctcatatata aacaactata    4380
tatatatata tatatatata tatgtgcgga gtgcaacagt gtctgtccag taggagataa    4440
gtctcgtttc cgctcccctg cttatgctat gaccttaggt ccagggcaag tatgagttac    4500
cgaatctatc tattaggtgc atctaacgaa aggaatcatt agctctgcac gaactctagc    4560
cgtagcctat tgtaatccat ttgtatgttt ggcttaagcg tttacttgt tgaatataaa    4620 gtgtaaaatt atttttgaaa aaaaaaaacc cacacaaaac acaaatcgtt tgttctatat    4680
ttctgtttca aaactaactc gttacccaca atcccctctg ttatgtataa ttaggatctc    4740
tgtacac                                                              4747
```

<210> SEQ ID NO 35
<211> LENGTH: 1030
<212> TYPE: PRT
<213> ORGANISM: Drosophila
<400> SEQUENCE: 35

```
Met Ser Thr Ser Thr Ala Thr Thr Ser Val Ile Thr Ser Asn Glu Leu
1               5                   10                  15
```

-continued

Ser Leu Ser Gly His Ala His Gly His Gly His Ala His Gln Leu His
            20                  25                  30

Gln His Thr His Ser Arg Leu Gly Val Gly Val Gly Val Gly Ile Leu
            35                  40                  45

Ser Asp Ala Ser Leu Ser Pro Ile Gln Gln Gly Ser Gly Gly His Ser
 50                  55                  60

Gly Gly Gly Asn Thr Asn Ser Ser Pro Leu Ala Pro Asn Gly Val Pro
 65                  70                  75                  80

Leu Leu Thr Thr Met His Arg Ser Pro Asp Ser Pro Gln Pro Glu Leu
                85                  90                  95

Ala Thr Met Thr Asn Val Asn Val Leu Asp Leu His Thr Asp Asn Ser
            100                 105                 110

Lys Leu Tyr Asp Lys Glu Ala Val Phe Ile Tyr Glu Thr Pro Lys Val
            115                 120                 125

Val Met Pro Ala Asp Gly Gly Gly Asn Asn Ser Asp Glu Gly His
            130                 135                 140

Ala Ile Asp Ala Arg Ile Ala Ala Gln Met Gly Asn Gln Ala Gln Gln
145                 150                 155                 160

Gln Gln Gln Gln Gln Gln Thr Glu His Gln Pro Leu Ala Lys Ile
                165                 170                 175

Glu Phe Asp Glu Asn Gln Ile Ile Arg Val Val Gly Pro Asn Gly Glu
            180                 185                 190

Gln Gln Gln Ile Ile Ser Arg Glu Ile Ile Asn Gly Glu His His Ile
            195                 200                 205

Leu Ser Arg Asn Glu Ala Gly Glu His Ile Leu Thr Arg Ile Val Ser
210                 215                 220

Asp Pro Ser Lys Leu Met Pro Asn Asp Asn Ala Val Ala Thr Ala Met
225                 230                 235                 240

Tyr Asn Gln Ala Gln Lys Met Asn Asn Asp His Gly Gln Ala Val Tyr
            245                 250                 255

Gln Thr Ser Pro Leu Pro Leu Asp Ala Ser Val Leu His Tyr Ser Gly
            260                 265                 270

Gly Asn Asp Ser Asn Val Ile Lys Thr Glu Ala Asp Ile Tyr Glu Asp
            275                 280                 285

His Lys Lys His Ala Ala Ala Ala Ala Ala Ala Gly Gly Gly Ser
            290                 295                 300

Ile Ile Tyr Thr Thr Ser Asp Pro Asn Gly Val Asn Val Lys Gln Leu
305                 310                 315                 320

Pro His Leu Thr Val Pro Gln Lys Leu Asp Pro Asp Leu Tyr Gln Ala
            325                 330                 335

Asp Lys His Ile Asp Leu Ile Tyr Asn Asp Gly Ser Lys Thr Val Ile
            340                 345                 350

Tyr Ser Thr Thr Asp Gln Lys Ser Leu Glu Ile Tyr Ser Gly Gly Asp
            355                 360                 365

Ile Gly Ser Leu Val Ser Asp Gly Gln Val Val Gln Ala Gly Leu
            370                 375                 380

Pro Tyr Ala Thr Thr Thr Gly Ala Gly Gly Gln Pro Val Tyr Ile Val
385                 390                 395                 400

Ala Asp Gly Ala Leu Pro Ala Gly Val Glu Glu His Leu Gln Ser Gly
            405                 410                 415

Lys Leu Asn Gly Gln Thr Thr Pro Ile Asp Val Ser Gly Leu Ser Gln
            420                 425                 430

-continued

```
Asn Glu Ile Gln Gly Phe Leu Leu Gly Ser His Pro Ser Ser Ser Ala
        435                 440                 445

Thr Val Ser Thr Thr Gly Val Val Ser Thr Thr Ile Ser His His
    450                 455                 460

Gln Gln Gln Gln Gln Gln Gln Gln Gln Gln Gln Gln Gln Gln Gln Gln
465                 470                 475                 480

Gln His Gln Gln Gln Gln His Pro Gly Asp Ile Val Ser Ala Ala
            485                 490                 495

Gly Val Gly Ser Thr Gly Ser Ile Val Ser Ala Ala Gln Gln Gln
            500                 505                 510

Gln Gln Gln Gln Leu Ile Ser Ile Lys Arg Glu Pro Glu Asp Leu Arg
        515                 520                 525

Lys Asp Pro Lys Asn Gly Asn Ile Ala Gly Ala Ala Thr Ala Asn Gly
530                 535                 540

Pro Gly Ser Val Ile Thr Gln Lys Ser Phe Asp Tyr Thr Glu Leu Cys
545                 550                 555                 560

Gln Pro Gly Thr Leu Ile Asp Ala Asn Gly Ser Ile Pro Val Ser Val
                565                 570                 575

Asn Ser Ile Gln Gln Arg Thr Ala Val His Gly Ser Gln Asn Ser Pro
            580                 585                 590

Thr Thr Ser Leu Val Asp Thr Ser Thr Asn Gly Ser Thr Arg Ser Arg
            595                 600                 605

Pro Trp His Asp Phe Gly Arg Gln Asn Asp Ala Asp Lys Ile Gln Ile
        610                 615                 620

Pro Lys Ile Phe Thr Asn Val Gly Phe Arg Tyr His Leu Glu Ser Pro
625                 630                 635                 640

Ile Ser Ser Ser Gln Arg Arg Glu Asp Asp Arg Ile Thr Tyr Ile Asn
                645                 650                 655

Lys Gly Gln Phe Tyr Gly Ile Thr Leu Glu Tyr Val His Asp Ala Glu
            660                 665                 670

Lys Pro Ile Lys Asn Thr Thr Val Lys Ser Val Ile Met Leu Met Phe
        675                 680                 685

Arg Glu Glu Lys Ser Pro Glu Asp Glu Ile Lys Ala Trp Gln Phe Trp
690                 695                 700

His Ser Arg Gln His Ser Val Lys Gln Arg Ile Leu Asp Ala Asp Thr
705                 710                 715                 720

Lys Asn Ser Val Gly Leu Val Gly Cys Ile Glu Glu Val Ser His Asn
                725                 730                 735

Ala Ile Ala Val Tyr Trp Asn Pro Leu Glu Ser Ser Ala Lys Ile Asn
            740                 745                 750

Ile Ala Val Gln Cys Leu Ser Thr Asp Phe Ser Ser Gln Lys Gly Gly
        755                 760                 765

Leu Pro Leu His Val Gln Ile Asp Thr Phe Glu Asp Pro Arg Asp Thr
770                 775                 780

Ala Val Phe His Arg Gly Tyr Cys Gln Ile Lys Val Phe Cys Asp Lys
785                 790                 795                 800

Gly Ala Glu Arg Lys Thr Arg Asp Glu Glu Arg Ala Ala Lys Arg
                805                 810                 815

Lys Met Thr Ala Thr Gly Arg Lys Lys Leu Asp Glu Leu Tyr His Pro
            820                 825                 830

Val Thr Asp Arg Ser Glu Phe Tyr Gly Met Gln Asp Phe Ala Lys Pro
        835                 840                 845

Pro Val Leu Phe Ser Pro Ala Glu Asp Met Glu Lys Ser Phe Tyr Gly
```

```
       850            855              860
His Glu Thr Asp Ser Pro Asp Leu Lys Gly Ala Ser Pro Phe Leu Leu
865                 870                 875                 880

His Gly Gln Lys Val Ala Thr Pro Thr Leu Lys Phe His Asn His Phe
                885                 890                 895

Pro Pro Asp Met Gln Thr Asp Lys Lys Asp His Ile Leu Asp Gln Asn
            900                 905                 910

Met Leu Thr Ser Thr Pro Leu Thr Asp Phe Gly Pro Pro Met Lys Arg
        915                 920                 925

Gly Arg Met Thr Pro Pro Thr Ser Glu Arg Val Met Leu Tyr Val Arg
    930                 935                 940

Gln Glu Asn Glu Glu Val Tyr Thr Pro Leu His Val Val Pro Pro Thr
945                 950                 955                 960

Thr Ile Gly Leu Leu Asn Ala Ile Glu Asn Lys Tyr Lys Ile Ser Thr
                965                 970                 975

Thr Ser Ile Asn Asn Ile Tyr Arg Thr Asn Lys Lys Gly Ile Thr Ala
            980                 985                 990

Lys Ile Asp Asp Met Ile Ser  Phe Tyr Cys Asn Glu  Asp Ile Phe
        995                 1000                1005

Leu Leu  Glu Val Gln Gln Ile  Glu Asp Asp Leu Tyr  Asp Val Thr
    1010                1015                1020

Leu Thr  Glu Leu Pro Asn Gln
    1025                1030

<210> SEQ ID NO 36
<211> LENGTH: 5650
<212> TYPE: DNA
<213> ORGANISM: Drosophila

<400> SEQUENCE: 36
aaaaatagaa aaacaacaa  caaattggct tgaaaacgca aatgccaggc gcaacgcccc      60
cgaaccgacc cgccccctca acttttgcgc cctccagtag caatagcagc aatatgagca    120
gcagcaacat caaatgttag gccaaaatgc acaaaccgcc agcaacaaag gcagcaccaa    180
gcgaacgaaa caacaacagc tccacatacc acaaagagtg gcacattaga agcggccaaa    240
agcagccagc cgagagcatt gtgtaagcca aaggcccaga gagccaggct aaaagccccc    300
agacgcacaa caacaacaac aacaactaaa acagcacaaa gagtggcgaa aggtgcaccc    360
accagcaaaa cagcaacaac ggagcaacca acaacagcag cagcagcagc agcagccaca    420
tttcagttac agctccagac tcccaggttg cagactccca aagcaaacag actccagtcc    480
acgatccagc tccagttcca ccgatccgat ccactgctcc agcgtgctcg agtgccatag    540
atcctcacca agtgccaaaa tccgcatcct gatcccaaga gctcaaggca ccccggccca    600
aaattgagct gagaacgaaa cgaaggaagt tccttagtgc catagaaagc agttaatgaa    660
acaacgacta agacgaagat cgaccatcca gaaccggagg gagctaattg cgaacgaaag    720
aaaccacaaa gtgccttcca tcaatccgtt gataagtgat atttattatg tttatacttg    780
ccagcagccg aggcagcaac agcaatagca acaaccatag gggatcacgg catcgatgat    840
cagtccacga ccaagtccta gtgcaatccg gaatccagtt caaattagtt caataagccg    900
tatctaccac gtataatgtc cacatccacc gccacaacga gcgttatcac gtccaacgag    960
ctctcgctgt ccggccacgc ccacggtcac ggtcacgccc accagttgca ccagcacacc   1020
cacagccgcc taggagttgg cgttggtgtt ggcatcctta gcgacgcatc cctatcgccc   1080
```

```
atccaacaag gcagtggcgg ccacagcggc ggaggtaaca caaacagttc accactggcg      1140
cccaacggag tgccacttct cacaacaatg caccgatcac cggactcacc gcagccagaa      1200
ttggccacca tgacgaacgt caacgtgctg gatctgcaca cggataactc caagctgtac      1260
gacaaggagg ctgtatttat atacgaaacg cccaaggtgg tgatgccagc ggatggcggg      1320
ggtggcaata attccgatga aggtcatgcc atcgatgcgc ggattgcggc ccaaatgggc      1380
aaccaagccc agcaacagca gcagcagcaa cagcagacga acaccagcc gctggccaag      1440 atcgagttcg atgagaacca gataatccgg gtggtgggac caaatggcga gcaacagcaa      1500
atcatctcgc gggagatcat caatgggag catcatatcc tgtcgcgaaa cgaggctggt      1560
gagcacattc tcacacggat cgtcagtgat ccctccaagt tgatgcccaa tgacaatgca      1620
gtggccacgg ccatgtacaa ccaggcccaa aagatgaaca atgatcacgg gcaggcggta      1680
tatcagacat caccattgcc gctagacgcg tctgtattgc attatagtgg cggcaatgat      1740
tcgaatgtaa ttaagacgga ggccgatatc tacgaggatc acaagaaaca tgcggctgca      1800
gcagcagctg ctgccggcgg aggatccatc atatacacca catccgatcc gaacggagtg      1860
aatgtgaaac aactgcccca tttgacggta ccccaaaaac ttgatcccga cctctatcaa      1920
gccgataagc atatagattt gatctacaac gatggcagca agacggtgat ttactccact      1980
acggatcaga gagtttgga atatactcg ggcggcgaca tcggcagcct ggtgtccgac      2040
ggccaagtgg tggtccaggc gggactgccg tatgccacca ccaccggagc cggcggccag      2100
cccgtctata tcgtggccga cggtgccttg ccagcgggag tcgaggagca tctgcagagt      2160
ggaaagctca atggccagac cacacctatc gatgtctctg gcctatcgca aaatgagatt      2220
caaggctttt tgctcggctc acacccctcg tcatcggcga cggtaagcac aaccggcgtt      2280
gtctccacga caacgatctc gcatcaccag caacagcagc agcagcagca acagcaacag      2340
cagcagcagc agcagcaaca ccagcagcag cagcaacatc ccggcgacat tgttagtgcc      2400
gctggcgtgg ggagcacggg ctccattgtc tcctctgcgg cgcaacagca gcagcagcag      2460
caactaatta gcatcaaacg agagcccgaa gacttgcgca aggatcccaa gaatggcaac      2520
attgccggtg cagcaacagc aaatggaccc ggttcggtca taacccaaaa gatcttgcac      2580
gtggatgcac caacggcaag tgaagctgat aggcccagca cacccagcag cagcatcaac      2640
agcactgaaa acactgaatc ggactcacag tcagtatcag gatcagaatc aggatcgccg      2700
ggagccagga ccacagccac actagagatg tatgcaacca cggcggcac acagatctat      2760 ctacagacct cacatcccag cacggcgagc ggagcggggcg gcggcgccgg accgctggaa      2820
gccgccggcg gcggcggtgt gtccatgcag gcgcaaagtc ccagtccggg tccctatatc      2880
acggccaatg actatggcat gtacacggcc agtcgcctgc cacccggtcc ccgcccacc      2940 agcaccacca cgtttatagc ggagccctcc tactatcggg aatactttgc accggatggc      3000
caaggtggct atgtgccggc cagcacgagg tctttgtatg cgacgtgga cgtatccgta      3060 tctcagcccg gcggagtggt cacctatgag ggccgctttg ccggcagcgt tccccgccc      3120 gccaccacca ccgtgctaac cagcgtgcat caccaccagc aacagcagca gcaacaacag      3180
cagcatcaac agcagcagca gcagcaacag caccaccagc agcaacagca ccattcgcag      3240
gatggcaaga gcaatggcgg agcaacgcca ctctatgcca aagccattac ggcggcgggt      3300
ctaacggtgg attttgccaag tccggattcg ggcattggta cggatgccat tacaccgcgg      3360
gatcagacaa atatccaaca gtcctttgat tatacggaat tgtgccagcc gggcacgctg      3420
atcgatgcca atggcagcat acccgtcagc gtgaacagca tccagcagag aacggcggtc      3480
```

-continued

```
catggcagcc agaacagtcc caccacatcg ctggtggaca ccagcaccaa tggatccacg    3540
cgatcgcggc cctggcacga cttTggacgt cagaatgatg ccgacaaaat acaaatacca    3600
aaaatcttca caaacgtggg cttccgatat cacctggaga gccccatcag ttcatcgcag    3660
aggcgcgagg acgatcgcat cacctacatc aacaagggtc aattctatgg aataacgctg    3720
gagtatgtgc acgatgcgga aaagcccatt aagaacacca ccgtcaagag tgtgatcatg    3780
ctaatgttcc gcgaggagaa gagtcccgag gatgagatca aggcctggca attctggcac    3840
agtcgtcagc attccgtgaa gcagagaatc ttggatgcag atacgaagaa ctcggttggc    3900
ctcgttggct gcatcgagga agtgtcgcac aatgccatcg ccgtctactg gaatccgctg    3960
gagagctccg ccaagatcaa cattgcggtt cagtgcttga gcacggattt cagcagtcaa    4020
aagggaggcc tgccgctgca cgtacaaatc gacacatttg aggaccccag agatacggcg    4080
gtcttccacc gcggctactg tcagataaag gtcttctgcg ataagggcgc cgaacgaaag    4140
acgcgcgatg aagagcggcg ggccgccaaa cgaaagatga cagccacggg cagaaagaag    4200
ctggacgagc tttaccatcc ggtaacggat cggtccgagt tctatggcat gcaggacttc    4260
gccaagccgc cggtgctatt ctcgcccgcc gaggacatga gaaggtagg tcagctgggc    4320
attggcgctg ccaccggcat gacattcaac ccctgagca acggcaactc caactccaac    4380
tcgcactcgt ccttgcagag cttctacggc catgagactg actcgccgga cctgaagggg    4440
gcctcaccgt tcctgctcca cggccagaag gtggccacgc cgacgctcaa gttccacaac    4500
cattttccgc ccgacatgca gaccgataag aaggatcaca tactgaccca gaacatgttg    4560
accagcacac ccctgaccga cttTggtccg ccgatgaagc gcggcaggat gacgccgccg    4620
acctcggaac gcgtgatgct gtacgtgcgg caggagaacg aggaggtgta tacaccgttg    4680
cacgtggtgc cgcccaccac gatcggcctg ctaaatgcga ttgaaaacaa atacaaaatc    4740
tcaacaacga gcataaataa catttatcgc acaaacaaga aggggattac tgcgaaaatt    4800
gacgatgaca tgatatcgtt ctactgcaac gaggacatct ttctgctgga ggtgcaacag    4860
atcgaggacg acctgtacga tgtgacgctc acggagctgc ccaatcagta gcgctggcag    4920
tacgggtagc acccgctaac cgcactcaaa aaaaaaagca aacaaacaca caaattacgg    4980
acacaacaag ttgtttcaat aagccatttt ccatagagcc taagtctaaa tatcgtagtt    5040
ataataatgg gatccgcaac aaatcgagtt gcaacgaatg ttaagaacgc taacacaata    5100
cgcatgtaaa atgatacttt aaaattgatt tagttatttt agcaacaatg agattatcta    5160
aaattgtttg atcaaatttt acattctcgc tatgtctata gataattcta agcccgtaag    5220
cccataagcg taatcgtaat cgtaatcgta ccgtgtattt atgctcatat ataaacaact    5280
atatatatat atatatatat atatatgtgc ggagtgcaac agtgtctgtc cagtaggaga    5340
taagtctcgt ttccgctccc ctgcttatgc tatgacctta ggtccagggc aagtatgagt    5400
taccgaatct atctattagg tgcatctaac gaaaggaatc attagctctg cacgaactct    5460
agccgtagcc tattgtaatc catttgtatg tttggcttaa gcgttttact tgttgaatat    5520
aaagtgtaaa attattttTg aaaaaaaaaa acccacacaa aacacaaatc gtttgttcta    5580
tatttctgtt tcaaaactaa ctcgttaccc acaatcccct ctgttatgta taattaggat    5640
ctctgtacac                                                           5650
```

<210> SEQ ID NO 37
<211> LENGTH: 1331
<212> TYPE: PRT

<213> ORGANISM: Drosophila

<400> SEQUENCE: 37

```
Met Ser Thr Ser Thr Ala Thr Thr Ser Val Ile Thr Ser Asn Glu Leu
1               5                   10                  15

Ser Leu Ser Gly His Ala His Gly His Gly His Ala His Gln Leu His
            20                  25                  30

Gln His Thr His Ser Arg Leu Gly Val Gly Val Gly Val Gly Ile Leu
        35                  40                  45

Ser Asp Ala Ser Leu Ser Pro Ile Gln Gln Gly Ser Gly His Ser
    50                  55                  60

Gly Gly Gly Asn Thr Asn Ser Ser Pro Leu Ala Pro Asn Gly Val Pro
65                  70                  75                  80

Leu Leu Thr Thr Met His Arg Ser Pro Asp Ser Pro Gln Pro Glu Leu
                85                  90                  95

Ala Thr Met Thr Asn Val Asn Val Leu Asp Leu His Thr Asp Asn Ser
            100                 105                 110

Lys Leu Tyr Asp Lys Glu Ala Val Phe Ile Tyr Glu Thr Pro Lys Val
        115                 120                 125

Val Met Pro Ala Asp Gly Gly Gly Asn Asn Ser Asp Glu Gly His
130                 135                 140

Ala Ile Asp Ala Arg Ile Ala Ala Gln Met Gly Asn Gln Ala Gln Gln
145                 150                 155                 160

Gln Gln Gln Gln Gln Gln Thr Glu His Gln Pro Leu Ala Lys Ile
                165                 170                 175

Glu Phe Asp Glu Asn Gln Ile Ile Arg Val Val Gly Pro Asn Gly Glu
            180                 185                 190

Gln Gln Gln Ile Ile Ser Arg Glu Ile Ile Asn Gly Glu His His Ile
        195                 200                 205

Leu Ser Arg Asn Glu Ala Gly Glu His Ile Leu Thr Arg Ile Val Ser
    210                 215                 220

Asp Pro Ser Lys Leu Met Pro Asn Asp Asn Ala Val Ala Thr Ala Met
225                 230                 235                 240

Tyr Asn Gln Ala Gln Lys Met Asn Asn Asp His Gly Gln Ala Val Tyr
                245                 250                 255

Gln Thr Ser Pro Leu Pro Leu Asp Ala Ser Val Leu His Tyr Ser Gly
            260                 265                 270

Gly Asn Asp Ser Asn Val Ile Lys Thr Glu Ala Asp Ile Tyr Glu Asp
        275                 280                 285

His Lys Lys His Ala Ala Ala Ala Ala Ala Gly Gly Gly Ser
    290                 295                 300

Ile Ile Tyr Thr Thr Ser Asp Pro Asn Gly Val Asn Val Lys Gln Leu
305                 310                 315                 320

Pro His Leu Thr Val Pro Gln Lys Leu Asp Pro Asp Leu Tyr Gln Ala
                325                 330                 335

Asp Lys His Ile Asp Leu Ile Tyr Asn Asp Gly Ser Lys Thr Val Ile
            340                 345                 350

Tyr Ser Thr Thr Asp Gln Lys Ser Leu Glu Ile Tyr Ser Gly Gly Asp
        355                 360                 365

Ile Gly Ser Leu Val Ser Asp Gly Gln Val Val Gln Ala Gly Leu
    370                 375                 380

Pro Tyr Ala Thr Thr Thr Gly Ala Gly Gly Gln Pro Val Tyr Ile Val
385                 390                 395                 400
```

-continued

```
Ala Asp Gly Ala Leu Pro Ala Gly Val Glu His Leu Gln Ser Gly
            405                 410                 415
Lys Leu Asn Gly Gln Thr Thr Pro Ile Asp Val Ser Gly Leu Ser Gln
            420                 425                 430
Asn Glu Ile Gln Gly Phe Leu Leu Gly Ser His Pro Ser Ser Ser Ala
            435                 440                 445
Thr Val Ser Thr Thr Gly Val Val Ser Thr Thr Ile Ser His His
            450                 455                 460
Gln Gln Gln Gln Gln Gln Gln Gln Gln Gln Gln Gln Gln Gln Gln
465                 470                 475                 480
Gln His Gln Gln Gln Gln His Pro Gly Asp Ile Val Ser Ala Ala
            485                 490                 495
Gly Val Gly Ser Thr Gly Ser Ile Val Ser Ser Ala Gln Gln Gln
            500                 505                 510
Gln Gln Gln Gln Leu Ile Ser Ile Lys Arg Glu Pro Glu Asp Leu Arg
            515                 520                 525
Lys Asp Pro Lys Asn Gly Asn Ile Ala Gly Ala Ala Thr Ala Asn Gly
            530                 535                 540
Pro Gly Ser Val Ile Thr Gln Lys Ile Leu His Val Asp Ala Pro Thr
545                 550                 555                 560
Ala Ser Glu Ala Asp Arg Pro Ser Thr Pro Ser Ser Ser Ile Asn Ser
            565                 570                 575
Thr Glu Asn Thr Glu Ser Asp Ser Gln Ser Val Ser Gly Ser Glu Ser
            580                 585                 590
Gly Ser Pro Gly Ala Arg Thr Thr Ala Thr Leu Glu Met Tyr Ala Thr
            595                 600                 605
Thr Gly Gly Thr Gln Ile Tyr Leu Gln Thr Ser His Pro Ser Thr Ala
            610                 615                 620
Ser Gly Ala Gly Gly Ala Gly Pro Ala Gly Ala Ala Gly Gly Gly
625                 630                 635                 640
Gly Val Ser Met Gln Ala Gln Ser Pro Ser Pro Gly Pro Tyr Ile Thr
            645                 650                 655
Ala Asn Asp Tyr Gly Met Tyr Thr Ala Ser Arg Leu Pro Pro Gly Pro
            660                 665                 670
Pro Pro Thr Ser Thr Thr Thr Phe Ile Ala Glu Pro Ser Tyr Tyr Arg
            675                 680                 685
Glu Tyr Phe Ala Pro Asp Gly Gln Gly Gly Tyr Val Pro Ala Ser Thr
            690                 695                 700
Arg Ser Leu Tyr Gly Asp Val Asp Val Ser Val Ser Gln Pro Gly Gly
705                 710                 715                 720
Val Val Thr Tyr Glu Gly Arg Phe Ala Gly Ser Val Pro Pro Ala
            725                 730                 735
Thr Thr Thr Val Leu Thr Ser Val His His Gln Gln Gln Gln
            740                 745                 750
Gln Gln Gln Gln His Gln Gln Gln Gln Gln His His Gln
            755                 760                 765
Gln Gln Gln His His Ser Gln Asp Gly Lys Ser Asn Gly Gly Ala Thr
            770                 775                 780
Pro Leu Tyr Ala Lys Ala Ile Thr Ala Ala Gly Leu Thr Val Asp Leu
785                 790                 795                 800
Pro Ser Pro Asp Ser Gly Ile Gly Thr Asp Ala Ile Thr Pro Arg Asp
            805                 810                 815
Gln Thr Asn Ile Gln Gln Ser Phe Asp Tyr Thr Glu Leu Cys Gln Pro
```

-continued

```
                820                 825                 830
Gly Thr Leu Ile Asp Ala Asn Gly Ser Ile Pro Val Ser Val Asn Ser
        835                 840                 845
Ile Gln Gln Arg Thr Ala Val His Gly Ser Gln Asn Ser Pro Thr Thr
    850                 855                 860
Ser Leu Val Asp Thr Ser Thr Asn Gly Ser Thr Arg Ser Arg Pro Trp
865                 870                 875                 880
His Asp Phe Gly Arg Gln Asn Asp Ala Asp Lys Ile Gln Ile Pro Lys
                885                 890                 895
Ile Phe Thr Asn Val Gly Phe Arg Tyr His Leu Glu Ser Pro Ile Ser
        900                 905                 910
Ser Ser Gln Arg Arg Glu Asp Asp Arg Ile Thr Tyr Ile Asn Lys Gly
    915                 920                 925
Gln Phe Tyr Gly Ile Thr Leu Glu Tyr Val His Asp Ala Glu Lys Pro
930                 935                 940
Ile Lys Asn Thr Thr Val Lys Ser Val Ile Met Leu Met Phe Arg Glu
945                 950                 955                 960
Glu Lys Ser Pro Glu Asp Glu Ile Lys Ala Trp Gln Phe Trp His Ser
                965                 970                 975
Arg Gln His Ser Val Lys Gln Arg Ile Leu Asp Ala Asp Thr Lys Asn
            980                 985                 990
Ser Val Gly Leu Val Gly Cys Ile Glu Glu Val Ser His Asn Ala Ile
        995                1000                1005
Ala Val Tyr Trp Asn Pro Leu Glu Ser Ser Ala Lys Ile Asn Ile
    1010                1015                1020
Ala Val Gln Cys Leu Ser Thr Asp Phe Ser Ser Gln Lys Gly Gly
    1025                1030                1035
Leu Pro Leu His Val Gln Ile Asp Thr Phe Glu Asp Pro Arg Asp
    1040                1045                1050
Thr Ala Val Phe His Arg Gly Tyr Cys Gln Ile Lys Val Phe Cys
    1055                1060                1065
Asp Lys Gly Ala Glu Arg Lys Thr Arg Asp Glu Glu Arg Arg Ala
    1070                1075                1080
Ala Lys Arg Lys Met Thr Ala Thr Gly Arg Lys Lys Leu Asp Glu
    1085                1090                1095
Leu Tyr His Pro Val Thr Asp Arg Ser Glu Phe Tyr Gly Met Gln
    1100                1105                1110
Asp Phe Ala Lys Pro Pro Val Leu Phe Ser Pro Ala Glu Asp Met
    1115                1120                1125
Glu Lys Val Gly Gln Leu Gly Ile Gly Ala Ala Thr Gly Met Thr
    1130                1135                1140
Phe Asn Pro Leu Ser Asn Gly Asn Ser Asn Ser Asn Ser His Ser
    1145                1150                1155
Ser Leu Gln Ser Phe Tyr Gly His Glu Thr Asp Ser Pro Asp Leu
    1160                1165                1170
Lys Gly Ala Ser Pro Phe Leu Leu His Gly Gln Lys Val Ala Thr
    1175                1180                1185
Pro Thr Leu Lys Phe His Asn His Phe Pro Pro Asp Met Gln Thr
    1190                1195                1200
Asp Lys Lys Asp His Ile Leu Asp Gln Asn Met Leu Thr Ser Thr
    1205                1210                1215
Pro Leu Thr Asp Phe Gly Pro Pro Met Lys Arg Gly Arg Met Thr
    1220                1225                1230
```

-continued

Pro Pro Thr Ser Glu Arg Val Met Leu Tyr Val Arg Gln Glu Asn
    1235                1240                1245

Glu Glu Val Tyr Thr Pro Leu His Val Val Pro Pro Thr Thr Ile
    1250                1255                1260

Gly Leu Leu Asn Ala Ile Glu Asn Lys Tyr Lys Ile Ser Thr Thr
    1265                1270                1275

Ser Ile Asn Asn Ile Tyr Arg Thr Asn Lys Lys Gly Ile Thr Ala
    1280                1285                1290

Lys Ile Asp Asp Met Ile Ser Phe Tyr Cys Asn Glu Asp Ile
    1295                1300                1305

Phe Leu Leu Glu Val Gln Gln Ile Glu Asp Asp Leu Tyr Asp Val
    1310                1315                1320

Thr Leu Thr Glu Leu Pro Asn Gln
    1325                1330

<210> SEQ ID NO 38
<211> LENGTH: 5557
<212> TYPE: DNA
<213> ORGANISM: Drosophila

<400> SEQUENCE: 38

| | |
|---|---|
| aaaaatagaa aaacaacaa caaattggct tgaaaacgca aatgccaggc gcaacgcccc | 60 |
| cgaaccgacc cgccccctca acttttgcgc cctccagtag caatagcagc aatatgagca | 120 |
| gcagcaacat caaatgttag gccaaaatgc acaaaccgcc agcaacaaag gcagcaccaa | 180 |
| gcgaacgaaa caacaacagc tccacatacc acaaagagtg gcacattaga agcggccaaa | 240 |
| agcagccagc cgagagcatt gtgtaagcca aggcccaga gagccaggct aaaagccccc | 300 |
| agacgcacaa caacaacaac aacaactaaa acagcacaaa gagtggcgaa aggtgcaccc | 360 |
| accagcaaaa cagcaacaac ggagcaacca acaacagcag cagcagcagc agcagccaca | 420 |
| tttcagttac agctccagac tcccaggttg cagactccca aagcaaacag actccagtcc | 480 |
| acgatccagc tccagttcca ccgatccgat ccactgctcc agcgtgctcg agtgccatag | 540 |
| atcctcacca agtgccaaaa tccgcatcct gatcccaaga gctcaaggca ccccggccca | 600 |
| aaattgagct gagaacgaaa cgaaggaagt tccttagtgc catagaaagc agttaatgaa | 660 |
| acaacgacta agacgaagat cgaccatcca gaaccggagg gagctaattg cgaacgaaag | 720 |
| aaaccacaaa gtgccttcca tcaatccgtt gataagtgat atttattatg tttatacttg | 780 |
| ccagcagccg aggcagcaac agcaatagca acaaccatag gggatcacgg catcgatgat | 840 |
| cagtccacga ccaagtccta gtgcaatccg gaatccagtt caaattagtt caataagccg | 900 |
| tatctaccac gtataatgtc cacatccacc gccacaacga gcgttatcac gtccaacgag | 960 |
| ctctcgctgt ccggccacgc ccacggtcac ggtcacgccc accagttgca ccagcacacc | 1020 |
| cacagccgcc taggagttgg cgttggtgtt ggcatcctta gcgacgcatc cctatcgccc | 1080 |
| atccaacaag gcagtggcgg ccacagcggc ggaggtaaca caaacagttc accactggcg | 1140 |
| cccaacggag tgccacttct cacaacaatg caccgatcac cggactcacc gcagccagaa | 1200 |
| ttggccacca tgacgaacgt caacgtgctg gatctgcaca cggataactc caagctgtac | 1260 |
| gacaaggagg ctgtatttat atacgaaacg cccaaggtgg tgatgccagc ggatggcggg | 1320 |
| ggtggcaata attccgatga aggtcatgcc atcgatgcgc ggattgcggc ccaaatgggc | 1380 |
| aaccaagccc agcaacagca gcagcagcaa cagcagacgg aacaccagcc gctggccaag | 1440 |
| atcgagttcg atgagaacca gataatccgg gtggtgggac caaatggcga gcaacagcaa | 1500 |

-continued

```
atcatctcgc gggagatcat caatggggag catcatatcc tgtcgcgaaa cgaggctggt    1560
gagcacattc tcacacggat cgtcagtgat ccctccaagt tgatgcccaa tgacaatgca    1620
gtggccacgg ccatgtacaa ccaggcccaa aagatgaaca atgatcacgg gcaggcggta    1680
tatcagacat caccattgcc gctagacgcg tctgtattgc attatagtgg cggcaatgat    1740
tcgaatgtaa ttaagacgga ggccgatatc tacgaggatc acaagaaaca tgcggctgca    1800
gcagcagctg ctgccggcgg aggatccatc atatacacca catccgatcc gaacggagtg    1860
aatgtgaaac aactgcccca tttgacggta ccccaaaaac ttgatcccga cctctatcaa    1920
gccgataagc atatagattt gatctacaac gatggcagca agacggtgat ttactccact    1980
acggatcaga agagtttgga aatatactcg ggcggcgaca tcggcagcct ggtgtccgac    2040
ggccaagtgg tggtccaggc gggactgccg tatgccacca ccaccggagc cggcggccag    2100
cccgtctata tcgtggccga cggtgccttg ccagcgggag tcgaggagca tctgcagagt    2160
ggaaagctca atggccagac cacacctatc gatgtctctg gcctatcgca aaatgagatt    2220
caaggctttt tgctcggctc acaccccctcg tcatcggcga cggtaagcac aaccggcgtt    2280
gtctccacga caacgatctc gcatcaccag caacagcagc agcagcagca acagcaacag    2340
cagcagcagc agcagcaaca ccagcagcag cagcaacatc ccggcgacat tgttagtgcc    2400
gctggcgtgg ggagcacggg ctccattgtc tcctctgcgg cgcaacagca gcagcagcag    2460
caactaatta gcatcaaacg agagcccgaa gacttgcgca aggatcccaa gaatggcaac    2520
attgccggtg cagcaacagc aaatggaccc ggttcggtca taaccaaaa gatcttgcac    2580 gtggatgcac caacggcaag tgaagctgat aggcccagca cacccagcag cagcatcaac    2640
agcactgaaa acactgaatc ggactcacag tcagtatcag gatcagaatc aggatcgccg    2700
ggagccagga ccacagccac actagagatg tatgcaacca cgggcggcac acagatctat    2760
ctacagacct cacatcccag cacggcgagc ggagcgggcg gcggcgccgg acccgctgga    2820
gccgccggcg gcggcggtgt gtccatgcag gcgcaaagtc ccagtccggg tccctatatc    2880
acggccaatg actatggcat gtacacggcc agtcgcctgc cacccggtcc cccgcccacc    2940
agcaccacca cgtttatagc ggagccctcc tactatcggg aatactttgc accggatggc    3000
caaggtggct atgtgccggc cagcacgagg tctttgtatg cgacgtgga cgtatccgta    3060 tctcagcccg gcggagtggt cacctatgag ggccgctttg ccggcagcgt tcccccgccc    3120
gccaccacca ccgtgctaac cagcgtgcat caccaccagc aacagcagca gcaacaacag    3180
cagcatcaac agcagcagca gcagcaacag caccaccagc agcaacagca ccattcgcag    3240
gatggcaaga gcaatggcgg agcaacgcca ctctatgcca aagccattac ggcggcgggt    3300
ctaacggtgg atttgccaag tccggattcg ggcattggta cggatgccat tacaccgcgg    3360
gatcagacaa atatccaaca gtcctttgat tatacggaat tgtgccagcc gggcacgctg    3420
atcgatgcca atggcagcat acccgtcagc gtgaacagca tccagcagag aacggcggtc    3480
catggcagcc agaacagtcc caccacatcg ctggtggaca ccagcaccaa tggatccacg    3540
cgatcgcggc cctggcacga ctttggacgt cagaatgatg ccgacaaaat acaaatacca    3600
aaaatcttca caacgtggg cttccgtatat cacctggaga gccccatcag ttcatcgcag    3660
aggcgcgagg acgatcgcat cacctacatc aacaagggtc aattctatgg aataacgctg    3720
gagtatgtgc acgatgcgga aaagcccatt aagaacacca ccgtcaagag tgtgatcatg    3780
ctaatgttcc gcgaggagaa gagtcccgag gatgagatca aggcctggca attctggcac    3840
```

-continued

```
agtcgtcagc attccgtgaa gcagagaatc ttggatgcag atacgaagaa ctcggttggc    3900
ctcgttggct gcatcgagga agtgtcgcac aatgccatcg ccgtctactg gaatccgctg    3960
gagagctccg ccaagatcaa cattgcggtt cagtgcttga gcacggattt cagcagtcaa    4020
aagggaggcc tgccgctgca cgtacaaatc gacacatttg aggaccccag agatacggcg    4080
gtcttccacc gcggctactg tcagataaag gtcttctgcg ataagggcgc cgaacgaaag    4140
acgcgcgatg aagagcggcg ggccgccaaa cgaaagatga cagccacggg cagaaagaag    4200
ctggacgagc tttaccatcc ggtaacggat cggtccgagt tctatggcat gcaggacttc    4260
gccaagccgc cggtgctatt ctcgcccgcc gaggacatgg agaagagctt ctacggccat    4320
gagactgact cgccggacct gaaggggggcc tcaccgttcc tgctccacgg ccagaaggtg    4380
gccacgccga cgctcaagtt ccacaaccat tttccgcccg acatgcagac cgataagaag    4440
gatcacatac tggaccagaa catgttgacc agcacacccc tgaccgactt ggtccgccg    4500
atgaagcgcg gcaggatgac gccgccgacc tcggaacgcg tgatgctgta cgtgcggcag    4560
gagaacgagg aggtgtatac accgttgcac gtggtgccgc ccaccacgat cggcctgcta    4620
aatgcgattg aaaacaaata caaaatctca acaacgagca taataacat ttatcgcaca    4680
aacaagaagg ggattactgc gaaaattgac gatgacatga tatcgttcta ctgcaacgag    4740
gacatctttc tgctggaggt gcaacagatc gaggacgacc tgtacgatgt gacgctcacg    4800
gagctgccca tcagtagcg ctggcagtac gggtagcacc cgctaaccgc actcaaaaaa    4860
aaaagcaaac aaacacacaa attacggaca caacaagttg tttcaataag ccattttcca    4920
tagagcctaa gtctaaatat cgtagttata ataatgggat ccgcaacaaa tcgagttgca    4980
acgaatgtta agaacgctaa cacaatacgc atgtaaaatg atactttaaa attgatttag    5040
ttattttagc aacaatgaga ttatctaaaa ttgtttgatc aaattttaca ttctcgctat    5100
gtctatagat aattctaagc ccgtaagccc ataagcgtaa tcgtaatcgt aatcgtaccg    5160
tgtatttatg ctcatatata aacaactata tatatatata tatatatata tatgtgcgga    5220
gtgcaacagt gtctgtccag taggagataa gtctcgtttc cgctcccctg cttatgctat    5280
gaccttaggt ccagggcaag tatgagttac cgaatctatc tattaggtgc atctaacgaa    5340
aggaatcatt agctctgcac gaactctagc cgtagcctat tgtaatccat ttgtatgttt    5400
ggcttaagcg tttacttgt tgaatataaa gtgtaaaatt attttgaaa aaaaaaaacc    5460
cacacaaaac acaaatcgtt tgttctatat ttctgtttca aaactaactc gttacccaca    5520
atcccctctg ttatgtataa ttaggatctc tgtacac                             5557
```

<210> SEQ ID NO 39
<211> LENGTH: 1331
<212> TYPE: PRT
<213> ORGANISM: Drosophila

<400> SEQUENCE: 39

```
Met Ser Thr Ser Thr Ala Thr Thr Ser Val Ile Thr Ser Asn Glu Leu
1               5                   10                  15

Ser Leu Ser Gly His Ala His Gly Gly His Ala His Gln Leu His
            20                  25                  30

Gln His Thr His Ser Arg Leu Gly Val Gly Val Gly Val Ile Leu
        35                  40                  45

Ser Asp Ala Ser Leu Ser Pro Ile Gln Gln Gly Ser Gly Gly His Ser
    50                  55                  60

Gly Gly Gly Asn Thr Asn Ser Ser Pro Leu Ala Pro Asn Gly Val Pro
```

-continued

```
                65                  70                  75                  80
Leu Leu Thr Thr Met His Arg Ser Pro Asp Ser Pro Gln Pro Glu Leu
                    85                  90                  95
Ala Thr Met Thr Asn Val Asn Val Leu Asp Leu His Thr Asp Asn Ser
                    100                 105                 110
Lys Leu Tyr Asp Lys Glu Ala Val Phe Ile Tyr Glu Thr Pro Lys Val
                    115                 120                 125
Val Met Pro Ala Asp Gly Gly Gly Asn Asn Ser Asp Glu Gly His
                130                 135                 140
Ala Ile Asp Ala Arg Ile Ala Ala Gln Met Gly Asn Gln Ala Gln Gln
145                 150                 155                 160
Gln Gln Gln Gln Gln Gln Thr Glu His Gln Pro Leu Ala Lys Ile
                    165                 170                 175
Glu Phe Asp Glu Asn Gln Ile Ile Arg Val Val Gly Pro Asn Gly Glu
                180                 185                 190
Gln Gln Gln Ile Ile Ser Arg Glu Ile Ile Asn Gly Glu His His Ile
                    195                 200                 205
Leu Ser Arg Asn Glu Ala Gly Glu His Ile Leu Thr Arg Ile Val Ser
                210                 215                 220
Asp Pro Ser Lys Leu Met Pro Asn Asp Asn Ala Val Ala Thr Ala Met
225                 230                 235                 240
Tyr Asn Gln Ala Gln Lys Met Asn Asn Asp His Gly Gln Ala Val Tyr
                    245                 250                 255
Gln Thr Ser Pro Leu Pro Leu Asp Ala Ser Val Leu His Tyr Ser Gly
                260                 265                 270
Gly Asn Asp Ser Asn Val Ile Lys Thr Glu Ala Asp Ile Tyr Glu Asp
                275                 280                 285
His Lys Lys His Ala Ala Ala Ala Ala Ala Gly Gly Gly Ser
                290                 295                 300
Ile Ile Tyr Thr Thr Ser Asp Pro Asn Gly Val Asn Val Lys Gln Leu
305                 310                 315                 320
Pro His Leu Thr Val Pro Gln Lys Leu Asp Pro Asp Leu Tyr Gln Ala
                    325                 330                 335
Asp Lys His Ile Asp Leu Ile Tyr Asn Asp Gly Ser Lys Thr Val Ile
                340                 345                 350
Tyr Ser Thr Thr Asp Gln Lys Ser Leu Glu Ile Tyr Ser Gly Gly Asp
                355                 360                 365
Ile Gly Ser Leu Val Ser Asp Gly Gln Val Val Gln Ala Gly Leu
                370                 375                 380
Pro Tyr Ala Thr Thr Gly Ala Gly Gly Gln Pro Val Tyr Ile Val
385                 390                 395                 400
Ala Asp Gly Ala Leu Pro Ala Gly Val Glu Glu His Leu Gln Ser Gly
                    405                 410                 415
Lys Leu Asn Gly Gln Thr Thr Pro Ile Asp Val Ser Gly Leu Ser Gln
                420                 425                 430
Asn Glu Ile Gln Gly Phe Leu Leu Gly Ser His Pro Ser Ser Ser Ala
                435                 440                 445
Thr Val Ser Thr Thr Gly Val Val Ser Thr Thr Ile Ser His His
                450                 455                 460
Gln Gln Gln Gln Gln Gln Gln Gln Gln Gln Gln Gln Gln Gln Gln Gln
465                 470                 475                 480
Gln His Gln Gln Gln Gln His Pro Gly Asp Ile Val Ser Ala Ala
                    485                 490                 495
```

-continued

```
Gly Val Gly Ser Thr Gly Ser Ile Val Ser Ala Ala Gln Gln Gln
            500                 505                 510
Gln Gln Gln Gln Leu Ile Ser Ile Lys Arg Glu Pro Glu Asp Leu Arg
        515                 520                 525
Lys Asp Pro Lys Asn Gly Asn Ile Ala Gly Ala Thr Ala Asn Gly
        530                 535                 540
Pro Gly Ser Val Ile Thr Gln Lys Ile Leu His Val Asp Ala Pro Thr
545                 550                 555                 560
Ala Ser Glu Ala Asp Arg Pro Ser Thr Pro Ser Ser Ser Ile Asn Ser
                565                 570                 575
Thr Glu Asn Thr Glu Ser Asp Ser Gln Ser Val Ser Gly Ser Glu Ser
            580                 585                 590
Gly Ser Pro Gly Ala Arg Thr Thr Ala Thr Leu Glu Met Tyr Ala Thr
            595                 600                 605
Thr Gly Gly Thr Gln Ile Tyr Leu Gln Thr Ser His Pro Ser Thr Ala
        610                 615                 620
Ser Gly Ala Gly Gly Ala Gly Pro Ala Gly Ala Ala Gly Gly Gly
625                 630                 635                 640
Gly Val Ser Met Gln Ala Gln Ser Pro Ser Pro Gly Pro Tyr Ile Thr
                645                 650                 655
Ala Asn Asp Tyr Gly Met Tyr Thr Ala Ser Arg Leu Pro Pro Gly Pro
            660                 665                 670
Pro Pro Thr Ser Thr Thr Thr Phe Ile Ala Glu Pro Ser Tyr Tyr Arg
        675                 680                 685
Glu Tyr Phe Ala Pro Asp Gly Gln Gly Gly Tyr Val Pro Ala Ser Thr
    690                 695                 700
Arg Ser Leu Tyr Gly Asp Val Asp Val Ser Val Ser Gln Pro Gly Gly
705                 710                 715                 720
Val Val Thr Tyr Glu Gly Arg Phe Ala Gly Ser Val Pro Pro Ala
                725                 730                 735
Thr Thr Thr Val Leu Thr Ser Val His His Gln Gln Gln Gln
            740                 745                 750
Gln Gln Gln Gln His Gln Gln Gln Gln Gln Gln Gln His His Gln
        755                 760                 765
Gln Gln Gln His His Ser Gln Asp Gly Lys Ser Asn Gly Gly Ala Thr
        770                 775                 780
Pro Leu Tyr Ala Lys Ala Ile Thr Ala Ala Gly Leu Thr Val Asp Leu
785                 790                 795                 800
Pro Ser Pro Asp Ser Gly Ile Gly Thr Asp Ala Ile Thr Pro Arg Asp
                805                 810                 815
Gln Thr Asn Ile Gln Gln Ser Phe Asp Tyr Thr Glu Leu Cys Gln Pro
            820                 825                 830
Gly Thr Leu Ile Asp Ala Asn Gly Ser Ile Pro Val Ser Val Asn Ser
        835                 840                 845
Ile Gln Gln Arg Thr Ala Val His Gly Ser Gln Asn Ser Pro Thr Thr
    850                 855                 860
Ser Leu Val Asp Thr Ser Thr Asn Gly Ser Thr Arg Ser Arg Pro Trp
865                 870                 875                 880
His Asp Phe Gly Arg Gln Asn Asp Ala Asp Lys Ile Gln Ile Pro Lys
                885                 890                 895
Ile Phe Thr Asn Val Gly Phe Arg Tyr His Leu Glu Ser Pro Ile Ser
            900                 905                 910
```

-continued

```
Ser Ser Gln Arg Arg Glu Asp Asp Arg Ile Thr Tyr Ile Asn Lys Gly
        915                 920                 925

Gln Phe Tyr Gly Ile Thr Leu Glu Tyr Val His Asp Ala Glu Lys Pro
        930                 935                 940

Ile Lys Asn Thr Thr Val Lys Ser Val Ile Met Leu Met Phe Arg Glu
945                 950                 955                 960

Glu Lys Ser Pro Glu Asp Glu Ile Lys Ala Trp Gln Phe Trp His Ser
                965                 970                 975

Arg Gln His Ser Val Lys Gln Arg Ile Leu Asp Ala Asp Thr Lys Asn
        980                 985                 990

Ser Val Gly Leu Val Gly Cys Ile Glu Glu Val Ser His Asn Ala Ile
        995                 1000                1005

Ala Val Tyr Trp Asn Pro Leu Glu Ser Ser Ala Lys Ile Asn Ile
        1010                1015                1020

Ala Val Gln Cys Leu Ser Thr Asp Phe Ser Ser Gln Lys Gly Gly
        1025                1030                1035

Leu Pro Leu His Val Gln Ile Asp Thr Phe Glu Asp Pro Arg Asp
        1040                1045                1050

Thr Ala Val Phe His Arg Gly Tyr Cys Gln Ile Lys Val Phe Cys
        1055                1060                1065

Asp Lys Gly Ala Glu Arg Lys Thr Arg Asp Glu Glu Arg Arg Ala
        1070                1075                1080

Ala Lys Arg Lys Met Thr Ala Thr Gly Arg Lys Lys Leu Asp Glu
        1085                1090                1095

Leu Tyr His Pro Val Thr Asp Arg Ser Glu Phe Tyr Gly Met Gln
        1100                1105                1110

Asp Phe Ala Lys Pro Pro Val Leu Phe Ser Pro Ala Glu Asp Met
        1115                1120                1125

Glu Lys Val Gly Gln Leu Gly Ile Gly Ala Ala Thr Gly Met Thr
        1130                1135                1140

Phe Asn Pro Leu Ser Asn Gly Asn Ser Asn Ser Asn Ser His Ser
        1145                1150                1155

Ser Leu Gln Ser Phe Tyr Gly His Glu Thr Asp Ser Pro Asp Leu
        1160                1165                1170

Lys Gly Ala Ser Pro Phe Leu Leu His Gly Gln Lys Val Ala Thr
        1175                1180                1185

Pro Thr Leu Lys Phe His Asn His Phe Pro Pro Asp Met Gln Thr
        1190                1195                1200

Asp Lys Lys Asp His Ile Leu Asp Gln Asn Met Leu Thr Ser Thr
        1205                1210                1215

Pro Leu Thr Asp Phe Gly Pro Pro Met Lys Arg Gly Arg Met Thr
        1220                1225                1230

Pro Pro Thr Ser Glu Arg Val Met Leu Tyr Val Arg Gln Glu Asn
        1235                1240                1245

Glu Glu Val Tyr Thr Pro Leu His Val Val Pro Pro Thr Thr Ile
        1250                1255                1260

Gly Leu Leu Asn Ala Ile Glu Asn Lys Tyr Lys Ile Ser Thr Thr
        1265                1270                1275

Ser Ile Asn Asn Ile Tyr Arg Thr Asn Lys Lys Gly Ile Thr Ala
        1280                1285                1290

Lys Ile Asp Asp Asp Met Ile Ser Phe Tyr Cys Asn Glu Asp Ile
        1295                1300                1305

Phe Leu Leu Glu Val Gln Gln Ile Glu Asp Asp Leu Tyr Asp Val
```

```
                1310              1315          1320
      Thr Leu  Thr Glu Leu Pro Asn  Gln
         1325               1330
```

<210> SEQ ID NO 40
<211> LENGTH: 18
<212> TYPE: DNA
<213> ORGANISM: murine

<400> SEQUENCE: 40
ggatcagaag accatgcc                                                 18

<210> SEQ ID NO 41
<211> LENGTH: 18
<212> TYPE: DNA
<213> ORGANISM: murine

<400> SEQUENCE: 41
aggctgttag agttggtg                                                 18

<210> SEQ ID NO 42
<211> LENGTH: 18
<212> TYPE: DNA
<213> ORGANISM: murine

<400> SEQUENCE: 42
ctgtagccag ctttcatc                                                 18

<210> SEQ ID NO 43
<211> LENGTH: 19
<212> TYPE: DNA
<213> ORGANISM: murine

<400> SEQUENCE: 43
gctggtgaaa aggacctct                                                19

<210> SEQ ID NO 44
<211> LENGTH: 20
<212> TYPE: DNA
<213> ORGANISM: murine

<400> SEQUENCE: 44
cacaggacta gaacacctgc                                               20

<210> SEQ ID NO 45
<211> LENGTH: 17
<212> TYPE: DNA
<213> ORGANISM: murine

<400> SEQUENCE: 45
cacattgaag aggtggc                                                  17

<210> SEQ ID NO 46
<211> LENGTH: 20
<212> TYPE: DNA
<213> ORGANISM: MURINE

<400> SEQUENCE: 46
aagggtgagc aggttcgctt                                               20